(12) United States Patent
McCully et al.

(10) Patent No.: US 12,168,700 B2
(45) Date of Patent: *Dec. 17, 2024

(54) THERAPEUTIC USE OF MITOCHONDRIA AND COMBINED MITOCHONDRIAL AGENTS

(71) Applicants: Children's Medical Center Corporation, Boston, MA (US); Beth Israel Deaconess Medical Center, Inc., Boston, MA (US)

(72) Inventors: James D. McCully, Marblehead, MA (US); Sidney Levitsky, Boston, MA (US); Douglas B. Cowan, West Roxbury, MA (US); Pedro J. del Nido, Lexington, MA (US); Sitaram M. Emani, Boston, MA (US)

(73) Assignees: Children's Medical Center Corporation, Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/459,892

(22) Filed: Sep. 1, 2023

(65) Prior Publication Data
US 2023/0416413 A1  Dec. 28, 2023

Related U.S. Application Data

(60) Continuation of application No. 17/960,994, filed on Oct. 6, 2022, which is a continuation of application No. 16/451,910, filed on Jun. 25, 2019, now abandoned, which is a division of application No. 15/803,543, filed on Nov. 3, 2017, now Pat. No. 10,370,458, which is a continuation of application No. PCT/US2017/013564, filed on Jan. 13, 2017.

(60) Provisional application No. 62/420,381, filed on Nov. 10, 2016, provisional application No. 62/279,489, filed on Jan. 15, 2016, provisional application No. 62/279,442, filed on Jan. 15, 2016.

(51) Int. Cl.
| | |
|---|---|
| *C07K 16/46* | (2006.01) |
| *A61B 6/42* | (2024.01) |
| *A61B 6/50* | (2024.01) |
| *A61B 8/08* | (2006.01) |
| *A61K 9/00* | (2006.01) |
| *A61K 35/12* | (2015.01) |
| *A61K 35/28* | (2015.01) |
| *A61K 35/34* | (2015.01) |
| *A61K 39/00* | (2006.01) |
| *A61K 47/69* | (2017.01) |
| *A61K 49/00* | (2006.01) |
| *A61K 49/18* | (2006.01) |
| *A61K 51/04* | (2006.01) |
| *A61K 51/12* | (2006.01) |
| *C12N 15/11* | (2006.01) |

(52) U.S. Cl.
CPC .............. *C07K 16/468* (2013.01); *A61B 6/42* (2013.01); *A61K 9/0019* (2013.01); *A61K 35/12* (2013.01); *A61K 35/28* (2013.01); *A61K 35/34* (2013.01); *A61K 47/6901* (2017.08); *A61K 49/0002* (2013.01); *A61K 49/1821* (2013.01); *A61K 49/1896* (2013.01); *A61K 51/0421* (2013.01); *A61K 51/1203* (2013.01); *A61K 51/1282* (2013.01); *C12N 15/11* (2013.01); *A61B 6/503* (2013.01); *A61B 8/0883* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 2,561,043 | A | 7/1951 | Ayers |
| 2,854,143 | A | 9/1958 | Novak |
| 3,826,255 | A | 7/1974 | Diedrich et al. |
| 4,046,146 | A | 9/1977 | Rosskamp et al. |
| 4,253,468 | A | 3/1981 | Lehmbeck |
| 4,268,460 | A | 5/1981 | Boiarski et al. |
| 4,279,890 | A | 7/1981 | Harris et al. |
| 4,510,829 | A | 4/1985 | Kintzel et al. |
| 4,649,911 | A | 3/1987 | Knight et al. |
| 5,460,940 | A | 10/1995 | Yves et al. |
| 5,830,445 | A | 11/1998 | Bouillon et al. |
| 6,468,798 | B1 | 10/2002 | Debs et al. |
| 6,562,864 | B1 | 5/2003 | Larson |
| 6,693,086 | B1 | 2/2004 | Dow et al. |
| 6,695,227 | B1 | 2/2004 | Hayashi et al. |
| 6,777,227 | B2 | 8/2004 | Ricci et al. |
| 6,867,197 | B1 | 3/2005 | Davis et al. |
| 7,125,434 | B2 | 10/2006 | Yavorsky et al. |

(Continued)

FOREIGN PATENT DOCUMENTS

| | | |
|---|---|---|
| AU | 2001013622 | 7/2001 |
| CA | 3049099 | 5/2018 |

(Continued)

OTHER PUBLICATIONS

Hosseinian et al., Mitochondrion 65: 33-34 (Year: 2022).*

(Continued)

*Primary Examiner* — Phuong Huynh

(74) *Attorney, Agent, or Firm* — Fish & Richardson P.C.

(57) ABSTRACT

The disclosure relates to compositions comprising isolated mitochondria or combined mitochondrial agents, and methods of treating disorders using such compositions.

24 Claims, 30 Drawing Sheets

(56) References Cited

U.S. PATENT DOCUMENTS

| | | | |
|---|---|---|---|
| 7,279,326 B2 | 10/2007 | Weissig et al. | |
| 7,431,222 B2 | 10/2008 | Monterrosa | |
| 7,718,620 B2 | 5/2010 | Szeto et al. | |
| 7,745,651 B2 | 6/2010 | Heyes et al. | |
| 7,799,565 B2 | 9/2010 | MacLachlan et al. | |
| 7,803,397 B2 | 9/2010 | Heyes et al. | |
| 7,838,658 B2 | 11/2010 | MacLachlan et al. | |
| 7,901,708 B2 | 3/2011 | MacLachlan et al. | |
| 7,915,399 B2 | 3/2011 | MacLachlan et al. | |
| 7,923,984 B2 | 4/2011 | Philbert | |
| 7,982,027 B2 | 7/2011 | MacLachlan et al. | |
| 8,058,069 B2 | 11/2011 | Yaworski et al. | |
| 8,084,599 B2 | 12/2011 | Rossi et al. | |
| 8,101,741 B2 | 1/2012 | MacLachlan et al. | |
| 8,188,263 B2 | 5/2012 | MacLachlan et al. | |
| 8,236,943 B2 | 8/2012 | Lee et al. | |
| 8,283,333 B2 | 10/2012 | Yaworski et al. | |
| 8,349,809 B2 | 1/2013 | Brown | |
| 8,513,207 B2 | 8/2013 | Brown | |
| 8,616,195 B2 | 12/2013 | Power et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 8,999,641 B2 | 4/2015 | Zhang et al. | |
| 9,315,773 B2 | 4/2016 | Schiedner et al. | |
| 10,370,458 B2 * | 8/2019 | McCully | A61B 6/42 |
| 11,491,480 B2 | 11/2022 | McCully et al. | |
| 2001/0047966 A1 | 12/2001 | Colpan | |
| 2002/0046410 A1 * | 4/2002 | Lanza | A61K 49/0008 424/9.2 |
| 2004/0131641 A1 | 7/2004 | Mikszta et al. | |
| 2004/0161421 A1 | 8/2004 | Komowski et al. | |
| 2004/0192595 A1 | 9/2004 | Murakami et al. | |
| 2005/0224608 A1 | 10/2005 | Khan et al. | |
| 2007/0015777 A1 | 1/2007 | Bush et al. | |
| 2007/0128726 A1 | 6/2007 | Koob et al. | |
| 2008/0014144 A1 | 1/2008 | Saltzman et al. | |
| 2008/0260637 A1 | 10/2008 | Dickman | |
| 2008/0275005 A1 | 11/2008 | Murphy | |
| 2009/0202606 A1 | 8/2009 | Kim et al. | |
| 2011/0008310 A1 * | 1/2011 | Cataldo | A01K 67/0271 424/94.4 |
| 2011/0130309 A1 | 6/2011 | Cardone | |
| 2011/0177051 A1 | 7/2011 | Galski-Lorberboum | |
| 2011/0313143 A1 | 12/2011 | Martin et al. | |
| 2011/0321200 A1 | 12/2011 | Hyde et al. | |
| 2012/0039810 A1 | 2/2012 | Gorenstein et al. | |
| 2012/0107285 A1 | 5/2012 | Hyde et al. | |
| 2012/0107937 A1 * | 5/2012 | Hyde | A61K 31/713 435/375 |
| 2012/0110683 A1 | 5/2012 | Shomura et al. | |
| 2012/0171716 A1 | 7/2012 | Sun et al. | |
| 2013/0022666 A1 | 1/2013 | Brzezinska | |
| 2013/0149778 A1 | 6/2013 | Chang et al. | |
| 2013/0217114 A1 | 8/2013 | Yan et al. | |
| 2014/0051174 A1 | 2/2014 | Burke et al. | |
| 2014/0086886 A1 | 3/2014 | Westenfelder | |
| 2014/0106004 A1 | 4/2014 | Wong et al. | |
| 2014/0178993 A1 | 6/2014 | Chang et al. | |
| 2014/0193511 A1 | 7/2014 | Yivgi-Ohana et al. | |
| 2014/0314879 A1 | 10/2014 | Lawendy et al. | |
| 2015/0026833 A1 | 1/2015 | Ande et al. | |
| 2015/0079193 A1 | 3/2015 | Yivgi-Ohana et al. | |
| 2015/0344912 A1 | 12/2015 | Kim et al. | |
| 2016/0138008 A1 | 5/2016 | Doudna et al. | |
| 2016/0208243 A1 | 7/2016 | Zhang et al. | |
| 2017/0120237 A1 | 5/2017 | McCully et al. | |
| 2017/0151287 A1 * | 6/2017 | von Maltzahn | G01N 33/15 |
| 2017/0290763 A1 | 10/2017 | Su | |
| 2018/0057610 A1 | 3/2018 | McCully et al. | |
| 2018/0340022 A1 | 11/2018 | Lee | |
| 2020/0123273 A1 | 4/2020 | McCully et al. | |
| 2022/0160782 A1 | 5/2022 | McCully | |
| 2022/0347212 A1 | 11/2022 | McCully | |
| 2022/0395531 A1 | 12/2022 | McCully et al. | |
| 2023/0183380 A1 * | 6/2023 | McCully | A61K 47/6901 424/134.1 |
| 2023/0219081 A1 | 7/2023 | McCully et al. | |

FOREIGN PATENT DOCUMENTS

| | | |
|---|---|---|
| CN | 1187196 | 7/1998 |
| CN | 1662548 | 8/2005 |
| CN | 1832763 | 9/2006 |
| CN | 101146826 | 3/2008 |
| CN | 101693884 | 4/2010 |
| CN | 104662011 | 5/2015 |
| CN | 102791616 | 7/2015 |
| CN | 107249600 | 10/2017 |
| EP | 1766035 | 3/2007 |
| EP | 1781593 | 5/2007 |
| EP | 1519714 | 10/2010 |
| EP | 1664316 | 8/2012 |
| EP | 3402490 | 11/2018 |
| WO | WO 2006/059329 | 6/2006 |
| WO | WO 2008/137035 | 11/2008 |
| WO | WO 2008/152626 | 12/2008 |
| WO | WO 2012/085833 | 6/2012 |
| WO | WO 2013/035101 | 3/2013 |
| WO | WO 2013/171752 | 11/2013 |
| WO | WO 2014/113638 | 7/2014 |
| WO | WO 2015/192020 | 12/2015 |
| WO | WO 2016/135723 | 9/2016 |
| WO | WO 2017/095940 | 6/2017 |
| WO | WO 2017/095944 | 6/2017 |
| WO | WO 2017/095946 | 6/2017 |
| WO | WO 2017/124037 | 7/2017 |
| WO | WO 2020/214644 | 10/2020 |

OTHER PUBLICATIONS

Deuse et al., Cell Stem Cell 16: 33-38 (Year: 2015).*
Kholmukhamedov et al., Shock 39(6): 1-2 (Year: 2013).*
CA Office Action in Canadian Appln. No. 3,011,472, mailed on Aug. 29, 2023, 5 pages.
CN Office Action in Chinese Appln. No. 202080039304.2, mailed on Aug. 3, 2023, 16 pages (with English translation).
EP Office Action in European Appln. No. 20790601.7, mailed on Oct. 11, 2023, 3 pages.
JP Office Action in Japanese Appln. No. 2022188165, mailed on Oct. 23, 2023, 8 pages (with English translation).
Ahmad et al., "Mirol regulates intercellular mitochondrial transport & enhances mesenchymal stem cell rescue efficacy," The EMBO Journal, May 2, 2014, 33(9):994-1010.
Akurathi et al., "Preliminary Evaluation of 18F-Rhodamine 6G as a Tumor-Imaging Agent," J Nucl Med, May 2013, 54 (Supplement 2): 1148, 2 pages.
Alfonzo et al., "Mitochondrial tRNA import-the challenge to understand has just begun." Biol. Chem, Jun. 2009, 390(8):717-722.
Allen et al., "Angiopellosis as an Alternative Mechanism of Cell Extravasation," Stem Cells, Jan. 2017, 35:170-180.
Altschul et al."Basic Local Alignment Search Tool," Journal of molecular biology, Oct. 5, 1990, 215(3):403-10.
Angsutararux et al., "Chemotherapy-Induced Cardiotoxicity: Overview of the Roles of Oxidative Stress," Oxid Med Cell Longev, Oct. 2015, 795602, 13 pages.
Arora et al., "Cell Culture Media: a Review" Mater Methods, Sep. 2013, 3(175):24, 1-21.
AU Office Action in Australian Application No. 2017208013, dated Nov. 16, 2021, 7 pages.

(56) References Cited

OTHER PUBLICATIONS

AU Office Action in Australian Application No. 2021201217, dated Feb. 1, 2022, 5 pages.
AU Office Action in Australian Appln. No. 2015274367, dated Oct. 8, 2020, 5 pages.
AU Office Action in Australian Appln. No. 2021201217, dated Jan. 18, 2023, 4 pages.
Augustin et al., "Characterization of peptides released from mitochondria: evidence for constant proteolysis and peptide efflux," Journal of Biological Chemistry, Jan. 28, 2005, 280(4):2691-9.
Bacman et al., "Specific elimination of mutant mitochondrial genomes in patient-derived cells by mitoTALENs," Nature Medicine, Sep. 2013, 19(9):1111-3.
Bansal et al., "Photocontrolled nanoparticle delivery systems for biomedical applications," Accounts of Chemical Research, Oct. 2014, 47(10), 3052-3060.
Barhoumi et al., "Ultraviolet light-mediated drug delivery: Principles, applications, and challenges," Journal of Controlled Release, Dec. 2015, 219, 40 pages.
Bartel, "MicroRNAs: Genomics, Biogenesis, Mechanism, and Function," Cell, Jan. 23, 2004, 116:281-97.
Bartholomä et al., "18F-labeled rhodamines as potential myocardial perfusion agents: comparison of pharmacokinetic properties of several rhodamines," Nuclear Medicine and Biology, Oct. 1, 2015, 42(10):796-803.
Bartholomä et al., "Biological characterization of F18-labeled Rhodamine B, a potential positron emission tomography perfusion tracer," Nuclear Medicine and Biology, Nov. 1, 2013, 40(8): 1043-8.
Bayeva et al., "Mitochondria as a therapeutic target in heart failure," Journal of the American College of Cardiology, Feb. 12, 2013, 61(6):599-610.
Bensley et al., "Studies on cell structure by the freezing-drying method VI. The preparation and properties of mitochondria," Anat Rec, Nov. 1934, 60:449-455.
Bershteyn et al., "Polymer-supported lipid shells, onions, and flowers," Soft Matter, Jan. 2008, 4(9):1787-91.
Birch-Machin et al., "An Evaluation of the Measurement of the Activities of Complexes I-IV in the Respiratory Chain of Human Skeletal Muscle Mitochondria," Biochemical Medicine and Metabolic Biology, 51:35-42, Feb. 1994, 35-42.
Birsoy et al., "An Essential Role of the Mitochondrial Electron Transport Chain in Cell Proliferation Is to Enable Aspartate Synthesis," Cell, Jul. 2015, 162: 540-551.
Black et al., "Microarray and proteomic analysis of the cardioprotective effects of cold blood cardioplegia in the mature and aged male and female," Physiological Genomics, Nov. 1, 2012, 44(21): 1027-41.
Boezeman et al., "Systematic review of clinical applications of monitoring muscle tissue oxygenation with near-infrared spectroscopy in vascular disease," Microvasc Res, Mar. 2016, 104, 47 pages.
Boldogh et al., "Cell-Free Assays for Mitochondria—Cytoskeleton Interactions," Methods in Cell Biology, Jan. 1, 2007, 80:683-706.
Bolender et al., "Multiple pathways for sorting mitochondrial precursor proteins," EMBO Reports, Jan. 2008, 9(1):42-9.
Boudreau et al. (2014). Platelets release mitochondria serving as substrate for bactericidal group IIA-secreted phospholipase A2 to promote inflammation. Blood 124(14): 2173-2183.
Brown et al., "Mitochondrial function as a therapeutic target in heart failure," Nature Reviews Cardiology, Apr. 2017, 14(4):238-50.
CA Office Action in Canadian Appln. No. 3,011,472, dated Jan. 12, 2023, 5 pages.
CA Office Action in Canadian Appln. No. 2,952,121, dated Aug. 9, 2021, 4 pages.
Calvo et al., "MitoCarta2. 0: an updated inventory of mammalian mitochondrial proteins," Nucleic Acids Research, Jan. 4, 2016, 44(D1):D1251-7.
Cameron et al., "Development of therapeutics that induce mitochondrial biogenesis for the treatment of acute and chronic degenerative diseases," Journal of Medicinal Chemistry, Dec. 8, 2016, 59(23):10411-34.
Cannon et al., "Brown Adipose Tissue: Function and Physiological Significance," Physiol Rev, Jan. 2004, 84: 277-359.
Cavers et al., "Chondriosomes (mitochondria) and their significance," New Phytologist, Mar. 1, 1914, 13(3):96-106.
Cedikova et al., "Mitochondria in white, brown, and beige adipocytes," Stem cells international, 2016:1-11, Jan. 2016.
Cell Biology a Laboratory Handbook, 3rd ed., Fernandez-Vizaeea et al., Nov. 2005, Chapter 10, 12 Pages.
Chance et al., "A simple and rapid assay of oxidative phosphorylation," Nature, Jun. 1955, 175(4469):1120-1.
Chance, "The interaction of energy and electron transfer reactions in mitochondria: II. General properties of adenosine triphosphate-linked oxidation of cytochrome and reduction of pyridine nucleotide," Journal of Biological Chemistry, May 1, 1961, 236(5): 1544-54.
Chang et al., "Treatment of human cells derived from MERRF syndrome by peptide-mediated mitochondrial delivery," Cytotherapy, Dec. 1, 2013, 15(12):1580-96.
Chattopadhyay et al., "T3 fails to restore mitochondrial thiol redox status altered by experimental hypothyroidism in rat testis," General and Comparative Endocrinology, Oct. 1, 2010, 169(1):39-47.
Chen et al., "Absolute quantification of matrix metabolites reveals the dynamics of mitochondrial metabolism," Cell, Aug. 2016, 166(5): 1324-37.
Cheng et al., "Brief report: Mechanism of extravasation of infused stem cells," Stem Cells, 2012, 30: 2835-2842.
Choi et al., "Cardiac conduction through engineered tissue," The American Journal of Pathology, Jul. 1, 2006, 169(1):72-85.
Claude, "Fractionation of Mammalian Liver Cells By Differential Centrifugation," J Exp Med, Apr. 1946, 84:61-89.
CN Office Action in Chinese Application No. 201580039651.4, dated Jul. 4, 2018, 9 pages (English translation).
CN Office Action in Chinese Application No. 201580039651.4, dated May 5, 2019, 9 pages (English translation).
CN Office Action in Chinese Appln. No. 201580039651.4, dated Aug. 17, 2020, 37 pages (with English translation).
CN Office Action in Chinese Appln. No. 201580039651.4, dated Jan. 21, 2021, 10 pages (with English translation).
CN Office Action in Chinese Appln. No. 201780013452.5, dated Jan. 31, 2023, 13 pages (with English translation).
CN Office Action in Chinese Appln. No. 201780013452.5, dated Jun. 21, 2023, 16 pages (with English translation).
CN Office Action in Chinese Appln. No. 201780013452.5, dated Nov. 19, 2021, 10 pages (with English translation).
CN Office Action in Chinese Appln. No. 202080028568.8, mailed on Jul. 26, 2023, 14 pages (with English translation).
CN Office Action in Chinese Appln. No. 2022111501695770, dated Nov. 18, 2022, 19 pages (with English translation).
Colman, "Effects of amino acid sequence changes on antibody-antigen interactions," Research in Immunology, Jan. 1, 1994, 145(1):33-6.
Cong et al., "Multiplex genome engineering using CRISPR/Cas systems," Science, Feb. 15, 2013, 339(6121):819-23.
Cowan et al., "Intracoronary delivery of mitochondria to the ischemic heart for cardioprotection." PloS one, Aug. 2016, 11(8): e0160889, 19 pages.
Cramer et al., "Methods for mycelial breakage and isolation of mitochondria and vacuoles of neurospora," Analytical Biochemistry, Feb. 1983, 128: 384-392.
Cypess et al., "Brown fat as a therapy for obesity and diabetes." Current Opinion in Endocrinology, Diabetes, and Obesity, Apr. 2010, 17: 143-149.
Dare et al., "The mitochondria-targeted anti-oxidant MitoQ decreases ischemia-reperfusion injury in a murine syngeneic heart transplant model," J Heart Lung Transplant, Nov. 2015, 34(11):1471-80.
Doench et al., "siRNAs can function as miRNAs," Genes & Development, Feb. 15, 2003, 17(4):438-42.
Doenst et al., "Cardiac metabolism in heart failure: implications beyond ATP production," Circulation Research., Aug. 30, 2013, 113(6):709-24.
Dolezal et al., "Evolution of the molecular machines for protein import into mitochondria," Science, Jul. 21, 2006, 313(5785):314-8.

(56) References Cited

OTHER PUBLICATIONS

Doulamis et al., "Mitochondrial transplantation for myocardial protection in diabetic hearts," European Journal of Cardio-Thoracic Surgery, May 1, 2020, 57(5): 836-45.
Ejsing et al., "Global analysis of the yeast lipidome by quantitative shotgun mass spectrometry," Proceedings of the National Academy of Sciences, Feb. 17, 2009, 106(7):2136-41.
Elliott et al., "Mitochondria organelle transplantation: introduction of normal epithelial mitochondria into human cancer cells inhibits proliferation and increases drug sensitivity," Breast Cancer Res. Treat., 2012, 136:347-354.
Emani et al., "Autologous mitochondrial transplantation for dysfunction after ischemia-reperfusion injury," The Journal of Thoracic and Cardiovascular Surgery, Jul. 1, 2017, 154(1):286-9.
EP European Search Report in European Appln. No. 20155650.3, dated Aug. 13, 2020, 15 pages.
EP European Search Report in European Appln. No. 20155650.3, dated Sep. 21, 2020, 17 pages.
EP European Search Report in European Appln. No. 20790601.7, dated Nov. 17, 2022, 12 pages.
EP Extended European Search Report in European Application No. 17739105.9 dated Jul. 8, 2019, 10 pages.
EP Extended European Search Report in European Appln. No. 20155650.3, dated Jan. 12, 2021, 14 pages.
EP Extended European Search Report issued in European Patent Application No. 16871432.7, dated Jun. 4, 2019, 8 pages.
EP Extended European Search Report issued in European Patent Application No. 16871436.8, dated Jun. 4, 2019, 7 pages.
EP Extended Search Report in European Appln. No. 19926810.3, dated Jan. 5, 2023, 11 pages.
EP Extended Search Report in European Appln. No. 20756733.0, dated Oct. 21. 2022, 12 pages.
EP Extended Search Report in European Appln. No. 20790601.7, dated Feb. 17, 2023, 10 pages.
EP Office Action by European Appln. No. 20155650.3, dated Dec. 15, 2021, 5 pages.
EP Office Action in European Application No. 15733576.1, dated May 3, 2018, 5 pages.
EP Office Action in European Appln. No. 20155650.3, dated Dec. 6, 2022, 4 pages.
EP Partial Supplementary European Search Report issued in European Patent Application No. 16871434.3, dated Jun. 4, 2019, 12 pages.
Ernster et al., "Mitochondria: a historical review," The Journal of Cell Biology, Dec. 1981, 91(3):227s-55s.
Facundo et al., "Mitochondrial ATP-sensitive K+ channels are redox-sensitive pathways that control reactive oxygen species production," ScienceDirect, Apr. 1, 2007, 42(7):1039-1048.
Faulk et al., "Magnesium cardioplegia enhances mRNA levels and the maximal velocity of cytochrome oxidase I in the senescent myocardium during global ischemia," Circulation, Nov. 1, 1995, 92(9):405-12.
Faulk et al., "Myocardial mitochondrial calcium accumulation modulates nuclear calcium accumulation and DNA fragmentation," The Annals of thoracic surgery, Aug. 1, 1995, 60(2):338-44.
Feng et al., "Isolation and Observation of Mitochondrion," Experimental Instructions for Cell Biology and Cell Engineering Experiments, Human Science and Technology Press, Aug. 1, 2013, 39-41, 10 pages (English translation of the relevant portion is provided).
Fernández-Vizarra et al., "Tissue-specific differences in mitochondrial activity and biogenesis," Mitochondrion, Jan. 1, 2011, 11(1):207-13.
Fernandez-Vizarra et al., "Isolation of mitochondria for biogenetical studies: An update," Mitochondrion, Apr. 2010, 10:253-262.
Finkel et al., "The ins and outs of mitochondrial calcium," Circulation Research, May 22, 2015, 116(11):1810-9.
Flaquer et al., "Mitochondrial genetic variants identified to be associated with posttraumatic stress disorder," Translational Psychiatry, Mar. 2015, 5(3):e524, 7 pages.
Frezza et al., "Organelle isolation: functional mitochondria from mouse liver, muscle and cultured filroblasts," Nature Protocols, 2007, 2(2): 287-295.
Friehs et al., "Pressure-overload hypertrophy of the developing heart reveals activation of divergent gene and protein pathways in the left and right ventricular myocardium," American Journal of Physiology-Heart and Circulatory Physiology, Mar. 1, 2013, 304(5):H697-708.
Gabriel et al., "The mitochondrial machinery for import of precursor proteins," Protein Targeting Protocols, Jan. 2007, 390, 99-117.
Geng et al., "Microfluidic electroporation for cellular analysis and delivery," Lab on a Chip, 2013, 13(19):3803-21.
Glancy et al., "Effect of calcium on the oxidative phosphorylation cascade in skeletal muscle mitochondria," Biochemistry, Apr. 23, 2013, 52(16):2793-809.
Gostimskaya et al., "Preparation of highly coupled rat heart mitochondria," Sep. 2010, J Vis Exp, 43: e2202, 4 pages.
Graham et al., "Isolation of Mitochondria from Tissues and UNIT 3.3 Cells by Differential Centrifugation," Current Protocol in Cell Biology, May 2001, 3(3.3), 15 pages.
Graham et al., "Isolation of nuclei and nuclear membranes from animal tissues," Current Protocols in Cell Biology, Oct. 2001, 12(1):3-10.
Gram et al., "Skeletal muscle mitochondrial H2O2 emission increases with immobilization and decreases after aerobic training in young and older men," The Journal of Physiology, Sep. 1, 2015, 593(17):4011-27.
Green et al., "Metabolic, enzymatic, and transporter responses in human muscle during three consecutive days of exercise and recovery," American Journal of Physiology-Regulatory, Integrative and Comparative Physiology, Oct. 2008, 295(4):R1238-50.
Grieve et al., "Microvascular obstruction by intracoronary delivery of mesenchymal stem cells and quantification of resulting myocardial infarction by cardiac magnetic resonance," Circulation: Heart Failure, May 2010, 3(3):e5-6, 3 pages.
Gross et al., "Isolation of functional mitochondria from rat kidney and skeletal muscle without manual homogenization," Anal Biochem, Nov. 2011, 418:213- 223.
Guo et al., "Cardiovascular toxicities from systemic breast cancer therapy," Front Oncol, Dec. 4, 2014, 10 pages.
Hamilton, "The Mitochondria Mystery: Hidden risks for 'three-person' babies," Nature, Sep. 2015, 525(7570):444-6.
Han et al., "An unexpectedly labile mitochondrially encoded protein is required for Mta expression," Immunogenetics, Jul. 1989, 29: 258-264.
Hao et al., "Hydroxytyrosol promotes mitochondrial biogenesis and mitochondrial function in 3T3-LI adipocytes," The Journal of Nutritional Biochemistry, Jul. 1, 2010, 21(7):634-44.
Harms et al., "Brown and beige fat: development, function and therapeutic potential," Nature Medicine, Oct. 2013, 19: 1252-1263.
Hartwig et al., "A critical comparison between two classical and a kit-based method for mitochondria isolation," Proteomics, Jun. 2009, 9(11):3209-14.
Hendel et al., "Chemically modified guide RNAs enhance CRISPR-Cas genome editing in human primary cells," Nature Biotechnology, Sep. 2015, 33(9):985-9.
Herzog et al., "A novel informatics concept for high-throughput shotgun lipidomics based on the molecular fragmentation query language," Genome Biology, Jan. 2011, 12(1):1-25.
Herzog et al., "LipidXplorer: a software for consensual cross-platform lipidomics," PLoS One, PloS one, Jan. 17, 2012, 7(1):e29851, 7 pages.
Hoeper et al., "Mortality in pulmonary arterial hypertension: prediction by the 2015 European pulmonary hypertension guidelines risk stratification model," European Respiratory Journal, Aug. 1, 2017, 50(2), 10 pages.
Hogeboom et al., "Cytochemical studies of mammalian tissues; isolation of intact mitochondria from rat liver; some biochemical properties of mitochondria and submicroscopic particulate material," J Biol Chem, Feb. 1948, 172:619-635.
Ikon et al., "Exogenous cardiolipin localizes to mitochondria and prevents TAZ knockdown-induced apoptosis in myeloid progenitor cells," Biochem Biophys Res Commun, Aug. 2015, 464(2):580-5.

(56) References Cited

OTHER PUBLICATIONS

Islam et al., "Mitochondrial transfer from bone-marrow-derived stromal cells to pulmonary alveoli protects against acute lung injury," Nature Medicine, May 2012, 18: 759-765.
Jo et al., "Efficient mitochondrial genome editing by CRISPR/Cas9," BioMed Research International, Oct. 2015, vol. 2015.
JP Japanese Office Action in Japanese Appln. No. 2017-517221, dated Dec. 22, 2022, 6 pages (with English translation).
JP Japanese Office Action in Japanese Appln. No. 2018-536875, dated Dec. 27, 2021, 15 pages (with English translation).
JP Japanese Office Action in Japanese Appln. No. 2020-173126, dated Jul. 12, 2023, 5 pages (with English translation).
JP Japanese Office Action in Japanese Appln. No. 2020-173126, dated Nov. 1, 2022, 5 pages (with English translation).
JP Office Action in Japanese Appln. No. 2017-517221, dated Mar. 19, 2019, 4 pages.
JP Office Action in Japanese Appln. No. 36443-0031002, dated Jan. 27, 2021, 22 pages (with English translation).
Kalogeris et al., "Cell biology of ischemia/reperfusion injury. International review of cell and molecular biology," Jan. 1, 2012, 298:229-317.
Kassab et al., "Morphometry of pig coronary arterial trees," American Journal of Physiology-Heart and Circulatory Physiology, Jul. 1, 1993, 265(1):H350-65.
Kaul et al., "Insulin resistance in type 1 diabetes mellitus," Metabolism, Dec. 2015, 64(12), 39 pages.
Kaza et al., "Myocardial rescue with autologous mitochondrial transplantation in a porcine model of ischemia/reperfusion," The Journal of Thoracic and Cardiovascular Surgery, Apr. 2017, 153(4), 934-943.
Keeney et al., "Mitochondrial gene therapy augments mitochondrial physiology in a Parkinson's disease cell model," Human Gene Therapy, Aug. 1, 2009, 20(8):897-907.
Kirby et al., "Biochemical assays of respiratory chain complex activity," Methods in Cell Biology, Jan. 1, 2007, 80:93-119.
Kishida et al., "Reprogrammed Functional Brown Adipocytes Ameliorate Insulin Resistance and Dyslipidemia in Diet-Induced Obesity and Type 2 Diabetes," Stem Cell Reports, Oct. 2015, 5(4):569-81.
Kitani et al., "Internalization of isolated functional mitochondria: involvement of micropinocytosis," Journal of Cellular and Molecular Medicine, Aug. 2014, 18(8):1694-703.
Kornfeld et al., "Mitochondrial reactive oxygen species at the heart of the matter: new therapeutic approaches for cardiovascular diseases," Circulation Research, May 22, 2015, 116(11):1783-99.
Kunze et al., "The similarity between N-terminal targeting signals for protein import into different organelles and its evolutionary relevance," Frontiers in Physiology, Sep. 24, 2015, 6:259, 27 pages.
Kusminski et al., "Mitochondrial dysfunction in white adipose tissue," Trends in endocrinology & metabolism, 23(9):435-43, Sep. 2012.
Lang et al., "Recommendations for cardiac chamber quantification by echocardiography in adults: an update from the American Society of Echocardiography and the European Association of Cardiovascular Imaging," European Heart Journal-Cardiovascular Imaging, Mar. 1, 2015, 16(3):233-71.
Lau et al., "The 2015 ESC/ERS Guidelines for the diagnosis and treatment of pulmonary hypertension: a practical chronicle of progress," European Respiratory Journal, Oct. 1, 2015, 46(4):879-82.
Layland et al., "Adenosine: physiology, pharmacology, and clinical applications," JACC: Cardiovascular Interventions, Jun. 2014, 7(6):581-91.
Levitsky et al., "Mitochondrial DNA deletions in coronary artery bypass grafting patients," European Journal of Cardio-thoracic Surgery, Nov. 2003, 24: 777-784.
Lim et al., "Microarray analysis shows that some microRNAs downregulate large numbers of target mRNAs," Nature, Feb. 2005, 433(7027):769-73.

Lim et al., "Cold-induced activation of brown adipose tissue and adipose angiogenesis in mice," Nature Protocols, Mar. 2012, 7: 606-615.
Lim et al., "Levosimendan Reduces Mortality in Adults with Left Ventricular Dysfunction Undergoing Cardiac Surgery: a Systematic Review and Meta-analysis," J Card Surg, Jul. 2015, 30(7):547-54.
Lin et al."Incorporation of VSV-G produces fusogenic plasma membrane vesicles capable of efficient transfer of bioactive macromolecules and mitochondria" Biomed Microdevices (2016) 18: 41.
Lin et al., "Isolated mitochondria infusion mitigates ischemia-reperfusion injury of the liver in rats," Shock, Mar. 2013, 39: 304-310.
Lin et al., "Human white adipose tissue vasculature contains endothelial colony-forming cells with robust in vivo vasculogenic potential," Angiogenesis, Oct. 2013, 16(4): 735-744.
Liu et al., "Disrupted Renal Mitochondrial Homeostasis after Liver Transplantation in Rats," PLoS One, Oct. 2015, 10(10):e0140906.
Maniataki et al., "Human mitochondrial tRNAMet is exported to the cytoplasm and associates with the Argonaute 2 protein." RNA, Jun. 1, 2005, 11(6):849-52.
Masuzawa et al., "Transplantation of autologously derived mitochondria protects the heart from ischemia-reperfusion injury," Amer J Physiol Heart Circ Physiol, Apr. 2013, 304:H966-H982.
Matsuda et al., "Developmental Differences in Cytosolic Calcium Accumulation Associated With Global Ischemia Evidence for Differential Intracellular Calcium Channel Receptor Activity," Circulation, Nov. 1997, 96(9 Supp):II-233-9.
McCully et al., "Injection of isolated mitochondria during early reperfusion for cardioprotection," American Journal of Physiology-Heart and Circulatory Physiology, Jan. 2009, 296: H94-H105.
McCully et al., "Abstract 2272: Mitochondrial Transplantation for Cardioprotection," Circulation, Oct. 2007, 116: II, 2 pages.
McCully et al., "Mitochondrial transplantation for therapeutic use," Clin. Trans. Med., Dec. 2016, 5:16, 13 pages.
McCully et al., "Adenosine-enhanced ischemic preconditioning: adenosine receptor involvement during ischemia and reperfusion," Am J Heart Cir Physiol, Feb. 2001, 280: H591-H602.
McCully et al., "Age-and Gender-Related Differences in Mitochondrial Oxygen Consumption and Calcium With Cardioplegia and Diazoxide," Ann Thorac Surg, Mar. 2007, 83: 1102-9.
McMurray et al., "Heart failure," Lancet, May 2005, 365:1877-89.
MCully et al., "Diazoxide Amelioration of Myocardial Injury and Mitochondrial Damage During Cardiac Surgery," Ann Thorac Surg, Dec. 2002, 74: 2138-46.
Melero-Martin et al., "In vivo vasculogenic potential of human blood-derived endothelial progenitor cells," Blood, Jun. 2007, 109(11), 4761-4768.
Mercer et al., "Operating characteristics of some compressed-air nebulizers," American Industrial Hygiene Association Journal, Jan. 1, 1968, 29(1):66-78.
Millar et al. "Isolation and subfractionation of mitochondria from plants," Methods in cell biology, Jan. 1, 2001, 65:53-74.
Moskowitzova et al., "Mitochondrial transplantation prolongs cold ischemia time in murine heart transplantation," The Journal of Heart and Lung Transplantation, Jan. 1, 2019, 38(1):92, 25 pages.
Mumtaz et al., "Design of liposomes for circumventing the reticuloendothelial cells," Glycobiol, Nov. 1991, 1 (5): 505-510.
Néchad et al., "Development of brown fat cells in monolayer culture: I. Morphological and biochemical distinction from white fat cells in culture," Experimental Cell Research, Nov. 1, 1983, 149(1):105-18.
Neubauer, "The failing heart—an engine out of fuel," New England Journal of Medicine, Mar. 15, 2007, 356(11): 1140-51.
Nishikawa et al., "Nonviral vectors in the new millennium: delivery barriers in gene transfer," Human Gene Therapy, May 20, 2001, 12(8):861-70.
Noly et al., "Right ventricular mitochondrial respiratory function in a piglet model of chronic pulmonary hypertension," The Journal of Thoracic and Cardiovascular Surgery, Jan. 1, 2020, 159(1):129-40.
Novak et al., "Preparation of subcellular fractions suitable for biochemical analyses from human subcutaneous adipose tissue

(56) References Cited

OTHER PUBLICATIONS obtained by needle biopsy—I. Isolation of mitochondria on a microscale," Experimental Cell Research, Aug. 1972, 73: 335-344.

Novobrantseva et al., "Systemic RNAi-mediated gene silencing in nonhuman primate and rodent myeloid cells," Molecular Therapy-Nucleic Acids, Jan. 1, 2012, 1:e4, 13 pages.

O'Connell et al., "The effects of cryopreservation on sperm morphology, motility and mitchondrial function," Human Reproduction, Mar. 1, 2002, 17(3):704-9.

Olson et al., "Changes in endogenous substrates of isolated rabbit heart mitochondria during storage," Journal of Biological Chemistry, Jan. 25, 1967, 242(2):325-32.

Orive et al., "Cell encapsulation: technical and clinical advances," Trends in Pharmacological Sciences, Aug. 1, 2015, 36(8):537-46.

Orme-Johnson, "Appendix 2. Direct and indirect inhibitors of mitochondrial ATP synthesis," Methods in Cell Biology, 2007, 80:813-26.

Pacak et al., "Actin-dependent mitochondrial internalization in cardiomyocytes: evidence for rescue of mitochondrial function," Biology Open, Jul. 2015, 4: 622-626.

Pacak et al., "Superparamagnetic iron oxide nanoparticles function as a long-term, multi-modal imaging label for non-invasive tracking of implanted progenitor cells," PLoS One, Sep. 24, 2014, 9(9):e108695.

Pallotti et al., "Isolation and subfractionation of mitochondria from animal cells and tissue culture lines," Methods in Cell Biology, Jan. 1, 2001, 65:1-35.

PCT International Preliminary Report on Patentability in International Application No. PCT/US2017/013564, dated Jul. 17, 2018, 14 pages.

PCT International Preliminary Report on Patentability in International Appln. No. PCT/US2019/058924, dated Nov. 2, 2021, 11 pages.

PCT International Preliminary Report on Patentability in International Appln. No. PCT/US2020/018371, dated Aug. 10, 2021, 12 pages.

PCT International Preliminary Report on Patentability in International Appln. No. PCT/US2020/028219, dated Sep. 28, 2021, 10 pages.

PCT International Search Report and Written Opinion in International Application No. PCT/US2015/035584, dated Sep. 2, 2015, 12 pages.

PCT International Search Report and Written Opinion in International Application No. PCT/US2016/064238, dated Apr. 13, 2017, 13 pages.

PCT International Search Report and Written Opinion in International Application No. PCT/US2016/064247 dated May 10, 2017, 16 pages.

PCT International Search Report and Written Opinion in International Application No. PCT/US2016/064251 dated May 8, 2017, 15 pages.

PCT International Search Report and Written Opinion in International Application No. PCT/US2017/013564, dated Jun. 5, 2017, 12 pages.

PCT International Search Report and Written Opinion in International Appln. No. PCT/US2019/058924, dated Jan. 21, 2020, 17 pages.

PCT International Search Report and Written Opinion in International Appln. No. PCT/US2020/018371, dated May 7, 2020, 14 pages.

PCT International Search Report and Written Opinion in International Appln. No. PCT/US2020/028219, dated Jul. 15, 2020, 12 pages.

Peschechera et al., ""Browning" of adipose tissue-regulation and therapeutic perspectives," Archives of physiology and biochemistry, 119(4):151-60, Oct. 2013.

Pfanner et al., "Assembling the mitochondrial outer membrane," Nature Structural & Molecular Biology, Nov. 2004, 11(11):1044-8.

Phillips et al., "Homogenous protein programming in the mammalian left and right ventricle free walls," Physiological Genomics, Nov. 2011, 43(21):1198-206.

Phinney et al., "Mesenchymal stem cells use extracellular vesicles to outsource mitophagy and shuttle microRNAs," Nature Communications, Oct. 7, 2015, 6(1):1-5.

Pinton et al., "Biosensors for the detection of calcium and pH," Methods in Cell Biology, Jan. 1, 2007, 80:297-325.

Preble et al., "Quality Control Parameters for Mitochondria Transplant in Cardiac Tissue," Mol. Biol., Jun. 2, 2014, 2(1):1008.

Preble et al., "Rapid isolation and purification of mitochondria for transplantation by tissue dissociation and differential filtration," JoVE (Journal of Visualized Experiments), Sep. 6, 2014, (91):e51682, 6 pages.

Quirós et al., "New roles for mitochondrial proteases in health, ageing and disease," Nature Reviews Molecular Cell biology, Jun. 2015, 16(6):345-59.

Rahman et al., "Demarcating the membrane damage for the extraction of functional mitochondria," Microsystems & Nanoengineering, Dec. 31, 2018, 4(1): 1-2.

Rajewsky, "microRNA target predictions in animals," Nature Genetics, Jun. 2006, 38(6):S8-13.

Ran et al., "Double nicking by RNA-guided CRISPR Cas9 for enhanced genome editing specificity," Cell, Sep. 12, 2013, 154(6):1380-9.

Ran et al., "Genome engineering using the CRISPR-Cas9 system," Nature Protocols, Nov. 2013, 8(11):2281-308.

Risum et al., "Variability of global left ventricular deformation analysis using vendor dependent and independent two-dimensional speckle-tracking software in adults," Journal of the American Society of Echocardiography, Nov. 1, 2012, 25(11):1195-203.

Rodiger et al., "Simultaneous isolation of intact mitochondria and chloroplasts from a single pulping of plant tissue," Journal of Plant Physiology, May 2010, 167: 620-624.

Rogers et al., "When Cells Become Organelle Donors," Physiology, Nov. 2013, 28: 414-422.

Rosner et al., "Merging high-quality biochemical fractionation with a refined flow cytometry approach to monitor nucleocytoplasmic protein expression throughout the unperturbed mammalian cell cycle," Nature Protocols, Mar. 2013, 8(3):602-26.

Roucou et al., "A cytochrome c-GFP fusion is not released from mitochondria into the cytoplasm upon expression of Bax in yeast cells," FEBS letters, Apr. 14, 2000, 471(2-3):235-9.

Roushandeh et al., "Mitochondrial transplantation as a potential and novel master key for treatment of various incurable diseases," Cytotechnology, Apr. 2019, 71(2):647-63.

Rousou et al., "Opening of mitochondrial KATP channels enhances cardioprotection through the modulation of mitochondrial matrix volume, calcium accumulation, and respiration," American Journal of Physiology-Heart and Circulatory Physiology, Nov. 2004, 287:H967-H976.

Rowley et al., "Meeting lot-size challenges of manufacturing adherent cells for therapy," Bioprocess Int, Mar. 2012, 10(3), 16-22.

RU Office Action in Russian Appln. No. 2021126922, mailed on Jul. 7, 2023, 11 pages.

Rubino et al., "HmtDB, a genomic resource for mitochondrion-based human variability studies," Nucleic Acids Research, Jan. 2012, 40(D1):D1150-9.

Rudikoff et al., Single amino acid substitution altering antigen-binding specificity,: Proceedings of the National Academy of Sciences, Mar. 1, 1982, 79(6):1979-83.

Rustom et al., "Nanotubular Highways for Intercellular Organelle Transport," Science, Feb. 2004, 303: 1007-1010.

Sampaio et al., "Membrane lipidome of an epithelial cell line," Proceedings of the National Academy of Sciences, Feb. 1, 2011, 108(5):1903-7.

Sass et al., "Folding of Fumarase during Mitochondrial Import Determines its Dual Targeting in Yeast," the Journal of Biological Chemistry, Nov. 2008, 278: 45109-45116.

Schmitt et al., "A semi-automated method for isolating functionally intact mitochondria from cultured cells and tissue biopsies," Anal Biochem, Dec. 2013, 443:66-74.

Seyfried, "Cancer as a mitochondrial metabolic disease," Frontiers in Cell and Developmental Biology, Jul. 2015, 3: 43 (12 pages).

(56) References Cited

OTHER PUBLICATIONS

Shapiro et al., "Clearance and maintenance of blood nucleotide levels with adenosine triphosphate-magnesium chloride injection," Circulatory Shock, Jan. 1, 1992, 36(1):62-7.
Sharei et al., "A vector-free microfluidic platform for intracellular delivery," Proceedings of the National Academy of Sciences, Feb. 5, 2013, 110(6):2082-7.
Shin et al., "A novel biological strategy for myocardial protection by intracoronary delivery of mitochondria: safety and efficacy," JACC: Basic to Translational Science, Dec. 2019, 4(8):871-88.
Sieber et al., "A protein shuttle system to target RNA into mitochondria," Nucleic Acids Research, Aug. 1, 2011, 39(14): e96, 9 pages.
Sivitz et al., "Mitochondrial dysfunction in diabetes: from molecular mechanisms to functional significance and therapeutic opportunities," Antioxidants & Redox signaling, Feb. 15, 2010, 12(4):537-77.
Skrabanja et al., "Potential value of adenosine 5'-triphosphate (ATP) and adenosine in anaesthesia and intensive care medicine," British Journal of Anaesthesia, May 1, 2005, 94(5):556-62.
Slowinska et al., "Mitochondrial membrane potential and reactive oxygen species in liquid stored and cryopreserved turkey (Meleagris gallopavo) spermatozoa" Poultry Science, 97:3709-3717, 2018.
Soubannier et al., "A vesicular transport pathway shuttles cargo from mitochondria to lysosomes," Current Biology, Jan. 24, 2012, 22(2):135-41.
Spees et al., "Mitochondrial transfer between cells can rescue aerobic respiration," Proceedings of the National Academy of Sciences, Jan. 31, 2006, 103(5):1283-8.
Spinazzi et al., "Assessment of mitochondrial respiratory chain enzymatic activities on tissues and cultured cells," Nature Protocols, Jun. 2012, 7(6):1235-46.
Spuch et al., "Liposomes for targeted delivery of active agen+A3ts against neurodegenerative diseases (Alzheimer's disease and Parkinson's disease)," Journal of Drug Delivery, Jul. 13, 2011, vol. 2011, 13 pages.
Starkov et al., "Protein Misfolding and Cellular Stress in Disease and Aging," Measurement of Mitochondrial ROS Production, Jul. 7, 2010, 648:245-55.
Starkov, "Measurement of mitochondrial ROS production" Methods Mol Biol (2010) vol. 648, pp. 245-255.
Stephanopoulos et al., "Choosing an effective protein bioconjugation strategy," Nature Chemical Biology, Dec. 2011, 7: 876-884.
Stitt et al., "Metabolite Levels in Specific Cells and Subcellular Compartments of Plant Leaves," Methods in Enzymology, Jan. 1989, 174: 518-552.
Stojanovski et al., "Import of proteins into mitochondria," Methods in Cell Biology, Jan. 2007, 80:783-806.
Su et al., "Mitochondrial transplantation attenuates airway hyperresponsiveness by inhibition of cholinergic hyperactivity," Theranostics, May 2016;6(8): 1244-60.
Sun et al. "Systemic combined melatonin-mitochondria treatment improves acute respiratory distress syndrome in the rat," Journal of Pineal Research, 2015, 58: 137-150.
Surma et al., "An automated shotgun lipidomics platform for high throughput, comprehensive, and quantitative analysis of blood plasma intact lipids," European Journal of Lipid Science and Technology, Oct. 2015, 117(10):1540-9.
Suzuki et al., "In vivo porcine model of reperfused myocardial infarction: in situ double staining to measure precise infarct area/area at risk," Catheterization and Cardiovascular Interventions, Jan. 1, 2008, 71(1):100-7.
Templeton et al., "Improved DNA: liposome complexes for increased systemic delivery and gene expression," Nature Biotechnology, Jul. 1997, 15(7):647-52.
Thuwanut et al., "Cryopreservation of epididymal cat spermatozoa: effects of in vitro antioxidative enzymes supplementation and lipid peroxidation induction," Theriogenology, May 1, 2010, 73(8):1076-87.

Titov et al., "Complementation of mitochondrial electron transport chain by manipulation of the NAD+/NADH ratio," Science, Apr. 8, 2016, 352(6282):231-5.
Tonelli et al., "Causes and circumstances of death in pulmonary arterial hypertension," American Journal of Respiratory and Critical Care Medicine, Aug. 1, 2013, 188(3):365-9.
Toyoda et al., "Opening of Mitochondrial ATP-Sensitive Potassium Channels Enhances Cardioplegic Protection," Ann Thorac Surg, Apr. 2001, 71: 1281-9.
Treulen et al., "Cryopreservation induces mitochondrial permeability transition in a bovine sperm model," Cryobiology, Aug. 2018, 83:65-74.
Trudeau et al., "Lysosome acidification by photoactivated nanoparticles restores autophagy under lipotoxicity," Journal of Cell Biology, Jul. 4, 2016, 214(1):25-34.
Tsukube et al., Amelioration of ischemic calcium overload correlates with high-energy phosphates in senescent myocardium, Am J Physiol Heart Cir Physiol, Jul. 1997, 273: H418-H425.
Tsukube et al., "Developmental Differences in Cytosolic Calcium Accumulation Associated With Surgically Induced Global Ischemia: Optimization of Cardioplegic Protection and Mechanism of Action," the Journal of Thoracic and cardiovascular Surgery, Jul. 1996, 112: 175-184.
Uchenna Agu et al., "The lung as a route for systemic delivery of therapeutic proteins and peptides," Respiratory Research, Aug. 2001, 2(4):1-2.
Ui-Tei et al., "Sensitive assay of RNA interference in Drosophila and Chinese hamster cultured cells using firefly luciferase gene as target," FEBS Letters, Aug. 18, 2000, 479(3):79-82.
Vander Heiden et al. "Bcl-xL Regulates the Membrane Potential and Volume Homeostasis of Mitochondria" Cell, Nov. 28, 1997, 91(5):627-37.
Vander Heiden et al., "Understanding the Warburg Effect: The Metabolic Requirements of Cell Proliferation," Science, May 2009, 324: 1029-1033.
Varkouhi et al., "Endosomal escape pathways for delivery of biologicals," Journal of Controlled Release, May 2011, 151(3):220-8.
Vlieghe et al., "Synthetic therapeutic peptides: science and market," Drug Discovery Today, Jan. 1, 2010, 15(1-2):40-56.
Wakiyama et al., "Selective opening of mitochondrial ATP-sensitive potassium channels during surgically induced myocardial ischemia decreases necrosis and apoptosis," European Journal of Cardio-Thoracic Surgery, Mar. 1, 2002, 21(3):424-33.
Walter et al., "Advanced tools for the analysis of protein phosphorylation in yeast mitochondria," Analytical Biochemistry, Aug. 1, 2018, 554:23-7.
Wang et al., "Correcting human mitochondrial mutations with targeted RNA import," Proceedings of the National Academy of Sciences, Mar. 27, 2012, 109(13):4840-5.
Weber-Lotfi et al., "DNA import competence and mitochondrial genetics," Biopolymers and Cell, Jan. 2014(30)1:71-3.
Weber-Lotfi et al., "Nucleic acid import into mitochondria: new insights into the translocation pathways," Biochimica et Biophysica Acta (BBA)-Molecular Cell Research, Dec. 1, 2015, 1853(12):3165, 43 pages.
Weixler et al., "Preventing Right Heart Failure in Pressure-Overload Hypertrophy through Transplantation of Autologous Mitochondria," The Thoracic and Cardiovascular Surgeon, Jan. 2019, 67(S 01):DGTHG-V116, 1 page.
Wibom et al., "Measurement of ATP production and respiratory chain enzyme activities in mitochondria isolated from small muscle biopsy samples," Analytical Biochemistry, Dec. 15, 2002, 311(2):139-51.
Wieckowski et al., "Isolation of mitochondria-associated membranes and mitochondria from animal tissues and cells," Nat Protoc, Nov. 2009, 4:1582-1590.
Wright, "A new nebuliser," The Lancet, Jul. 1958, 272(7036):24-5.
Wu et al., "Covalent labeling of mitochondria with a photostable fluorescent thiol-reactive rhodamine-based probe," Analytical Methods, Mar. 2012, 4(6):1699-703.

(56) References Cited

OTHER PUBLICATIONS

Wu et al., "MicroRNAs direct rapid deadenylation of mRNA," Proceedings of the National Academy of Sciences, Mar. 14, 2006, 103(11):4034-9.
Yamaguchi et al., "Mitochondria frozen with trehalose retain a number of biological functions and preserve outer membrane integrity" Cell Death and Differentiation, 14:616-624, 2007.
Yin et al., "Adipocyte mitochondrial function is reduced in human obesity independent of fat cell size," The Journal of Clinical Endocrinology & Metabolism, Feb. 1, 2014, 99(2):E209-16.
Yin et al., "Non-viral vectors for gene-based therapy," Nature Reviews Genetics, Aug. 2014, 15(8):541-55.
Yu et al., "Capitalizing Resolving Power of Density Gradient Ultracentrifugation by Freezing and Precisely Slicing Centrifuged Solution: Enabling Identification of Complex Proteins from Mitochondria by Matrix Assisted Laser Desorption/Ionization Time-of-Flight Mass Spectrometry," Journal of Analytical Methods in Chemistry, 2016:1-7, 2016.
Yu et al., "Gene delivery to mitochondria by targeting modified adenoassociated virus suppresses Leber's hereditary optic neuropathy in a mouse model," Proceedings of the National Academy of Sciences, May 15, 2012, 109(20):E1238-47.
Yu et al., "Interaction between bevacizumab and murine VEGF-A: a reassessment," Investigative Ophthalmology & Visual Science, Feb. 2008, 49(2):522-7.
Zamzamiet al., "Mitochondrial permeability transition in apoptosis and necrosis," Cell Death and Differentiation, Nov. 1, 2005, 12(S2):1478.
Zeng et al., "Both natural and designed micro RNAs can inhibit the expression of cognate mRNAs when expressed in human cells," Molecular Cell, Jun. 1, 2002, 9(6):1327-33.
Zetsche et al. "Cpf1 is a single RNA-guided endonuclease of a class 2 CRISPR-Cas system," Cell, Oct. 2015, 163:759-771.
Zhao et al., "Glutathione selectively modulates the binding of platinum drugs to human copper chaperone Cox17," Biochem J, Dec. 2015, 472(2):217-23.
Zhou et al., "Progress in the Field of Constructing Near-Infrared Light-Responsive Drug Delivery Platforms," Journal of Nanoscience and Nanotechnology, Mar. 2016, 16: 2111-2125.
AU Office Action in Australian Appln. No. 2023200521, mailed on Feb. 9, 2024, 3 pages.
CA Office Action in Canadian Appln. No. 2,952,121, mailed on Oct. 31, 2023, 5 pages.
CA Office Action in Canadian Appln. No. 3,130,213, mailed on Nov. 2, 2023, 4 pages.
CN Office Action in Chinese Appln. No. 202080039304.2, mailed on Feb. 19, 2024, 12 pages (with English translation).
EP Extended European Search Report in European Appln. No. 23179249.0, mailed on Nov. 30, 2023, 10 pages.
EP Office Action in European Appln. No. 20756733.0, mailed on Dec. 5, 2023, 10 pages.
JP Office Action in Japanese Appln. No. 2021-547460, mailed on Dec. 22, 2023, 10 pages (with English translation).
kompas.com, "Dilated Cardiomyopathy," Keio University Hospital KOMPAS, Jan. 26, 2018, retrieved Jan. 17, 2024 from URL <https://kompas.hosp.keio.ac.jp/contents/000200.html>, 5 pages (with English translation).
medicalnote.Jp, "About Pulmonary Heart Disease," Sep. 11, 2018, retrieved Dec. 12, 2023 from URL <https://medicalnote.jp/diseases/肺性心>, 3 pages (English translation).
Piao et al., "Mitochondrial metabolic adaptation in right ventricular hypertrophy and failure," Journal of Molecular Medicine, Oct. 2010, 88:1011-20.
RU Office Action in Russian Appln. No. 2021126922, mailed on Nov. 14, 2023, 14 pages (with English translation).
tohoku.jp, "Elucidating the Mechanism of Pulmonary Hypertension Associated with Left Heart Failure—Identification of a Novel Drug Candidate for Heart Failure," Press Release, Graduate School of Medicine, Tohoku University, Jul. 10, 2018, retrieved Jan. 17, 2024 from URL <https://www.tohoku.ac.jp/japanese/newimg/pressimg/tohokuuniv-press20180710_Shimokawa180703_01web.pdf>, 12 pages (with English translation).
twmu.jp, "Cardiac Enlargement and Cardiac Hypertrophy," Column, Adult Medical Center, Tokyo Women's Medical University, Jun. 1, 2012, retrieved Jan. 17, 2024 from URL <http://www.twmu.ac.jp/IOG/column/file32.html>, 3 pages (English translation).
Weixler et al., "Autogenous mitochondria transplantation for treatment of right heart failure," The Journal of Thoracic and Cardiovascular Surgery, Jul. 2021, 162(1):e111-21.

\* cited by examiner

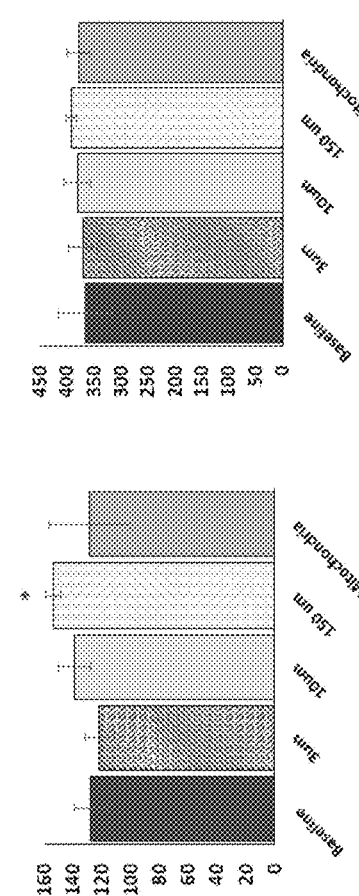
FIG. 11A
FIG. 11B
FIG. 11C
FIG. 11D
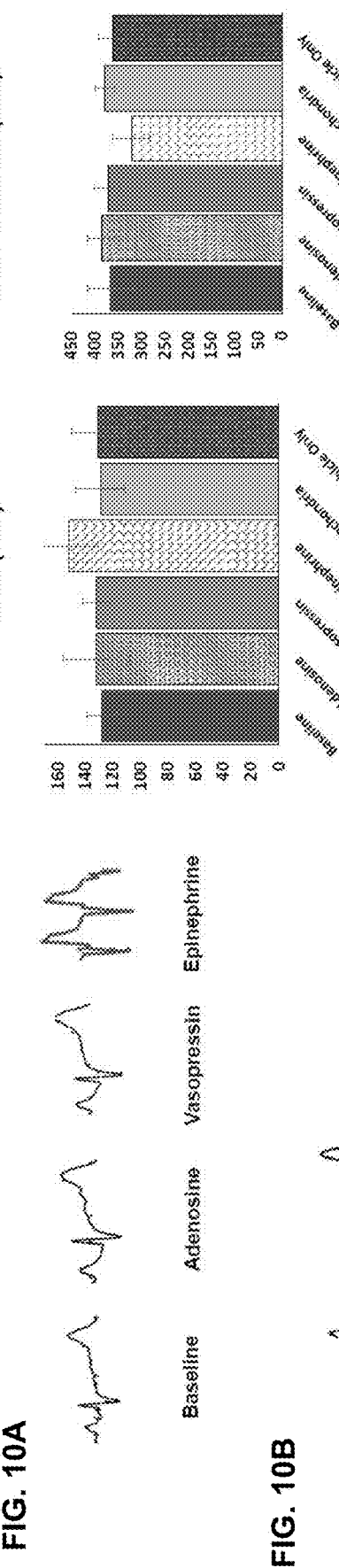
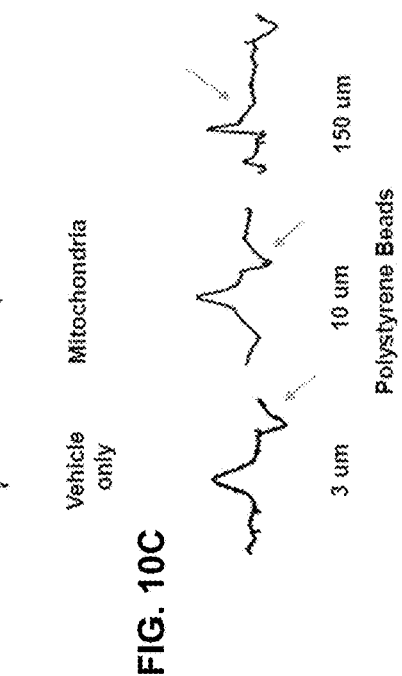
FIG. 10A
FIG. 10B
FIG. 10C

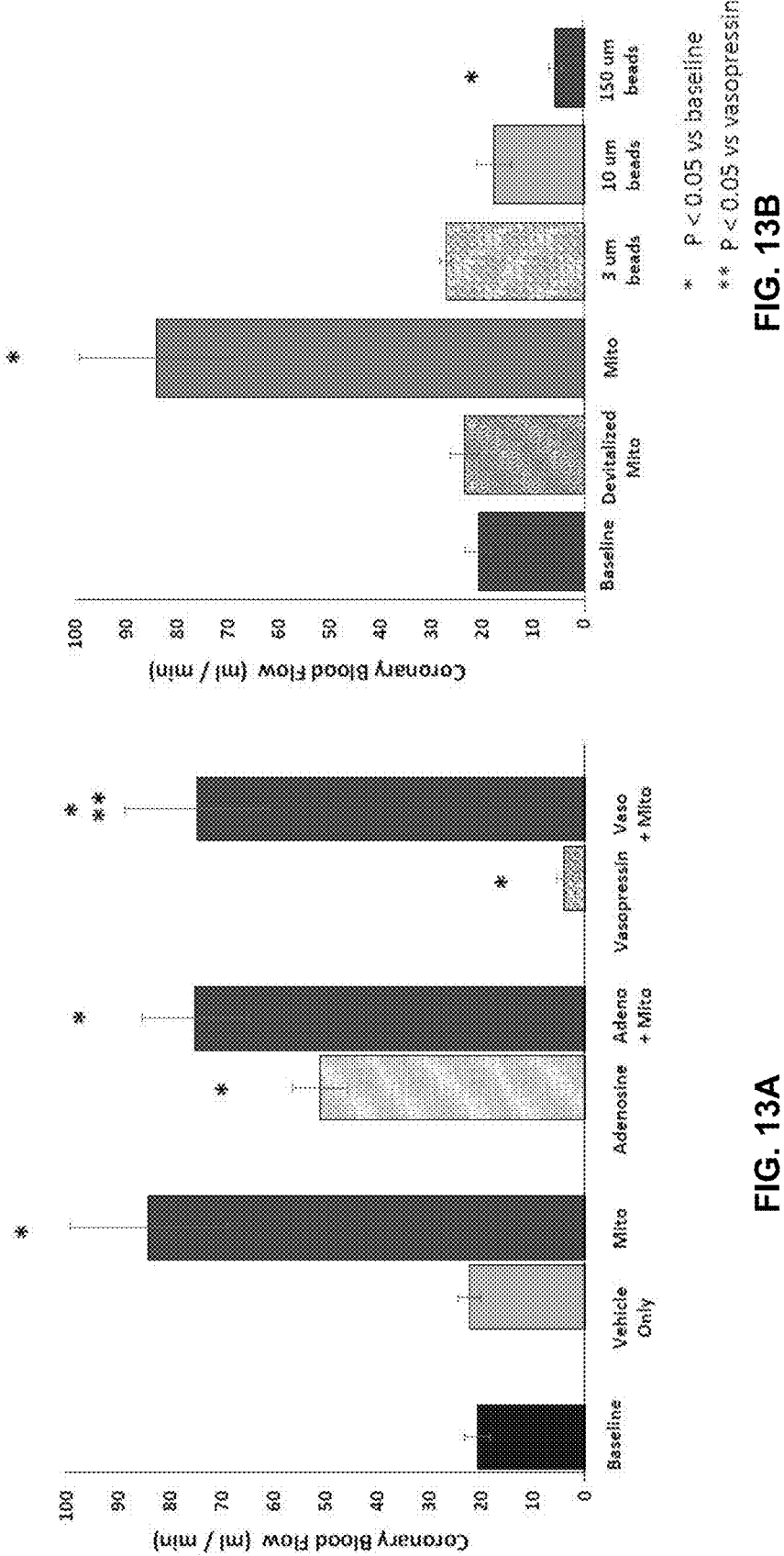

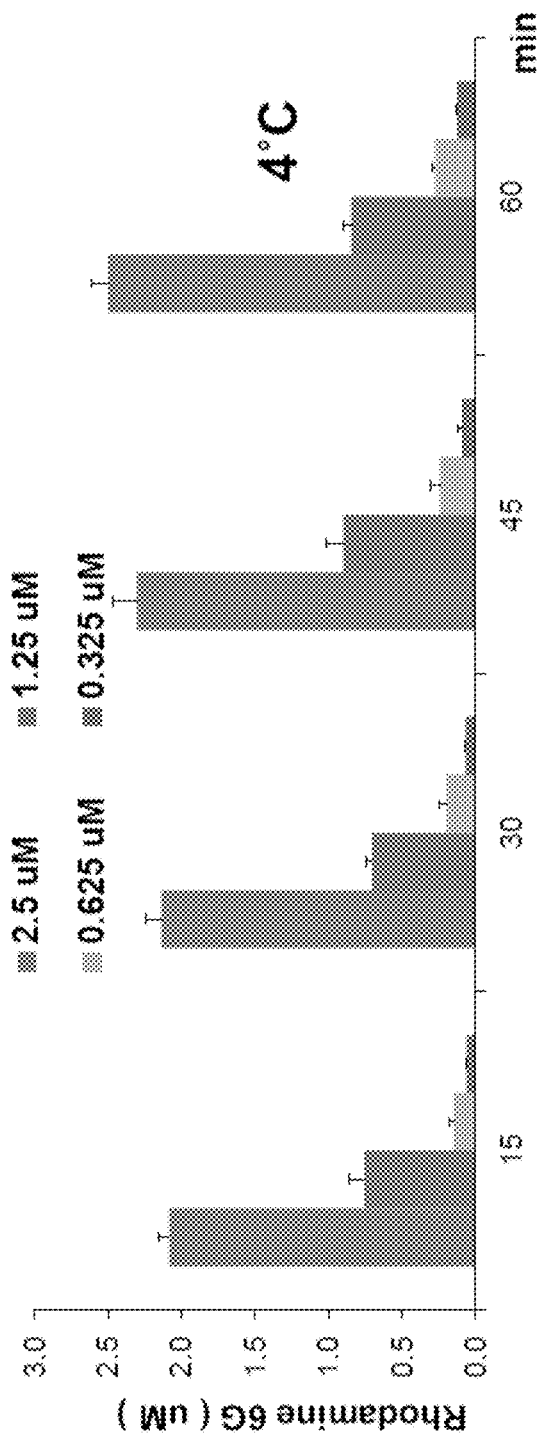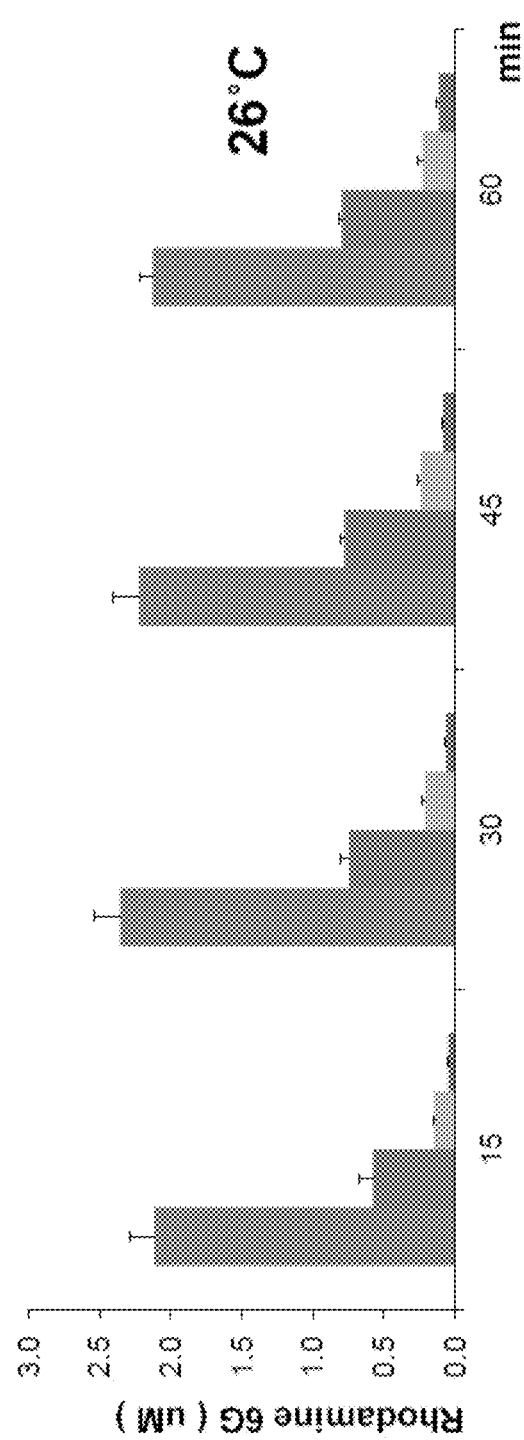
FIG. 22A
FIG. 22B

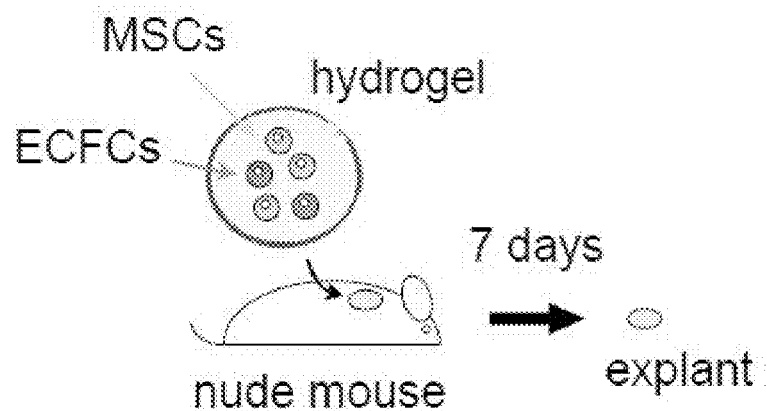
FIG. 27A
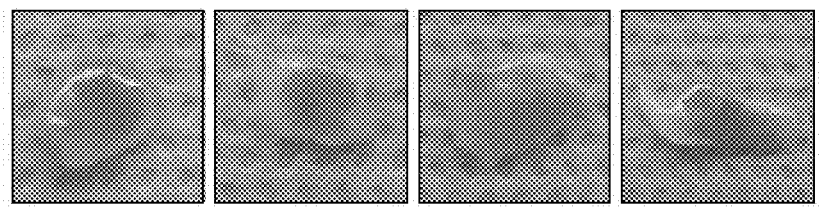
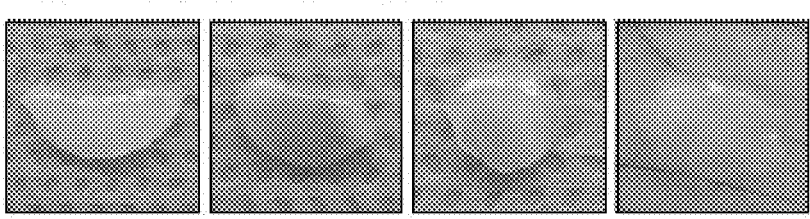
FIG. 27B

UEA-1 DAPI h-CD31 hematoxylin

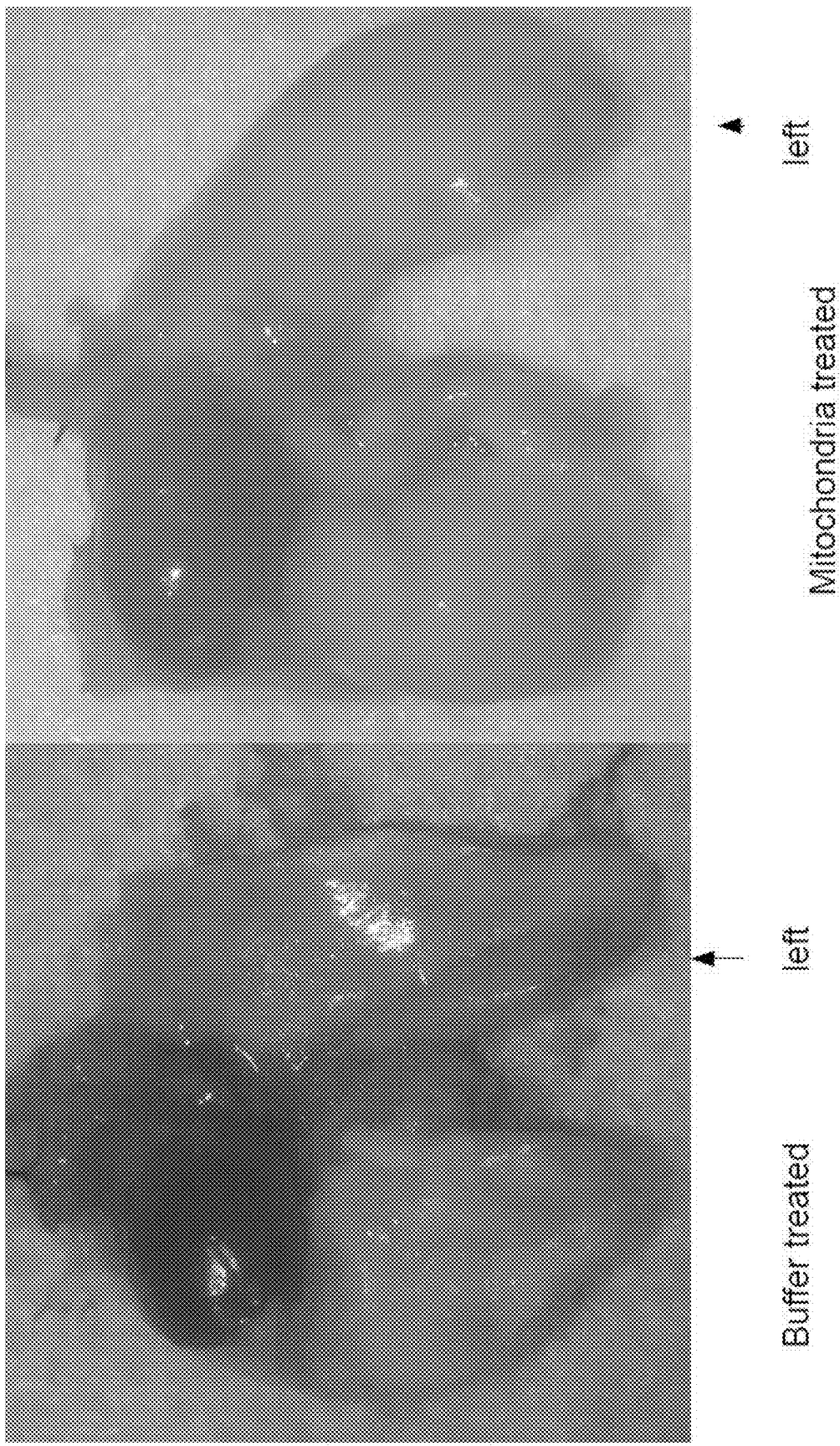
FIG. 31A  Buffer treated
FIG. 31B  Mitochondria treated

THERAPEUTIC USE OF MITOCHONDRIA AND COMBINED MITOCHONDRIAL AGENTS

CLAIM OF PRIORITY

This application is a continuation application of U.S. patent application Ser. No. 17/960,994, filed Oct. 6, 2022, which is a continuation application of U.S. patent application Ser. No. 16/451,910, filed Jun. 25, 2019, now abandoned, which is a divisional application to U.S. patent application Ser. No. 15/803,543, filed on Nov. 3, 2017, now U.S. Pat. No. 10,370,458, which claims priority under 35 USC 120 of International Application Serial No. PCT/US2017/013564, filed on Jan. 13, 2017, which claims benefit of U.S. Provisional Application Ser. No. 62/279,442, filed on Jan. 15, 2016, U.S. Provisional Application Ser. No. 62/279,489, filed on Jan. 15, 2016, and U.S. Provisional Application Ser. No. 62/420,381, filed on Nov. 10, 2016. The entire contents of the foregoing are incorporated herein by reference.

STATEMENT AS TO FEDERALLY SPONSORED RESEARCH

This invention was made with government support under Grant Numbers HL103642, HL029077, and HL068915, awarded by the National Institutes of Health. The Government has certain rights in the invention.

FIELD

The disclosure relates to therapeutic use of mitochondria and combined mitochondrial agents.

BACKGROUND

Mitochondria are double membrane-bound organelles found in the cytoplasm of nucleated eukaryotic cells. They are found in almost every cell of the human body except red blood cells. They are the cell's primary site of energy metabolism and generate adenosine triphosphate (ATP) for different cell functions. Typically, more than 90% of a cell's requirement for ATP is supplied by the cell's own mitochondria.

Mitochondria are composed of two concentric membranes, which have specialized functions. The inner mitochondrial membrane contains proteins for ATP synthase. The outer mitochondrial membrane, which contains large numbers of integral membrane proteins, encloses the entire organelle.

The structure of mitochondria has striking similarities to some modern prokaryotes. In fact, mitochondria are thought to have originated from an ancient symbiosis when a nucleated cell engulfed an aerobic prokaryote. In the symbiosis relationship, the host cell came to rely on the engulfed prokaryote for energy production, and the prokaryote cell began to rely on the protective environment provided by the host cell.

Due to mitochondria's primary function in cell metabolism, damage and dysfunction in mitochondria can cause a range of human diseases. Diseases caused by mutation in the mitochondrial DNA (mtDNA) include Kearns-Sayre syndrome, MELAS syndrome and Leber's hereditary optic neuropathy. These diseases are often transmitted by a mother to her offspring. Moreover, diseases such as Kearns-Sayre syndrome, Pearson syndrome, and progressive external ophthalmoplegia are thought to be due to large-scale mtDNA rearrangements.

Furthermore, damage and dysfunction in mitochondria can also be caused by acquired mitochondrial conditions. These acquired mitochondrial conditions may be caused by injury, toxicity, chemotherapy, and age-related changes. Particularly, ischemia/reperfusion injury can cause mitochondrial damage, which will have a negative impact on oxygen consumption and energy synthesis.

Currently, there are no known and approved treatments that involve mitochondria. There is a need for such treatment. There is also a need to utilize mitochondria for drug delivery and some other therapeutic and diagnostic purposes.

SUMMARY

The present disclosure provides pharmaceutical compositions comprising mitochondria and methods of treating disorders using such pharmaceutical compositions. The specification further provides diagnostic and imaging methods using such pharmaceutical compositions. The described methods are based, at least in part, on the discovery that isolated mitochondria themselves, and isolated mitochondria linked to a therapeutic agent, diagnostic agent and/or imaging agent, can be delivered to a patient's tissue by injecting them into the patient's blood vessels. That is, direct injection or application of mitochondria to the target tissue, while contemplated by certain methods described herein, is not always necessary. Rather, in some instances, methods described herein take advantage of the discovery that after mitochondria are injected or infused, for example, into an artery, the mitochondria can transverse the artery wall and be taken up by cells of the patient's tissues. Methods described herein can provide localized and general distribution of mitochondria or mitochondria with therapeutic, diagnostic, and/or imaging agents to tissues or cells for a variety of treatment, diagnostic, and/or imaging purposes using relatively simple medical procedures.

In one aspect, the disclosure relates to methods of treating a subject having an ischemia-related disease. The methods include the step of administering a therapeutically effective amount of a composition comprising isolated mitochondria, or a composition comprising a combined mitochondrial agent to the subject, e.g., by direct injection, by vascular infusion, and/or by injecting the composition into the blood vessel of the subject. The ischemia-related disease can be any disease that involves ischemia, e.g., an acute coronary syndrome, a myocardial infarction, a liver ischemia-reperfusion injury, or an ischemic injury-compartmental syndrome.

The combined mitochondrial agent can include a pharmaceutical, diagnostic, imaging, or therapeutic agent, or any other agent. The imaging agent can be radioactive, fluorescent, or any agent that is detectable by magnetic resonance imaging (MRI), e.g., $^{18}F$-Rhodamine 6G or iron oxide nanoparticle.

In certain embodiments, the blood vessel is the blood vessel or part of the vascular system which carries the blood to the target site, the target organ, or the target area, e.g., the coronary artery of the subject, the hepatic portal vein of the subject, the greater pancreatic artery of the subject, or the prostate artery of the subject.

In certain embodiments, the mitochondria can have different sources, e.g., the mitochondria can be autogeneic, allogeneic, or xenogeneic. In certain embodiments, the autogeneic mitochondria can have exogenous mtDNA. In some embodiments, the mitochondria are from a subject's first-degree relative.

In some embodiments, the described methods include the step of collecting the isolated mitochondria from cells prior to administration. The isolated mitochondria or combined mitochondrial agent can be administered to the subject immediately after the isolated mitochondria are collected from cells.

In another aspect, the disclosure relates to methods of minimizing cardiotoxicity from chemotherapy. The methods include the steps of administering to a subject prior to (e.g., immediately prior to), during, or following the subject's treatment with chemotherapy, a therapeutically effective amount of a pharmaceutical composition comprising isolated mitochondria or a combined mitochondrial agent. The composition can be administered to the subject by various routes, e.g., by direct injection, by vascular infusion, or by injecting the composition into the blood vessel of the subject. The combined mitochondrial agent can further comprise a pharmaceutical agent. In certain embodiments, the blood vessel is the coronary artery of the subject.

In still another aspect, the disclosure relates to methods of delivering an agent to a target site of a subject. The methods include the step of administering a therapeutically effective amount of a combined mitochondrial agent into a blood vessel of the subject. The target site can be any part of the subject, e.g., heart, kidney, pancreas, lung, optic nerve, brain, or skeletal muscle. In these methods, the blood vessel is part of the vascular system of the subject that carries blood to the target site. The delivered agent can be a pharmaceutical, diagnostic, imaging, or therapeutic agent, an antibody or an antigen binding fragment, or any other agent. The agent and the mitochondria are in physical contact with each other, e.g., the agent can be linked to mitochondria, e.g., by a covalent bond, embedded in the mitochondria, attached to mitochondria, embedded in the mitochondrial membrane, substantially enclosed within a mitochondrion, or encapsulated entirely by mitochondria.

In yet another aspect, the disclosure relates to methods of imaging tissue of a subject. The methods include the steps of administering an effective amount of a combined mitochondrial agent to the subject, wherein the combined mitochondrial agent comprises an imaging agent; and imaging the tissue of the subject by an imaging technique. The imaging agent can be radioactive, fluorescent, or any agent that is detectable by MRI, e.g., $^{18}$F-Rhodamine 6G or iron oxide nanoparticle. The imaging technique can be, for example, positron emission tomography (PET), computed tomography (CT), micro-computed tomography (µCT), PET/CT, PET/MRI, fluorescence molecular tomography (FMT), or FMT/CT.

In one aspect, the disclosure relates to methods of making a combined mitochondrial agent. The methods include the steps of isolating mitochondria from cells, and mixing the mitochondria with an effective amount of therapeutic agent, diagnostic agent or imaging agent, under conditions sufficient to allow linkage of the therapeutic agent, diagnostic agent, or imaging agent, to the mitochondria. In some embodiments, the mitochondria are mixed with an imaging agent, and the imaging agent can be $^{18}$F-Rhodamine 6G or iron oxide nanoparticle.

In another aspect, the disclosure relates to methods of making a pharmaceutical agent comprising a combined mitochondrial agent. The methods include the steps of providing a combined mitochondrial agent, and mixing the combined mitochondrial agent with a pharmaceutically acceptable carrier, e.g. water, saline, and respiration buffer.

In still another aspect, the disclosure relates to methods of treating a subject having a mitochondrial dysfunction disorder, e.g., Kearns-Sayre syndrome, MERRF syndrome, MELAS syndrome, Leber's disease, Barth Syndrome, diabetes, or Parkinson's disease. In these methods, a therapeutically effective amount of a pharmaceutical composition comprising isolated mitochondria or a combined mitochondrial agent is administered to the subject, e.g., by direct injection, by vascular infusion, or by injecting the composition into the blood vessel of the subject. The combined mitochondrial agent can further include a pharmaceutical agent.

In certain embodiments of methods described herein, the blood vessel is the blood vessel or part of the vascular system which carries the blood to the target site, the target organ, or the target area, e.g., the coronary artery of the subject, the hepatic portal vein of the subject, the greater pancreatic artery of the subject, or the prostate artery of the subject.

In certain embodiments of methods described herein, the mitochondria can have different sources, e.g., the mitochondria can be autogeneic, allogeneic, or xenogeneic. In certain embodiments, the autogeneic mitochondria can have exogenous mtDNA. In some embodiments, the mitochondria are from a subject's first-degree relative.

In some embodiments, the described methods include the step of collecting the isolated mitochondria from cells prior to administration. The isolated mitochondria or combined mitochondrial agent can be administered to the subject immediately after the isolated mitochondria are collected from cells.

In yet another aspect, the disclosure relates to methods of minimizing cardiotoxicity from chemotherapy, comprising administering a therapeutically effective amount of a pharmaceutical composition comprising isolated mitochondria and/or a combined mitochondrial agent into a blood vessel of the subject. The combined mitochondrial agent can further comprise a pharmaceutical agent. In certain embodiments, the blood vessel is the coronary artery of the subject. In some instances, the subject can be treated before, during, and/or after chemotherapy treatment.

In one aspect, the disclosure relates to methods of minimizing reperfusion damage of an organ. The methods include the steps of injecting an effective amount of isolated mitochondria or combined mitochondrial agent into a blood vessel of the organ prior to (e.g., immediately prior to), during, and/or following reperfusion damage occurring in the organ. In some embodiments, the organ is treated in situ or ex vivo. The isolated mitochondria and/or combined mitochondrial agents can be injected to the organ by various routes, e.g., by direct injection, by vascular infusion, and/or by injecting the composition into the blood vessel of the organ. In some instances, the organ is an organ that requires high energy production, e.g., a brain, a heart, a kidney, a liver. In some other instances, the organ is a transplanted organ, e.g., a transplanted heart, a transplanted kidney, and a transplanted liver.

In another aspect, the disclosure relates to methods of treating a cancer in a subject. The cancer can be any type of cancer, e.g., lung, brain, pancreatic, melanoma, prostate, ovary, colon cancer. In some cases, the cancer is a neuroblastoma (e.g., a pediatric neuroblastoma). The methods include the step of administering a therapeutically effective amount of a combined mitochondrial agent into a blood vessel of the subject having cancer. The combined mitochondrial agent can include a cytotoxic agent, a cytostatic agent, a growth inhibitor, or a CSF-1 inhibitor, etc.

In still another aspect, the disclosure relates to methods of treating a mitochondrial defect in a cell, comprising obtaining an effective number of mitochondria from a subject, and contacting the cell with an effective number of mitochondria. The cell can be any cell that has a mitochondrial defect, e.g., an egg cell or an embryo cell prepared during in vitro fertilization. The subject can be a male, e.g., a man who provides sperms for in vitro fertilization.

In another aspect, the disclosure relates to methods of improving mitochondrial function in a cell. The methods include the steps of contacting the cell with isolated mitochondria and/or a combined mitochondrial agent in an amount sufficient to improve mitochondrial function. The cell can be any type of cells known to a skilled practitioner, e.g., a stem cell.

In yet another aspect, the disclosure relates to methods of improving mitochondrial function in a tissue of a subject. The methods include the steps of administering to the tissue a composition comprising isolated mitochondria and/or a combined mitochondrial agent in an amount sufficient to improve mitochondrial function in the tissue. The tissue can be any type of tissue, e.g., skin tissue, facial muscle, bone marrow tissue, or white adipose tissue. In some embodiments, the composition is administered to the tissue by injecting the composition into the tissue.

The disclosure also provides methods of increasing blood flow or decreasing vascular resistance in an organ of a subject. The methods include the steps of administering a composition comprising isolated mitochondria and/or a combined mitochondrial agent to the subject in an amount sufficient to increase blood flow or decrease vascular resistance. The organ can be any organ, e.g., heart, lung, kidney, brain, or skeletal muscle. In some embodiments, the isolated mitochondria or combined mitochondrial agent are administered to the subject within about 30 minutes, 40 minutes, 50 minutes, or 60 minutes after the time point when mitochondria isolation process starts. In addition, the composition can be injected into a coronary artery before, during, or after a heart surgery. In some cases, the composition is administered to the subject by injecting the composition into a blood vessel, wherein the blood vessel carries blood to the organ.

In one aspect, the disclosure provides methods of removing a blockage in a blood vessel of a subject. The methods include the steps of injecting a composition comprising isolated mitochondria and/or a combined mitochondrial agent into the blood vessel. In some cases, the subject has a peripheral vascular disease. The composition is injected into the blood vessel within about 30 minutes, 40 minutes, 50 minutes, or 60 minutes after the time point when mitochondria isolation process starts.

In another aspect, the disclosure provides methods of transplanting a cell or a tissue to a subject. The methods include the steps of contacting the cell or the tissue with an effective amount of a composition comprising isolated mitochondria and/or an isolated mitochondrial agent; and transplanting the cell or the tissue to the subject. The cell can be any type of cell, e.g., a stem cell, and the tissue can be any type of tissue, e.g., bone marrow tissue.

In yet another aspect, the disclosure relates to methods of improving mitochondrial function in a cell or a tissue. The methods include the steps of contacting the cell or the tissue with an effective amount of a composition comprising isolated mitochondria and/or a combined mitochondrial agent. In some cases, the cell is a transplanted cell, or a stem cell. In some other cases, the tissue is a transplanted tissue or bone marrow tissue.

The disclosure also provides methods of treating a wound in a subject, the method comprising administering a composition comprising isolated mitochondria and/or a combined mitochondrial agent to the wound area in an amount sufficient to treat the wound. The wound can be any kind of wound, e.g., an open wound, or a burn wound. In some cases, the composition is administered by injecting the composition into the wound tissue.

The disclosure also relates to methods of treating a subject having a metabolic disorder. The methods include the steps of administering a composition comprising isolated mitochondria and/or a combined mitochondrial agent into white adipose tissue of the subject in an amount sufficient to treat the metabolic disorder. In some embodiments, the metabolic disorder is obesity or type II diabetes. The composition can be administered by injecting the composition into the white adipose tissue.

In one aspect, the disclosure provides methods of increasing mitochondrial function in white adipose tissue of a subject. The methods include the steps of administering a composition comprising isolated mitochondria or a combined mitochondrial agent into the white adipose tissue in an amount sufficient to increase mitochondrial function. In some embodiments, the composition is administered by injecting the composition into the white adipose tissue.

In yet another aspect, the disclosure provides methods of decreasing fat deposit in a subject. The methods include the steps of administering a composition comprising isolated mitochondria or a combined mitochondrial agent to the fat deposit in an amount sufficient to decrease fat deposit in the subject. In some embodiments, the fat tissue is white adipose tissue.

The fat issue can be located at various places in the body, e.g., under the chin or in the abdomen of the subject.

The disclosure also provides methods of treating (e.g., reducing the appearance of) skin wrinkles or scars on a subject. The methods include the steps of administering a composition comprising isolated mitochondria and/or a combined mitochondrial agent to the skin wrinkle or scar area on the subject in an amount sufficient to treat (e.g., reduce the appearance of) skin wrinkles or scars. In some embodiments, the composition is administered by a Gauge 28, 29, 30, 31, 32, 33, or 34 hypodermic needle.

The disclosure also relates to methods of improving mitochondrial function in skin of a subject. The methods include the steps of administering a composition comprising isolated mitochondria and/or a combined mitochondrial agent to the subject in an amount sufficient to improve mitochondrial function in the skin of the subject. In some embodiments, the composition is administered by injecting the composition into skin tissue. The composition can be administered by a hypodermic needle, e.g., a Gauge 28, 29, 30, 31, 32, 33, or 34 hypodermic needle.

In one aspect, the disclosure provides compositions comprising isolated mitochondria and/or a combined mitochondrial agent; and a carrier. In some embodiments, the composition is a pharmaceutical composition. The carrier can be any suitable carrier, e.g., respiration buffer, mitochondria buffer, sterile mitochondria buffer, University of Wisconsin (UW) solution, blood, serum, or a contrast agent.

In yet another aspect, the disclosure provides methods of improving transplanted cell or transplanted tissue integration. The methods include the steps of contacting the transplanted cell or transplanted tissue with a composition comprising isolated mitochondria or combined mitochondrial agents in an amount sufficient to improve transplanted cell or transplanted tissue integration.

In all methods and/or compositions described herein, the combined mitochondrial agent can comprise a pharmaceutical agent. The pharmaceutical agent can be a therapeutic agent, an imaging agent, a diagnostic agent, or any combination thereof. The imaging agent can be radioactive. In some embodiments, the imaging agent is $^{18}$F-Rhodamine 6G, or iron oxide nanoparticle. In some embodiments, the pharmaceutical agent is linked to mitochondria by a covalent bond. Alternatively, or in addition, the pharmaceutical agent is embedded in the mitochondria. A combined mitochondrial agent can include an antibody or an antigen binding fragment. Furthermore, in all methods and/or compositions described herein, the mitochondria can be autogeneic, allogeneic, or xenogeneic. In some embodiments, the mitochondria have exogenous DNA (e.g., mtDNA).

As used herein, the term "isolated mitochondria" means functional and intact mitochondria that are free of extraneous eukaryotic cell material.

A "combined mitochondrial agent" is an isolated mitochondrion that is combined artificially with a pharmaceutical, diagnostic, or imaging, or any other agent. The agent is combined with a mitochondrion in any fashion, for example, linked (e.g., chemically or electrostatically linked) to a mitochondrion, attached to a mitochondrion, embedded in the mitochondrial membrane, substantially enclosed within a mitochondrion, or encapsulated entirely by a mitochondrion, as long as the mitochondrion and the agent are in physical contact with each other. Combined mitochondrial agents are designed such that the mitochondrion act as a "carrier" that can transport the agent to a patient's tissues after injection.

The terms "subject" and "patient" are used throughout the specification to describe an animal, human or non-human, to whom treatment according to the methods of the present disclosure is provided. Veterinary applications are clearly anticipated by the present disclosure. The term includes but is not limited to birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs.

The term "treat(ment)," is used herein to denote delaying the onset of, inhibiting, alleviating the effects of, or prolonging the life of a patient suffering from, a condition, e.g., a disease described herein.

An "ischemia-related disease" is a disease that involves ischemia. Ischemia, as used herein, is a reduced blood flow to an organ and/or tissue. The reduced blood flow may be caused by any suitable mechanism, including a partial or complete blockage (an obstruction), a narrowing (a constriction), and/or a leak/rupture, among others, of one or more blood vessels that supply blood to the organ and/or tissue.

By "immediately after mitochondria are collected from cells" is meant immediately after mitochondria are collected from cells and before any substantial reduction in viability of the mitochondria can occur.

As used herein, the term "transplantation" is used throughout the specification as a general term to describe the process of implanting an organ, tissue, mass of cells, individual cells, or cell organelles into a recipient. The term "cell transplantation" is used throughout the specification as a general term to describe the process of transferring at least one cell, e.g., an islet cell, or a stem cell, to a recipient. For example, such transplantation can be performed by removing the β-cells (or intact islets) from a donor's pancreas and putting them into a recipient patient whose pancreas cannot produce sufficient insulin. The terms include all categories of transplants known in the art, except blood transfusions. Transplants are categorized by site and genetic relationship between donor and recipient. The term includes, e.g., autotransplantation (removal and transfer of cells or tissue from one location on a patient to the same or another location on the same subject), allotransplantation (transplantation between members of the same species), and xenotransplantation (transplantations between members of different species).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 10A is an electrocardiogram (ECG) tracing graph showing the baseline ECG, and the ECG after the swine model is treated with adenosine, vasopressin, and epinephrine.

FIG. 10B is an ECG tracing graph showing the ECG after the swine model is treated with vehicles and mitochondria.

FIG. 10C is an ECG tracing graph showing the ECG after the swine model is treated with 3 um, 10 um and 150 um polystyrene beads.

FIG. 11A is a bar graph showing the baseline QRS, and the QRS after the swine model is treated with adenosine, vasopressin, epinephrine, mitochondria, and vehicles.

FIG. 11B is a bar graph showing the baseline corrected QT (cQT) interval, and the cQT interval after the swine model is treated with adenosine, vasopressin, epinephrine, mitochondria, and vehicles.

FIG. 11C is a bar graph showing the baseline QRS, and the QRS after the swine model is treated with 3 um, 10 um and 150 um polystyrene beads and mitochondria.

FIG. 11D is a bar graph showing the baseline cQT interval, and the cQT interval after the swine model is treated with 3 um, 10 um and 150 um polystyrene beads and mitochondria.

FIG. 13A is a bar graph showing coronary blood flow after coronary infusion of vehicles, adenosine, vasopressin, and mitochondria.

FIG. 13B is a bar graph showing coronary blood flow after coronary infusion of mitochondria, devitalized mitochondria, and 3 um, 10 um and 150 um polystyrene beads.

FIG. 22A is a bar graph showing Rhodamine 6G concentration in the unbound fraction under different incubating conditions (4° C.).

FIG. 22B is a bar graph showing Rhodamine 6G concentration in the unbound fraction under different incubating conditions (26° C.).

FIG. 27A is a schematic diagram showing in vivo vasculogenesis assay.

FIG. 27B is a set of macroscopic images showing explants harvested 7 days after transplantation.

FIG. 31A is a photo showing lung ischemia/reperfusion injury without mitochondria treatment.

FIG. 31B is a photo showing lung ischemia/reperfusion injury with mitochondria treatment.

DETAILED DESCRIPTION

Figure 1:
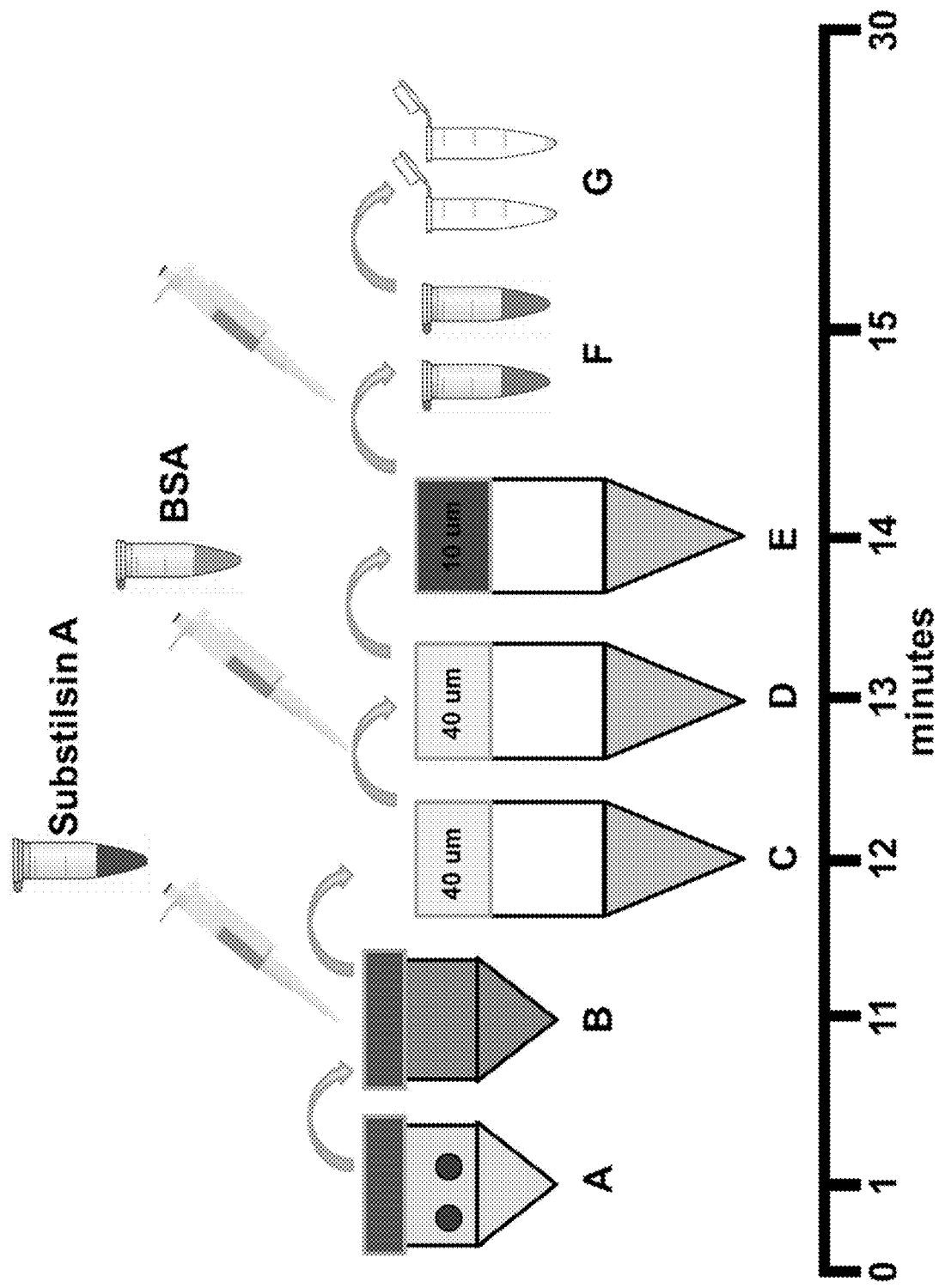
FIG. 1 is a schematic diagram of one exemplary protocol for isolating mitochondria from tissue or cultured cells.

The present invention is based, at least in part, on the discovery that isolated mitochondria, and isolated mitochondria linked to a therapeutic agent, diagnostic agent and/or imaging agent, can be delivered to a patient's tissue by injecting them into the patient's blood vessels. Skilled practitioners can locally and/or generally distribute mitochondria to tissues and/or cells of a patient for a variety of purposes, using relatively simple medical procedures. Further, mitochondria can be used as carrier agents, e.g., to deliver therapeutic, diagnostic, and/or imaging agents, to a patient's tissues. Compared to some traditional therapeutic regimens that involve nanoparticles, it is further noted that mitochondria are not toxic and do not cause any substantial adverse immune or auto-immune response.

While not intending to be bound by any theory, it is believed that infused mitochondria extravasate through the capillary wall by first adhering to the endothelium. After they are injected or infused into an artery, mitochondria can cross the endothelium of the blood vessels and be taken up by tissue cells through an endosomal actin-dependent internalization process.

Combined Mitochondrial Agents

Combined mitochondrial agents include mitochondria that are physically associated with an agent, such as a therapeutic agent, a diagnostic agent, and/or an imaging agent.

A therapeutic agent can be any agent that has a therapeutic or prophylactic use. Exemplary therapeutic agents include, e.g., therapeutic agents for ischemia-related disorders, cytotoxic agents for treating cancer, among many others. In some instances, mitochondria can deliver therapeutic agents to specific cells, for example, tumor cells. The therapeutic agent may be, e.g., an intracellular inhibitor, deactivator, toxin, arresting substance and/or cytostatic/cytotoxic substance that, once inside a cell, inhibits, destroys, arrests, modifies and/or alters the cell such that it can no longer function normally and/or survive. The therapeutic agent can be an agent to restore a cell's proper function, for example, a DNA vector for gene therapy. A therapeutic agent can be, e.g., an inorganic or organic compound; a small molecule (less than 500 daltons) or a large molecule; a proteinaceous molecule, such as a peptide, polypeptide, protein, post-translationally modified protein, or antibody; or a nucleic acid molecule, such as a double-stranded DNA, single-stranded DNA, double-stranded RNA, single-stranded RNA, or a triple helix nucleic acid molecule. In some embodiments, a therapeutic agent can be a natural product derived from any known organism (e.g., from an animal, plant, bacterium, fungus, protist, or virus) or from a library of synthetic molecules. In some embodiments, a therapeutic agent can be a monomeric or a polymeric compound. Some exemplary therapeutic agents include cytotoxic agents, DNA vectors, small interfering RNAs (siRNA), micro RNAs (miRNA), reactive peptides, nanoparticles, microspheres, and fluorescent molecules.

A diagnostic agent is an agent that has diagnostic use. As mitochondria carry a diagnostic agent into a cell, in some embodiments, the diagnostic agent can be designed to determine the condition within a cell, for example pH and oxidative stress within a cell.

An imaging agent is an agent that is employed for use in imaging techniques. The techniques or modalities include, but are not limited to, X-rays, computed tomography (CT), magnetic resonance imaging (MRI), scintigraphy, fluorescence, ultrasound, etc. The imaging agent can be florescent and/or radioactive. In some embodiments, an imaging agent can also be a diagnostic agent. Exemplary imaging agents include, but are not limited to, MitoTracker fluorophores (Thermo Fisher Scientific Inc.), CellLight® RFP, BacMam 2.0 (Thermo Fisher Scientific Inc.), pH-sensitive pHrodo fluorescent dyes (Thermo Fisher Scientific Inc.), $^{18}$F-Rhodamine 6G, $^{18}$F-labeled rhodamine B, magnetic iron oxide nanoparticles, and gold- and platinum-based nanoparticles.

As discussed above, a combined mitochondrial agent comprises a mitochondria and an agent that are in direct and/or indirect physical contact with each other. For example, an agent can be linked to mitochondria, attached to mitochondria, embedded in the mitochondrial membrane, or completely or partially enclosed in mitochondria. In some instances, a pharmaceutical agent can be linked to mitochondria covalently. In some instances, the agent is linked to constituents of mitochondrial membrane directly through a covalent bond (e.g., a carboxamide bond and a disulfide bond), or indirectly through a linker (e.g., a peptide linker) or another covalently bonded agent. In other instances, an agent can be linked to mitochondria non-covalently, for example, through hydrophobic interaction, Van der Waals interaction, and/or electrostatic interaction, etc.

In some embodiments, a combined mitochondrial agent can comprise two or more different types of agents, for example, two different kinds of therapeutic agents, three different kinds of imaging agents, one therapeutic agent and one imaging agent, a therapeutic agent and a diagnostic agent, etc. Skilled practitioner will appreciate that any variation is possible.

One particularly useful linker to link mitochondria and an agent provides a sustained release of the agent upon injection. This can be accomplished, for example, using a hydrazone functional group. For example, a hydrazone is formed to covalently bind an agent to constituents on the mitochondrial membrane. Once this combined mitochondrial agent is taken up by cells, the change in pH will result in hydrolysis of the hydrazone, releasing the bound agent inside the cell.

In some embodiments, a therapeutic agent, a diagnostic agent, and/or an imaging agent can be linked to the outer mitochondrial membrane using functionalized surface chemistry. In some cases, heterobifunctional chemistries can link a therapeutic agent, a diagnostic agent, and/or an imaging agent to the mitochondrial surface, and once they are internalized, these agents can be released through interactions with intercellular esterases (e.g. via interaction with an acetoxymethyl ester) or through a UV-light activation or Near-Infrared light activation strategy. The UV-light activation and Near-Infrared light activation strategies are described, e.g., in Zhou, Fang, Hanjie Wang, and Jin Chang, "Progress in the Field of Constructing Near-Infrared Light-Responsive Drug Delivery Platforms," Journal of Nanoscience and Nanotechnology 16.3 (2016): 2111-2125; Bansal, Akshaya, and Yong Zhang, "Photocontrolled nanoparticle delivery systems for biomedical applications," Accounts of chemical research 47.10 (2014): 3052-3060; Barhoumi, Aoune, Qian Liu, and Daniel S. Kohane, "Ultraviolet light-mediated drug delivery: Principles, applications, and challenges," Journal of Controlled Release 219 (2015): 31-42. Each of them is incorporated by reference in its entirety.

Pharmaceutical and Other Compositions

The disclosure provides compositions that comprise isolated mitochondria, compositions that comprise combined mitochondrial agents, compositions that comprise both isolated mitochondria and combined mitochondrial agents, and methods of using such compositions.

A pharmaceutical composition described herein may include mitochondria and/or combined mitochondria agents and a pharmaceutically acceptable carrier. As used herein, the language "pharmaceutically acceptable carrier" includes saline, solvents, dispersion media, coatings, antibacterial and antifungal agents, isotonic and absorption delaying agents, and the like, compatible with pharmaceutical administration. In some embodiments, the pharmaceutically acceptable carrier is phosphate buffered saline, saline, Krebs buffer, Tyrode's solution, contrast media, or omnipaque, or a mixture thereof. In some embodiments, the pharmaceutically acceptable carrier is sterile mitochondria buffer (300 mM sucrose; 10 mM K+-HEPES (potassium buffered (4-(2-hydroxyethyl)-1-piperazineethanesulfonic acid, pH 7.2); 1 mM K+-EGTA, (potassium buffered ethylene glycol tetraacetic acid, pH 8.0)). In some embodiments, the pharmaceutically acceptable carrier is respiration buffer (250 mM sucrose, 2 mM $KH_2PO_4$, 10 mM $MgCl_2$, 20 mM K-HEPES Buffer (pH 7.2), and 0.5 mM K-EGTA (pH 8.0)).

Pharmaceutical compositions are typically formulated to be compatible with its intended route of administration. Examples of routes of administration include parenteral, e.g., intravenous, intradermal, subcutaneous, oral (e.g., inhalation), sublingual, transdermal (e.g., topical), transmucosal, and rectal administration.

A pharmaceutical composition can be formulated for various clinical uses, e.g., imaging, treating wounds, treating injuries, preserving organs, improving mitochondrial functions in organs or tissues, and skin care. In some cases, the pharmaceutically acceptable carrier is a contrast agent for imaging purpose. In some embodiments, the pharmaceutical composition may include antiseptic agents, antibacterial agents (e.g., antibiotics), antifungal agents, disinfectants, analgesic agents, anesthetic agents, steroids, nutritional supplements, ethereal oils, etc. An anesthetic agent is a drug that can prevent pain during surgery or treatment. Exemplary analgesic agents include, without limitation, paracetamol, nonsteroid anti-inflammatory drugs, salicylates, ibuprofen and lidocaine. Exemplary antibacterial agents include, without limitation, dichlorobenzyl alcohol, amylmetacresol and antibiotics. Exemplary antibiotics include penicillins carbapenems, cephalosporins aminoglycosides, bacitracin, gramicidin, mupirocin, chloramphenicol, thiamphenicol, lincomycin, clindamycin, macrolides, novobiocin, polymyxins, rifamycins, spectinomycin, tetracyclines, vancomycin, teicoplanin, streptogramins, anti-folate agents, sulfonamides, trimethoprim, pyrimethamine, nitrofurans, methenamine mandelate, methenamine hippurate, nitroimidazoles, quinolones, fluoroquinolones, isoniazid, ethambutol, pyrazinamide, para-aminosalicylic acid, cycloserine, capreomycin, ethionamide, prothionamide, thiacetazone and viomycin. Antiseptic agents are antimicrobial substances that can be applied to living tissue/skin to reduce the possibility of infection, sepsis, or putrefaction. Exemplary antiseptics include, without limitation, chlorhexidine and salts thereof, benzalkonium and salts thereof, triclosan and cetylpyridium chloride. Exemplary antifungal agents include, without limitation, tolnaftate, miconazole, fluconazole, clotrimazole, econazole, ketoconazole, itraconazole, terbinafine, amphotericin, nystatin and natamycin. Exemplary steroids include, without limitation, prednisone acetate, prednisone valerate, prednisolone, alclometasone dipropionate, fluocinolone acetonide, dexamethasone, methylprednisolone, desonide, pivolate, clocortolone pivolate, triamcinolone acetonide, prednicarbate, fluticasone propionate, flurandrenolide, mometasone furoate, desoximetasone, betamethasone, betamethasone dipropionate, betamethasone valerate, betamethasone propionate, betamethasone benzoate, diflorasone diacetate, fluocinonide, halcinonide, amcinonide, halobetasol propionate, and clobetasol propionate. Exemplary nutritional supplements include, without limitation, vitamins, minerals, herbal products and amino acids. Vitamins include without limitation, vitamin A, those in the vitamin B family, vitamin C, those in the vitamin D family, vitamin E and vitamin K. Ethereal oils include without limitation, those derived from mint, sage, fir, lavender, basil, lemon, juniper, rosemary, eucalyptus, marigold, chamomile, orange and the like. Many of these agents are described, e.g., in WO 2008152626, which is incorporated by reference in its entirety.

Compositions comprising mitochondria and/or combined mitochondrial agents can be formulated in any form, e.g., liquids, semi-solids, or solids. Exemplary compositions include liquids, creams, ointments, salves, oils, emulsions, liposome formulations, among others.

Compositions for Transplantation

Isolated mitochondria or combined mitochondrial agents can be included in compositions that are designed for use in organ, tissue, or cell transplantation. The composition may include isolated mitochondria and/or combined mitochondrial agents and a liquid that is suitable for administration to patients and/or organs in situ or ex vivo, e.g., for maintaining organs, tissues or cells ex vivo. In general, the liquid will be an aqueous solution. Examples of solutions include Phosphate Buffered Saline (PBS), Celsior™ solution, Perfadex™ solution, Collins solution, citrate solution, tissue culture media (e.g., Dulbecco's Modified Eagle's Medium (DMEM)), the Histidine-tryptophan-ketoglutarate (HTK) solution, and the University of Wisconsin (UW) solution (Oxford Textbook of Surgery, Morris and Malt, Eds., Oxford University Press, 1994).

The University of Wisconsin cold storage solution is considered a standard solution for organ transplantation. It includes the following: 100 mM potassium lactobionate, 25 mM $KH_2PO_4$, 5 mM $MgSO_4$, 30 mM raffinose, 5 mM adenosine, 3 mM glutathione, 1 mM allopurinol, and 50 g/L hydroxyethyl starch. Isolated mitochondria or combined mitochondrial agents can be added to these liquids for organ, tissue and cell preservation.

Blood Products

Mitochondria and/or combined mitochondrial agents can be included in compositions that include blood and/or or products derived from blood. In some embodiments, the composition can include mitochondria and/or mitochondrial agents and blood, e.g., whole blood, serum, one or more individual blood components, and/or an artificial blood substitute. In some cases, these blood products can be administered to a subject, and the mitochondria in the blood products can improve the mitochondrial function in the subject. For example, such blood products can be administered to a patient as a part of a blood transfusion procedure. As is art-known, blood or blood products can be stored in any number of vessels, e.g., in blood bags, ampules, and/or vials.

Skin and Cosmetic Compositions

Isolated mitochondria and/or combined mitochondrial agents can be included in compositions that can be applied (e.g., topically and/or by injection) to the skin and/or to wounds (e.g., burns, small cuts, larger lacerations, necrotic regions, regions damaged by infection with bacteria, fungi, or viruses, or areas with damage caused by inflammation, e.g., rashes), wrinkles, or scars, in the skin. The composition can also include any known agents that can be used in skin or cosmetic products, e.g., abrasive agents, antiseptic agents, antibacterial agents (e.g., antibiotics), antifungal agents, disinfectants, analgesic agents, anesthetic agents, steroids, nutritional supplements, and/or ethereal oils.

Skilled practitioners will appreciate that for a topical composition, e.g., a composition such as a liquid, cream, lotion, ointment, or oil, an abrasive agent can be added to the composition to aid in delivery of mitochondria and/or combined mitochondrial agents to underlying layers of skin cells upon application (e.g., as the composition is rubbed into and/or smeared onto the skin). An abrasive agent is a material that is used to wear away part of the tissue (e.g., damaged or dead skin cells) by friction. Compositions that include an abrasive agent and isolated mitochondria or combined mitochondrial agents can be used for various purposes, e.g., cosmetic use, treating wounds, etc. Some abrasive agents are described, e.g., in U.S. Pat. Nos. 5,830,445, 2,561,043, 4,279,890, each of which is incorporated by reference in its entirety. Skilled practitioners will also appreciate that any art-known agent or composition that aids in transportation of a compound into underlying skin layers and/or pores of the skin may be useful in such embodiments and may be included in, or applied to a patient separately but in conjunction with, a composition comprising mitochondria and/or mitochondrial agents.

Methods of Making Compositions Comprising Mitochondria and/or Combined Mitochondrial Agents Isolating Mitochondria Mitochondria for use in the presently described methods can be isolated or provided from any source, e.g., isolated from cultured cells or tissues. Exemplary cells include, but are not limited to, muscle tissue cells, cardiac fibroblasts, cultured cells, HeLa cells, prostate cancer cells, yeast, among others, and any mixture thereof. Exemplary tissues include, but are not limited to, liver tissue, skeletal muscle, heart, brain, and adipose tissue. Mitochondria can be isolated from cells of an autogenous source, an allogeneic source, and/or a xenogeneic source. In some instances, mitochondria are isolated from cells with a genetic modification, e.g., cells with modified mtDNA or modified nuclear DNA.

Mitochondria can be isolated from cells or tissues by any means known to those of skill in the art. In one example, tissue samples or cell samples are collected and then homogenized. Following homogenization, mitochondria are isolated by repetitive centrifugation. Alternatively, the cell homogenate can be filtered through nylon mesh filters. Typical methods of isolating mitochondria are described, for example, in McCully J D, Cowan D B, Pacak C A, Toumpoulis I K, Dayalan H and Levitsky S, Injection of isolated mitochondria during early reperfusion for cardioprotection, Am J Physiol 296, H94-H105. PMC2637784 (2009); Frezza, C., Cipolat, S., & Scorrano, L, Organelle isolation: functional mitochondria from mouse liver, muscle and cultured filroblasts. Nature protocols, 2(2), 287-295 (2007); and a PCT application entitled "Products and Methods to Isolate Mitochondria" (PCT/US2015/035584; WO 2015192020); each of which is incorporated by reference.

Methods of Making Combined Mitochondrial Agents

Skilled practitioners will appreciate that an agent can be linked to mitochondria in any number of ways, e.g., by attaching to mitochondria, embedding partially or completely in the mitochondrial membrane, enclosing in mitochondria, or encapsulating within the mitochondria.

While not intending to be bound by any theory or any particular approach, it is believed that the outer membrane of mitochondria is adherent and thus particularly amenable to combination with various agents. In some embodiments, pharmaceutical agents can be attached to the outer membrane of mitochondria simply by incubation. For example, an effective amount of pharmaceutic agents can be fully mixed with isolated mitochondria in a buffer, e.g., respiration buffer, at a temperature favorable to isolated mitochondria, e.g., from 0° C. to 26° C., from 0° C. to 4° C., or about 0° C., 4° C., 26° C. This procedure is useful to attach an effective amount of pharmaceutic agents (e.g., nanoparticles, DNA vectors, RNA vectors) to mitochondria.

In some embodiments, organic cations (e.g., rhodamine and tetramethylrosamine) are readily sequestered by functioning mitochondria because of the electric potential on mitochondrial membrane. Healthy mitochondrial membranes maintain a difference in electric potential between the interior and exterior of the organelle, referred to as the membrane potential. This membrane potential is a direct result of mitochondrial functional processes, and can be lost if the mitochondria are not working properly. Lipid-soluble cations are sequestered by mitochondria as a consequence of their positive charge and of their solubility in both the inner membrane lipids and the matrix aqueous space. Similarly, in some other embodiments, anions can be attached to the outer membrane of mitochondria because of its negative charge. To link mitochondria with these pharmaceutical agents, an effective amount of pharmaceutic agents should be fully mixed with isolated mitochondria in a buffer, e.g., respiration buffer, at a temperature favorable to isolated mitochondria, e.g., about 0° C. or 4° C.

The therapeutic, diagnostic, and/or imaging agent can be linked to phospholipids, peptides, or proteins on the mitochondrial membrane through a chemical bond. For example, molecules including fluorophores (pHrodo Red (Thermo Fisher Scientific, Inc.)) and metallic particles (e.g., 30 nm magnetic iron oxide nanoparticles (Sigma)) can be covalently linked to exposed amine groups on proteins and peptides exposed on the outside membrane of intact mitochondria using succinimidyl ester conjugates. These reactive reagents react with non-protonated aliphatic amine groups, including the amine terminus of proteins and the c-amino group of lysine residues, which creates a stable carboxamide bond. In another example, when the pharmaceutic agent, e.g., MitoTracker® Orange CMTMRos (Invitrogen, Carlsbad, CA, now Thermo-Fisher Scientific, Cambridge, MA), are mixed with functional mitochondria, they are oxidized and then react with thiols on proteins and peptides on mitochondria to form conjugates.

There are numerous reactive chemical moieties available for attaching therapeutic, diagnostic, and/or imaging agents to the surface of mitochondria (e.g. carboxylic acid, amine functionalized, etc.).

Agents can be attached via protein bonding, amine bonding or other attachment methods either to the outer or inner mitochondrial membrane. Alternatively, or in addition, an agent can be attached to the mitochondria membrane through hydrophobic interaction, Van der Waals interaction, and/or electrostatic interaction.

In many instances, therapeutic agents, diagnostic agents and imaging agents may simply be mixed with isolated mitochondria, and incubated in a buffer (e.g., respiration buffer) for a sufficient period of time (e.g., a few minutes, 5 minutes, 10 minutes, or 1 hour) at favorable conditions (e.g., from 0° C. to 26° C., from 0° C. to 4° C., or about 0° C., 4° C., 26° C., pH 7.2~8.0).

Exemplary methods of preparing combined mitochondrial agents are described in McCully et al, Injection of isolated mitochondria during early reperfusion for cardioprotection, Am J Physiol 296, H94-H105. PMC2637784 (2009); and Masuzawa et al, Transplantation of autologously derived mitochondria protects the heart from ischemia-reperfusion injury, Am J Physiol 304, H966-982. PMC3625892 (2013). Each of the foregoing are incorporated by reference in its entirety.

Methods of Preparing Compositions Comprising Mitochondria and/or Combined Mitochondrial Agents Isolated mitochondria and combined mitochondrial agents can be mixed with a pharmaceutically acceptable carrier to make a pharmaceutic composition. A pharmaceutically acceptable carrier includes any compound or composition useful in facilitating storage, stability, administration, cell targeting and/or delivery of the mitochondria and/or combined mitochondrial agent, including, without limitation, suitable vehicles, diluents, solvents, excipients, pH modifiers, salts, colorants, rheology modifiers, lubricants, coatings, fillers, antifoaming agents, polymers, hydrogels, surfactants, emulsifiers, adjuvants, preservatives, phospholipids, fatty acids, mono-, di- and tri-glycerides and derivatives thereof, waxes, oils and water. In some embodiments, isolated mitochondria and/or the combined mitochondrial agents are suspended in water, saline, buffer, respiration buffer, or sterile mitochondria buffer for delivery in vivo. Pharmaceutically acceptable salts, buffers or buffer systems, including, without limitation, saline, phosphate buffer, phosphate buffered saline (PBS) or respiration buffer can be included in a composition described herein. Vehicles having the ability to facilitate delivery to a cell in vivo, such as liposomes, may be utilized to facilitate delivery of the combined mitochondrial agents to the target cells.

Methods of making compositions, e.g., liquid, semi-solid, and solid compositions (e.g., liquids, creams, lotions, ointments, oils, among others), are well-known in the art. Skilled practitioners will appreciate that such known methods can be modified to add one or more steps to add mitochondria and/or combined mitochondrial agents and form a composition described herein. Skilled practitioners will appreciate that in some instances a composition described herein may include more than one type of combined mitochondrial agent. For example, included are compositions comprising mitochondria wherein essentially each mitochondrion is associated with multiple types of agents. Also included are compositions comprising mitochondria wherein each mitochondrion is paired with only one type of agent but wherein the composition comprises a mixture of mitochondria/agent pairings.

Methods of Use

Administration

Isolated mitochondria and combined mitochondrial agents can be administered to a patient by injection intravenously, intra-arterially, intraperitoneally, intra-muscularly, and/or through intraosseous infusion. In some embodiments, isolated mitochondria and combined mitochondrial agents, can be delivered by direct injection or by vascular infusion.

Once mitochondria are injected into a tissue, mitochondria will be taken up by cells around the site of injection. Therefore, in some embodiments, the site of injection is the target site. In some other embodiments, mitochondria are injected to a blood vessel which carries the blood to the target site, for example, an organ, a tissue, or an injured site. While not intending to be bound by any theory, evidence suggests that mitochondria delivered by direct injection are internalized by cells through actin-dependent endocytosis. However, mitochondrial uptake by vascular delivery appears to be more complicated. The rapid and widespread uptake of mitochondria when delivered by vascular infusion would suggest that mechanisms allowing for the rapid passage of mitochondria through the vascular wall are involved. Some studies support the concept that cells can routinely escape from the circulation. It has been shown that certain cardiac and mesenchymal stem cells appear to be actively expelled from the vasculature in a process different from diapedesis (Cheng, K., Shen, D., Xie, Y., Cingolani, E., Malliaras, K., Marbán, E., 2012, Brief report: Mechanism of extravasation of infused stem cells. Stem Cells. 30, 2835-2842.; Allen, T. A., Gracieux, D., Talib, M., Tokarz, D. A., Hensley, M. T., Cores, J., Vandergriff, A., Tang, J., de Andrade, J. B., Dinh, P. U., Yoder, J. A., Cheng, K., 2017. Angiopellosis as an Alternative Mechanism of Cell Extravasation. Stem Cells. 35, 170-180). Transmigration of stem cells through the vascular wall requires extensive remodeling of the endothelium. Mitochondria may use a similar remodeling mechanism to pass through the vascular wall. Another possible mechanism for mitochondrial uptake may be diapedesis-like. Some cells routinely escape from the circulation. For example, leukocyte extravasation (i.e. diapedesis) between venous endothelial cells is a well-understood process that involves cell adhesion proteins. Further, it is also possible that infused mitochondria extravasate through the capillary wall through the space between the endothelium cells. After mitochondria cross the endothelium of the blood vessels, mitochondria are taken up by tissue cells through an endosomal actin-dependent internalization process.

Mitochondria or combined mitochondrial agents can be administered to a subject as a singular, one-time treatment, or alternatively, multiple treatments, e.g., a treatment course that continues intermittently or continuously for about 1, 2, 5, 8, 10, 20, 30, 50, or 60 days, one year, indefinitely, or until a physician determines that administration of the mitochondria or combined mitochondrial agent is no longer necessary.

In one method of administration, mitochondria or combined mitochondrial agents are injected into organ tissue directly. The injection is repeated several times at different sites of the organ. In such a method, a sterile 1-ml insulin syringe with a small needle (e.g., 28-gauge) can be used for the injection and each injection site can receive, e.g., about $1.2 \times 10^6$ of mitochondria.

Skilled practitioners will appreciate that the amount of mitochondria and/or combined mitochondrial agents, e.g., compositions comprising mitochondria and/or combined mitochondrial agents, that should be administered to a patient will vary depending upon, e.g., the type of disorder being treated, the route of administration, the duration of the treatment, the size of an area to be treated, and/or the location of the treatment site in the patent, among others. Skilled practitioners will be able to determine dosages to be administered depending on these and other variables. For example, a total of about $1 \times 10^7$ of mitochondria can be administered into a blood vessel of a subject, e.g., to treat localized ischemia in the myocardium. As another example, in the case of larger organs or affected areas, greater numbers of mitochondria, e.g., $1 \times 10^{10}$ to $1 \times 10^{14}$ mitochondria, can be injected into the blood vessel. Conversely, in the case of small focal lesions, $1 \times 10^3$ to $1 \times 10^6$ mitochondria can be infused into the patient. Therefore, an effective amount of mitochondria or combined mitochondrial agents (or compositions comprising same) is the total amount of mitochondria or combined mitochondrial agents sufficient to bring about a desired therapeutic effect. An effective amount can be, e.g., at least or about $1 \times 10^2$ mitochondria or combined mitochondrial agents e.g., from about $1 \times 10^3$ to about $1 \times 10^{14}$, about $1 \times 10^4$ to about $1 \times 10^{13}$, about $1 \times 10^5$ to about $1 \times 10^{12}$, about $1 \times 10^6$ to about $1 \times 10^{11}$, about $1 \times 10^7$ to about $1 \times 10^{10}$, about $1 \times 10^3$ to about $1 \times 10^7$, about $1 \times 10^4$ to about $1 \times 10^6$, about $1 \times 10^7$ to about $1 \times 10^{14}$, or about $1 \times 10^8$ to about $1 \times 10^{13}$, about $1 \times 10^9$ to about $1 \times 10^{12}$, about $1 \times 10^5$ to about $1 \times 10^8$ or at least or about $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, or at least or about $1 \times 10^{14}$, or e.g., an amount more than $1 \times 10^{14}$. As used herein, the term "total amount" in the context of administration to a patient can refer to the total amount of mitochondria or combined mitochondrial agents in a single administration (e.g., one injection, one dose administered in an infusion) or in multiple administrations (e.g., multiple injections), depending on the dosing regimen being performed.

Isolated mitochondria and/or combined mitochondrial agents can be administered to a subject every 12-24 hours by various routes, e.g., direct injection, vascular delivery. In some embodiments, isolated mitochondria or combined mitochondrial agents can be administered to a subject every 5-10 minutes (e.g., every 5 minutes, every 10 minutes) by various routes, e.g., direct injection, vascular infusion.

In some embodiments, isolated mitochondria or combined mitochondrial agents can be directly injected into tissues or organs by Gauge 24, 25, 26, 27, 28, 29, 30, 31, 32, 33, and 34 needles. In some other cases, isolated mitochondria, or combined mitochondrial agents can be delivered to a target site by a catheter.

It is noted that in some cases, the effects of mitochondria depend on the length of the time period between the time of isolation and the time of use. Thus, in some instances, the mitochondria are freshly isolated and viable. The mitochondria or combined mitochondrial agents can be administered to a subject within about 5 minutes, about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes after the mitochondria are isolated. In some instances, the mitochondria or combined mitochondrial agents are administered to a subject within about 5 minutes, about minutes, about 20 minutes, about 30 minutes, about 40 minutes, about 50 minutes, about minutes, about 70 minutes, about 80 minutes, about 90 minutes, about 100 minutes, about 110 minutes, about 120 minutes after starting the mitochondria isolating process. Mitochondria and/or combined mitochondrial agents may in some instances be stored for a short period of time (e.g., about 10 minutes, about 20 minutes, about 30 minutes, about 40 minutes, about 50 minutes, or about 60 minutes) before use.

It is also noted that, in some cases, frozen-thawed mitochondria are not viable and not effective for certain treatments described herein, e.g., treatment of ischemia/reperfusion injuries. Thus, in some cases, the mitochondria are not frozen and thawed after isolation from tissues and/or cells.

The mitochondria for the treatment can be isolated from cells or tissues of an autogenous source, an allogeneic source, and a xenogeneic source. In some instances, mitochondria are collected from cultured cells or tissues of a subject, and these mitochondria are administered back to the same subject. In some other cases, mitochondria are collected from cultured cells or tissues of a second subject, and these mitochondria are administered to a first subject. In some cases, mitochondria are collected from cultured cells or tissues from a different species (e.g., mice, swine, yeast).

Treating Ischemic Heart and Other Ischemia-Related Diseases

The heart is a highly energetic organ that requires a continuous supply of oxygen to maintain normal function. Under aerobic conditions, the heart derives its energy primarily from the mitochondria, which constitute 30% of the total myocardial cell volume. Following the onset of ischemia, there is a rapid decline in high-energy phosphate levels with alterations in mitochondrial structure, volume, oxygen consumption, and ATP synthesis.

Attempts to lessen myocardial tissue necrosis and improve post-ischemic function using pharmacological and/or exogenous substrate interventions, either alone or in combination with procedural techniques, have provided only limited cardioprotection. Despite these interventions, mitochondrial damage and dysfunction continue to represent major problems following myocardial ischemia and remain significant causes of morbidity and mortality.

Mitochondrial damage occurs mainly during ischemia rather than during reperfusion, and that preservation of mitochondrial respiratory function enhances contractile recovery and decreases myocardial infarct size.

Methods described herein can be used to treat ischemic heart. For example, an effective amount of isolated mitochondria can be injected into the blood vessel of a subject, for example, the coronary vasculature of the subject. For example, about $1 \times 10^7$ of mitochondria can be administered into the coronary vasculature of the subject. The injected mitochondria are internalized by cardiomyocytes after transplantation and provide enhanced oxygen consumption, upregulate chemokines that enhance post-infarct cardiac function, and upregulate the expression of protein pathways that are important in preserving myocardial energetics. In another example, an effective amount of mitochondria can be directly injected to the area at risk (regional ischemic area). The injection can be repeated several times at different sites of the heart.

Reperfusion injury is the tissue damage by blood supply when blood returns to the tissue after a period of ischemia or lack of oxygen. The absence of oxygen and nutrients during the ischemic period results in inflammation and oxidative damage when blood flow is restored. The inflammatory response further leads to the reperfusion injury in the tissue. Therefore, in some instances, a treatment also involves administering immune suppressors to the patient. The immune suppressors can be, e.g., administrated separately, but as a concurrent treatment with the mitochondrial agent. Alternatively, or in addition, the immune suppressors can be linked to mitochondria to form a combined mitochondrial agent, which can be used for the treatment. Particularly useful immune suppressors are bisphosphonates.

The ischemia/reperfusion injury in some other organs is often associated with mitochondrial damage and dysfunction as well. These organs include, but are not limited to, lung, kidney, liver, skeletal muscle, brain, etc. These injuries or diseases include, but are not limited to, ischemic colitis, mesenteric ischemia, brain ischemia, stroke, acute limb ischemia, cyanosis and gangrene. The described method can be also employed to treat ischemia injury in these organs/tissues. For these treatments, the isolated mitochondria and/or combined mitochondrial agent can be directly injected to the organ tissue or injected into the blood vessel which carries the blood to the target organ/tissue or the injured site of the subject.

Vasodilation and Blood Flow

It has been demonstrated that mitochondrial delivery by vascular infusion significantly increases coronary blood flow without altering mean blood pressure or heart rate. The ability to increase blood flow with no increase in heart rate allows for clinical usage in angina type injury and in ischemia/reperfusion related injury and in tissue damage areas where increased blood flow and oxygen delivery would be needed. Thus, the methods described herein can be used in coronary artery interventions to remove clots or obstructions in blood vessels.

Methods described herein can also be used to increase blood flow and/or oxygen delivery for various organs or tissues (e.g., heart, lung, kidney, brain, skeletal muscle). In some instances, methods described herein can be used to treat peripheral vascular disease. Peripheral vascular disease (PVD) is a blood circulation disorder that causes the blood vessels outside of the heart and brain to narrow, block, or spasm. This can happen in the arteries or veins. PVD typically causes pain and fatigue, often in the legs, and especially during exercise. Isolated mitochondria and/or combined mitochondrial agents can be injected to a blood vessel. Blood flow may carry isolated mitochondria or combined mitochondrial agents to the target site. In some instances, methods described herein can also be used to enhance smooth muscle function.

Methods described herein can also be used for vascular dilatation in various organs. In some instances, the isolated mitochondria or combined mitochondrial agents can be used to decrease vascular resistance in an organ (e.g., heart, kidney, liver, or lung). Isolated mitochondria or combined mitochondrial agents can be used to increased blood flow for angiography. The isolated mitochondria and/or combined mitochondrial agents can be added to a contrast agent, and can be used in the identification and removal of blockages.

Methods described herein can be used to treating blocked blood vessel. The methods involve, e.g., the steps of localizing blood clots, positioning a first catheter with cage distal to clot, positioning a second catheter proximal to clot, injecting mitochondria and/or combined mitochondrial agents via the proximal catheter to cause vasodilatation, collecting the clot in a basket, and removing the clot.

It is noted that the effects of vascular infusion of mitochondria are dependent on time from isolation to time of use. The vasodilatory effects decreases as time from isolation is extended. While not intending to be bound by any theory, it is hypothesized that freshly isolated mitochondria have certain chemicals, which can increase blood flow. Therefore, in some methods, the mitochondria are freshly isolated and viable. For example, the mitochondria or combined mitochondrial agents are administered to a subject within about 5 minutes, about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes after the time point when the mitochondria isolation process starts or after the mitochondria are isolated. In some cases, the mitochondria or combined mitochondrial agents are administered to a subject within about 20 minutes to about 60 minutes (e.g., about 20 minutes, about 30 minutes, about 40 minutes, about 50 minutes, about 60 minutes) after the time point when the mitochondria isolation process starts or after the mitochondria are isolated.

In some cases, increasing blood flow is not desirable (e.g., treating ischemia/reperfusion in lungs). In these cases, mitochondria or combined mitochondrial agents can be stored for a short period of time (e.g., from about 30 to about 60 minutes) before usage. This method can be used to increase tissue viability (e.g., treating ischemia/reperfusion injury) without causing an increase in blood flow. In these cases, the mitochondria or combined mitochondrial agents are administered to a subject at least 60 about minutes (e.g., about 65 minutes, about 70 minutes, about 80 minutes, about 90 minutes, about 100 minutes, about 110 minutes, about 120 minutes) after the time point when the mitochondria isolation process starts or after the mitochondria are isolated.

Heart Surgery

The isolated mitochondria and/or combined mitochondrial agents can be delivered to the heart to decrease stunning and allow for weaning of the heart from a surgical procedure (e.g., cardioplegia), and recovery of the heart without increasing heart rate or oxygen demands in the heart. In some embodiments, the methods involve direct injection of isolated mitochondria and/or combined mitochondrial agents to the heart. In some methods, isolated mitochondria and/or combined mitochondrial agents are injected into a coronary artery.

Imaging

Imaging agents can be attached to mitochondria, often by co-incubation of the mitochondria with the imaging agents. Such imaging agents include, but are not limited to, MitoTracker and pHrodo fluorophores from Thermo Fisher Scientific Inc., $^{18}$F-Rhodamine 6G, and iron oxide nanoparticles.

Combined mitochondrial agents that include an imaging agent can be injected into the tissue or perfused through the blood vessels. Tissues containing the labeled mitochondria can be examined using imaging techniques, such as positron emission tomopgrahy (PET), microcomputed tomography (XT), and magnetic resonance imaging (MRI), brightfield microscope, and 3-D super-resolution microscopy, etc. Skilled practitioners will appreciate that other imaging techniques or modalities may be used. They include, but are not limited to, x-rays, scintigraphy, fluorescence and ultrasound.

Positron emission tomography is an imaging technique that produces a three-dimensional image in the body, and can be used in methods described herein. The system detects pairs of gamma rays emitted indirectly by a positron-emitting radioisotope (tracer). Three-dimensional images of tracer concentration within the body are then constructed by computer analysis. Useful reporter groups include radioactive isotopes, such as $^{11}$C, $^{13}$N, $^{15}$O, $^{18}$F, $^{64}$Cu, $^{68}$Ga, $^{81}$mKr, $^{82}$Rb, $^{86}$Y, $^{89}$Zr, $^{111}$In, $^{123}$I, $^{124}$I, $^{133}$Xe, $^{201}$Tl, $^{125}$I, $^{35}$S, $^{14}$C, $^{3}$H. In some methods, mitochondria can be labeled by radioactive isotopes, e.g., $^{18}$F, or by molecules that incorporate radioactive isotopes, e.g., $^{18}$F-Rhodamine 6G, $^{18}$F-labeled rhodamine B. After the mitochondria are internalized by target cells, the PET imaging technique, or similar technique, can be employed to view the target cells.

Magnetic resonance imaging is a medical imaging technique to image the anatomy and the physiological processes of the body and can be used in methods described herein. In some instances, it can be used in conjugation with some other imaging techniques, for example, PET. Images acquired from both devices can be taken sequentially, in the same session, and combined into a single superposed (co-registered) image. PET/MRI scans can be used to diagnose a health condition in humans and animals, e.g., for research, medical, and agricultural purposes.

Micro-computed tomography uses x-rays to create cross-sections of a physical object that can be used to recreate a virtual model without destroying the original object, and can be used in methods described herein. In some instances, it is used in conjugation with some other imaging techniques, for example, PET. Images acquired from both devices can be taken sequentially, in the same session, and combined into a single superposed (co-registered) image. Thus, functional imaging obtained by PET, which depicts the spatial distribution of metabolic or biochemical activity in the body can be more precisely aligned or correlated with anatomic imaging obtained by CT scanning. Two- and three-dimensional image reconstruction may be rendered as a function of a common software and control system.

3D-structured illumination microscopy, 3D-SIM, or 3-D super-resolution microscopy, allows complete 3D visualization of structures inside cells and can be used in the methods described herein. Structured illumination microscopy is an imaging method capable of doubling the spatial resolution of conventional widefield fluorescence microscopy by using spatially structured illumination light. It enhances spatial resolution by collecting information from frequency space outside the observable region.

The described methods, i.e., methods that include administering mitochondria and/or combined mitochondrial agents, are useful for diagnosing a variety of diseases, such as cancers, (e.g., lung, brain, pancreatic, melanoma, prostate, colon cancers), cardiovascular disease (e.g., myocardial infarction, atherosclerosis), autoimmune diseases (e.g., multiple sclerosis, diabetes, irritable bowel syndrome, Celiac disease, Crohn's disease), and inflammatory disease.

Methods using agents for imaging purpose are well-known in the art and described in, for example, Bartholoma M D, He H, Pacak C A, Dunning P, Fahey F H, McGowan F X, Cowan D B, Treves S T and Packard A B, Biological characterization of F18-labeled Rhodamine B, a potential positron emission tomography perfusion tracer, Nucl Med Biol 40, 1043-1048, PMC3820364 (2013); Bartholomä M D, Zhang S, Akurathi V, Pacak C A, Dunning P, Fahey F H, Cowan D B, Treves S T and Packard A B, $^{18}$F-labeled rhodamines as potential myocardial perfusion agents: comparison of pharmacokinetic properties of several rhodamines, Nucl Med Biol 42, 796-803, PMC4567415 (2015); and Pacak C A, Hammer P E, MacKay A A, Dowd R P, Wang K R, Masuzawa A, Sill B, McCully J D and Cowan D B, Superparamagnetic iron oxide nanoparticles function as a long-term, multi-modal imaging label for non-invasive tracking of implanted progenitor cells, PLoS ONE 9, e108695, PMC4177390 (2014). Each of the foregoing can be useful in methods described herein and is incorporated herein by reference its entirety.

Drug Delivery

The present specification provides methods to deliver pharmaceutic agents, e.g., to cells and/or tissues of a patient. Mitochondria are taken up by tissue cells through an actin-dependent internalization process, thereby providing a way to deliver pharmaceutic agents directly into the cells. Moreover, because combined mitochondrial agents are more likely to cross the endothelium of the blood vessels near the injection site, in some instances, combined mitochondrial agents can be injected into a blood vessel that carries blood to the target site. In some instances, combined mitochondrial agents enter into tissue through the endothelium of capillaries.

An antibody or an antigen-binding fragment can be linked or attached to mitochondria. Skilled practitioners will appreciate that linking the antibody or antigen binding fragment to mitochondria or combined mitochondrial agent can allow the mitochondria or combined mitochondrial agent to be targeted to specific sites, e.g., to target cells and/or tissues. In some instances, the antibody or the antigen-binding fragment are designed to target specific cell types, for example, smooth muscle cells in lung, immune cells, macrophages, etc.

Gene Therapy

Gene therapy is the therapeutic delivery of nucleic acid polymers into a patient's cells as a drug to treat disease. Isolated mitochondria can be used as a carrier to deliver nucleic acid polymers into a cell. In some instances, combined mitochondrial agents that include nucleic acid polymers can be administered to a subject to replace a mutated gene in the subject that causes disease, to inactivate, or "knock out," a mutated gene, or to introduce a new gene into the subject. Exemplary nucleic acid polymers include, but are not limited to, double-stranded DNA, single-stranded DNA, double-stranded RNA, single-stranded RNA, or triple helix nucleic acid molecules. In certain instances, the nucleic acid polymers are DNA, interfering RNAs (siRNA), and micro RNAs. In the case of mitochondrial myopathies related to mitochondrial DNA dysfunction, gene therapy can be performed by direct infusion of the mitochondria to a skeletal muscle or muscles. In the case of nuclear DNA related mitochondrial myopathies, multiple infusions over time might be beneficial or required.

Minimizing Cardiotoxicity

Chemotherapy is a common treatment for various cancers, however, it also causes several serious complications. Chemotherapy-induced cardiotoxicity is one complication that limits the clinical use of chemotherapeutic agents. Certain chemotherapeutic agents, such as anthracyclines, are highly effective against acute lymphoblastic and myeloblastic leukemias, but are particularly harmful to the heart due to its effects on mitochondria. The damage to mitochondria further leads to chemotherapy-induced cardiotoxicity. Angsutararux P, Luanpitpong S, Issaragrisil S. Chemotherapy-Induced Cardiotoxicity: Overview of the Roles of Oxidative Stress. Oxid Med Cell Longev. 2015; 2015:795602. doi: 10.1155/2015/795602 (2015); Guo S, Wong S. Cardiovascular toxicities from systemic breast cancer therapy, Front Oncol. 4:346. doi: 10.3389/fonc.2014.00346. eCollection (2014).

One useful method to minimize chemotherapy-induced cardiotoxicity is to administer an effective amount of isolated mitochondria and/or a combined mitochondrial agent to a patient who is currently under a chemotherapy treatment regimen. If the patient needs to be treated with chemotherapy (e.g., because prescribed by a physician or veterinarian), the patient can be treated with mitochondria and/or combined mitochondrial agent, before, during, and/or after administration of the chemotherapy. For example, patients can be treated with mitochondria and/or combined mitochondrial agent starting immediately after administration, as a singular treatment or continuing intermittently or continuously for about 1, 2, 5, 8, 10, 20, 30, 50, or 60 days, one year, indefinitely, or until a physician determines that administration of the mitochondria and/or combined mitochondrial agent is no longer necessary.

Organ/Tissue Transplantation

The present disclosure also features methods of transplanting an organ(s), tissues, masses of cells and/or isolated cells. The methods can include a step of exposing the organ(s), tissues, mass of cells and/or isolated cells to mitochondria or combined mitochondrial agents prior to transplantation. Such exposures can occur in situ and/or ex vivo. The organ(s), tissues and/or isolated cells may be exposed to a composition comprising mitochondria or combined mitochondrial agents.

Exposure of an organ or tissue to compositions comprising mitochondria or combined mitochondrial agents can be performed ex vivo and/or in situ by any method known in the art. For example, the exposure may be performed ex vivo in any chamber or space having sufficient volume for submerging the organ or tissue, completely or partially, in the composition. As another example, the organ may be exposed to compositions comprising mitochondria or combined mitochondrial agents by placing the organ in any suitable container, and causing the compositions comprising mitochondria or combined mitochondrial agents to "wash over" the organ, such that the organ is exposed to a continuous flow of the composition.

Alternatively, the organ may be perfused with a composition comprising mitochondria or combined mitochondrial agents. The term "perfusion" is an art recognized term, and relates to the passage of a liquid, e.g., a composition comprising mitochondria or combined mitochondrial agents, through the blood vessels of an organ or tissue. Methods for perfusing organs ex vivo and in situ are well known in the art. An organ can be perfused with a composition ex vivo, for example, by continuous hypothermic machine perfusion (see Oxford Textbook of Surgery, Morris and Malt, Eds., Oxford University Press, 1994). Optionally, in in situ or ex vivo perfusions, the organ can be perfused with a wash solution, e.g., UW solution, prior to perfusion with a composition comprising mitochondria or combined mitochondrial agents, to remove the donor's blood from the organ. As another option, the UW solution can include mitochondria or combined mitochondrial agents.

The organ or tissue may be placed, e.g., submerged, in a medium or solution that includes mitochondria or combined mitochondrial agents. Alternatively, or in addition, mitochondria or combined mitochondrial agents can be added into the medium or solution. In situ exposures can be performed by any method known in the art, e.g., by in situ flushing or perfusion of the organ with a composition comprising mitochondria or combined mitochondrial agents (see Oxford Textbook of Surgery, Morris and Malt, Eds Oxford University Press, 1994).

The present disclosure contemplates that any or all of the above methods for exposing an organ or tissue to a composition comprising mitochondria or combined mitochondrial agents, e.g., washing, submerging, or perfusing, can be used in a given transplantation procedure.

The present disclosure further contemplates that a solid or semi-solid composition can be created. For example, a liquid that is a composition comprising mitochondria or combined mitochondrial agents, as described above, can be made into a solid or semi-solid composition, in which an organ or tissue may be overlaid or embedded. Alternatively, a semi-solid composition can be infused into the organ. Solid or semi-solid compositions can be made, for example, by adding a solidifying agent such as a gelling agent (e.g., collagen or alginate) to the liquid.

Methods described herein can be used to control ischemia/reperfusion damage for transplanted organs. Ischemia-reperfusion injury is a very important problem during organ transplantation. Much damage in organ transplantation appears to be induced by reperfusion injury. Organs used for transplantation often undergoes lengthy periods of cold ischemic storage after devascularization and cold perfusion, resulting in an increased susceptibility to damage upon reperfusion. Evidence shows that ischemia/reperfusion injury often leads to mitochondrial oxidative damage, which may cause delayed graft function. Dare A J, Logan A, Prime T A, Rogatti S, Goddard M, Bolton E M, Bradley J A, Pettigrew G J, Murphy M P, Saeb-Parsy K. The mitochondria-targeted anti-oxidant MitoQ decreases ischemia-reperfusion injury in a murine syngeneic heart transplant model, J Heart Lung Transplant, 34(11):1471-doi: 10.1016/j.healun.2015.05.007 (2015); Liu Q, Krishnasamy Y, Rehman H, Lemasters J J, Schnellmann R G, Zhong Z. Disrupted Renal Mitochondrial Homeostasis after Liver Transplantation in Rats. PLoS One 10(10):e0140906. doi: 10.1371/journal.pone.0140906 (2015). In some cases, the transplanted organ can be, e.g., a heart, a lung, a kidney, or a liver. In one embodiment, an effective amount (e.g., $1\times10^7$, $1\times10^8$) of mitochondria or combined mitochondria agents are injected into the blood vessels (e.g., arteries) of the transplanted organ. In another embodiment, an effective amount (e.g., $1\times10^7$, $1\times10^8$) of mitochondria or combined mitochondria agents are directly injected into the organ tissue.

An effective amount of mitochondria or combined mitochondria agents is an amount that is effective for enhancing survival and/or improving function of organs, or cells in vivo and/or in vitro. Within the context of transplantation of individual cells or masses of cells, e.g., transplant donors and/or recipients, an effective amount of mitochondria or combined mitochondria agents is an amount that is administered to the transplant donor and/or recipient sufficient to enhance survival of the cell or mass of cells, e.g. to reduce loss of the cell, or mass of cells, and/or to improve functional performance of a transplanted cell or a mass of cells. Within the context of treating cells outside a body, e.g., islet cells to be cultured and/or used for transplantation, an effective amount is an amount with which the cells are incubated or stored in order to enhance preservation of the cells and/or to reduce cell loss, e.g., loss via apoptosis, and/or to enhance function. Within the context of transplantation of organs and tissues, e.g., transplant donors and/or recipients, an effective amount of mitochondria or combined mitochondria agents is an amount that is administered to the transplant donor and/or recipient sufficient to enhance survival of the organ, tissue or cells of interest, e.g., to reduce loss of cells from which the organ or tissue is composed, and/or to improve functional performance of an organ.

In some instances, the injection is performed before the organ is retrieved from the donor. In some instances, the injection is performed at some time point after organ is retrieved, but before it is transplanted. In some instances, the injection is performed after the organ is transplanted into the recipient. In some instances, injections are performed before organ retrieval, after harvesting of the organ, and then again after implantation into the recipient. In some instances, the injection is performed during the transplantation surgery. In some embodiments, the transplanted organ is preserved in a solution containing an effective amount of isolated mitochondria or combined mitochondrial agents. In some cases, the solution is University of Wisconsin cold storage solution.

A major limitation for organ transplantation is the availability of donor organs. In order to expand the number of donor organs, centers may use organs from donors with extended criteria or donors from cardiac death. In these cases, the described methods can improve the quality of the organs, thus increasing the availability of donor organs.

The disclosure also provides methods of improving transplanted tissue and/or cell integration. In some embodiments, the tissue is skin tissue or bone marrow. In some embodiments, the cells are stem cells. In these cases, mitochondria or combined mitochondrial agents can improve the integration of the transplanted tissue and cells in the recipient's body.

Treating Mitochondrial Dysfunction Disorder

Due to mitochondria's primary function in cell metabolism, damage and dysfunction in mitochondria can cause a range of human diseases. Diseases caused by mutation in the mtDNA include Kearns-Sayre syndrome, MELAS syndrome and Leber's hereditary optic neuropathy, Pearson syndrome, and progressive external ophthalmoplegia. Other diseases that involve mitochondrial dysfunction include, but are not limited to, mitochondrial myopathy, diabetes mellitus and deafness (DAD), Leigh syndrome, "Neuropathy, ataxia, retinitis pigmentosa, and ptosis" (NARP), myoneurogenic gastrointestinal encephalopathy (MNGIE), Myoclonic Epilepsy with Ragged Red Fibers (MERRF syndrome), encephalomyopathy, lactic acidosis, Parkinson's disease, and stroke-like symptoms (MELAS syndrome), etc.

Furthermore, damage and dysfunction in mitochondria can also be caused by injury, toxicity, chemotherapy, and age-related changes. The mitochondrial dysfunction may further interfere with the proper function of the tissue or the organ of a subject.

The disclosure indicates that mitochondrial transplantation has potential to rescue cell function and replace damaged or dysfunctional mitochondria. As mitochondria can be effectively delivered to tissues through blood vessel infusion, methods described here relate to a novel method to treat mitochondrial dysfunction disorder.

The mitochondria for the treatment can be isolated from cells of an autogenous source, an allogeneic source, and a xenogeneic source. The goal is to administer enough functional mitochondria to the subject to obtain the desired therapeutic effect. In one embodiment, isolated mitochondria or combined mitochondrial agents are administered to a patient in an amount sufficient to treat the mitochondrial dysfunction disorder. Because the symptoms for mitochondrial dysfunction disorder is more likely to manifest at an organ that requires a continuous supply of energy, the administration can specifically target these affected organs, such as the heart, the brain and the liver. In one embodiment, the injection site is the blood vessel which carries the blood to the target organ. In another embodiment, the treatment involves systemic administration.

The methods described herein provide a way to treat diabetes mellitus. Some forms of diabetes are caused by mitochondrial dysfunction in beta cells. At the islet β-cell level, acute insulin release is regulated by mitochondrial ATP production and mitochondrial ROS may contribute to the long-term deterioration of insulin secretory capacity seen in type 2 diabetes. Mitochondrial function also appears a critical determinant of insulin sensitivity within muscle, liver, and adipose tissue. Sivitz, William I., and Mark A. Yorek. "Mitochondrial dysfunction in diabetes: from molecular mechanisms to functional significance and therapeutic opportunities." Antioxidants & redox signaling 12.4 (2010): 537-577. Treating these patients with isolated mitochondria or combined mitochondrial agents can restore the normal function of beta cells, thereby improving insulin production. In some embodiments, the methods involve administering an effective amount of a composition comprising isolated mitochondria or combined mitochondrial agents to patients. The composition can be administered to the patient by various routes, e.g., the composition can be directly injected into the pancreases tissue, alternatively, the composition can be injected into a blood vessel that carries the blood the pancreas. In some cases, the blood vessel is a pancreatic artery, e.g., greater pancreatic artery. In some embodiments, islet β-cells are treated with isolated mitochondria or combined mitochondrial agents, and then are transferred to a subject. These islet β-cells can come from the same subject, or from a different subject.

In addition, the methods described herein provide a way to treat Parkinson's disease. Parkinson's disease results from the dysfunction or the death of dopamine-generating cells in the substantia nigra. The causes of the cell dysfunction or the cell death are poorly understood. Evidence suggests that reduced mitochondrial activity or mitochondrial dysfunction may be part of the causes. Therefore, administering an effective amount of isolated mitochondria or combined mitochondrial agents to patients with Parkinson's disease can restore the normal function of dopamine-generating cells in these patients, thereby improving dopamine production.

Furthermore, mitochondrial dysfunctions are increasingly recognized as key components in stress-related mental disorders (e.g., post-traumatic stress disorder (PTSD)). The relationship between stress-related mental disorders and mitochondrial dysfunctions is described, e.g., in Flaquer, A., et al. "Mitochondrial genetic variants identified to be associated with posttraumatic stress disorder." Translational psychiatry 5.3 (2015): e524. Thus, in some cases, a stress-related mental disorder is also a mitochondrial dysfunction disorder. Thus, the methods described herein can also be used to treat a stress-related mental disorder, e.g., PTSD.

Treating Injuries

Injuries are often associated with mitochondrial damage and dysfunction. In some embodiments, the methods described herein can be used to treat various injuries, e.g., traumatic brain injury, concussion, amputation injury, etc.

Isolated mitochondria or combined mitochondrial agents can be used to treat wounds (e.g., open wounds, burns, and rashes). An open wound is an injury involving an external or internal break in body tissue (e.g., skin, muscle tissue, bones). In some cases, isolated mitochondria or combined mitochondrial agents can be directly injected into tissue located around the wounds. Alternatively, isolated mitochondria or combined mitochondrial agents can be applied topically at the site of the wound. In some embodiments, isolated mitochondria or combined mitochondrial agents can be administered to a subject by continuous infusion or by direct application to the injury site periodically, e.g., every two hours, until the wound heals Treatment of Cancer Methods described herein also provide treatment of cancers. Cancer cells and tumor cells need a dedicated blood supply to provide the oxygen and other essential nutrients in order to grow beyond a certain size. They often induce blood vessel growth (angiogenesis) by secreting various growth factors (e.g., VEGF). Unlike normal blood vessels, tumor blood vessels are dilated with an irregular shape and have more delicate vasculatures. As mitochondria with therapeutic agents crosses the endothelium of the blood vessels, the extensive structure in tumor blood vessels provides a natural target site for drug delivery. After combined mitochondria agents are injected into a blood vessel, they are more likely to be delivered to tumor tissues than normal tissues. In one embodiment, a cytostatic agent or cytotoxic agent can be delivered to the tumor to kill cancer cells. In one embodiment, the therapeutic agent is a chemotherapeutic agent, for example, anthracycline. In one particularly useful embodiment, the described methods are used to treat pediatric neuroblastoma and prostate cancer.

The term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

Cancers that may be treated using the methods and compositions of the present disclosure include, for example, cancers of the stomach, colon, rectum, mouth/pharynx, esophagus, larynx, liver, pancreas, lung, breast, cervix uteri, corpus uteri, ovary, prostate, testis, bladder, skin, bone, kidney, head, neck, and throat, Hodgkins disease, non-Hodgkins leukemia, sarcomas, choriocarcinoma, lymphoma, brain/central nervous system, and neuroblastoma (e.g., pediatric neuroblastoma), among others.

Further, in some embodiments, an antibody or an antigen-binding fragment can be linked or attached to mitochondria. Skilled practitioners will appreciate that linking the antibody or antigen binding fragment to mitochondria or combined mitochondrial agents can allow the mitochondria or combined mitochondrial agents to target specific sites, e.g., to target cells and/or tissues. In some instances, the antibody or the antigen-binding fragment are designed to target specific cell types, for example, cancer cells.

Treating Metabolic Disorders

White adipose tissue or white fat is one of the two types of adipose tissue found in mammals. It is often used by the body as a store of energy, and includes many white adipocytes. The other kind of adipose tissue is brown adipose tissue. The function of brown adipose tissue is to transfer energy from food into heat.

White adipocytes often contain a single lipid droplet. In contrast, brown adipocytes contain numerous smaller droplets and a much higher number of mitochondria. With the recognition that adult humans have in brown adipose tissue an organ with substantial capacity to dissipate energy, targeting brown adipose tissue thermogenesis is now viewed as a way to treat or prevent metabolic disorders, such as obesity and its associated metabolic diseases (e.g., type II diabetes). The use of brown adipose tissue to treat obesity and diabetes is described, e.g., in Cypess, Aaron M., and C. Ronald Kahn. "Brown fat as a therapy for obesity and diabetes." Current opinion in endocrinology, diabetes, and obesity 17.2 (2010): 143, which is incorporated by reference in its entirety.

As one major difference between brown adipocytes and white adipocytes is the number of mitochondria in the cell, the present disclosure provides methods of treating and preventing metabolic disorders. These metabolic disorders include, but are not limited to, obesity and its associated metabolic diseases (e.g., type II diabetes). In some embodiments, isolated mitochondria and/or combined mitochondrial agents can be directed injected into white adipose tissue in the subject. In some embodiments, the methods involving identifying a subject having or being at risk of a metabolic disorder, and delivering mitochondria or combined mitochondrial agents to the white adipose tissue by various routes (e.g., direct injection, or inject mitochondria or combined mitochondrial agents into a blood vessel, which carries blood to the white adipose tissue). In some embodiments, the methods described herein can convert white adipocytes to brown adipocytes, thus converting white adipose tissue to brown adipose tissue.

Isolated mitochondria and/or combined mitochondrial agents can be administered to a subject by focal delivery. In some embodiments, the methods involve locating the target site (e.g., fat tissue under the chin, and abdomen fat tissue), and injecting a composition comprising isolated mitochondria and/or combined mitochondrial agents to the target site. In some cases, a small amount of the composition is delivered in each injection, but the injection is repeated several times until the amount is sufficient to bring a desired effect.

Cosmetic Use

Aged or damaged skins and muscles (e.g., facial muscle) are associated with mitochondrial damage and dysfunction. Isolated mitochondria or combined mitochondrial agents can be used to improve mitochondrial function in these damaged or aged tissue, thereby removing skin wrinkles, scars, or treating loose skin, burns, wounds, lipoma, etc.

In some embodiments, the methods involve administering isolated mitochondria or combined mitochondrial agents to the aged or damaged tissues (e.g., skin tissues, or facial muscle). In some cases, the administration is performed by Gauge 24, 25, 26, 27, 28, 29, 30, 31, 32, 33, and 34 hypodermic needles. In some other cases, the isolated mitochondria or combined mitochondrial agents can be administered to the aged or damaged tissues by topical administration. Alternatively, the part of the body (e.g., hands, feet) with the aged or damaged tissues may be placed, e.g., submerged, in a container (e.g., a bathtub) filled with a medium or solution that includes mitochondria or combined mitochondrial agents. Furthermore, the mitochondria and/or combined mitochondrial agents can be administered in a continuous flow of the composition, e.g., by pouring the composition over the aged or damaged tissues.

The composition may also include an abrasive agent. The abrasive agent can effectively remove the aged or damaged cells/tissues (e.g., aged skin tissues, dead cells on a wound) and expose relatively healthy cells or tissues underneath. The isolated mitochondria and/or combined mitochondrial agents in the composition can then be taken up by these relatively healthy cells or tissues, thereby improving the mitochondrial function in these cells or tissues.

The present disclosure also contemplates that a liquid, paste, cream, gel, solid, semi-solid composition can be created. These compositions comprise mitochondrial or combined mitochondrial agents, and are suitable for external application. For example, they can be used in a topical treatment. Alternatively, they can be sprayed onto the skin or wounds.

In Vitro Fertilization

The mitochondrial genes are not inherited by the same mechanism as nuclear genes. They are typically inherited from one parent only. In humans, the mitochondria come from the egg, thus the mother. Mitochondrial donation is a specialized form of in vitro fertilization to prevent the mother's mutated mitochondrial genes from being passed to the baby. Usually, the future baby's mitochondrial DNA comes from an egg of a third party. One prominent problem of such procedure is that it results in a human offspring with three genetic parents. It leads to considerable controversy in the field of bioethics.

The described method provides a method to solve this issue. In one embodiment, the future father's cells are collected and cultured. Mitochondria are then isolated from the cultured cells. These mitochondria are then co-incubated with a mitochondria-depleted egg, which is prepared for in vitro fertilization. In another embodiment, the father's mitochondria are co-incubated with the egg, and in some instances, the embryo. In these cases, even though the mother's mutated mitochondria have not been removed, as long as there is a sufficient amount of functional and viable mitochondria in the egg or in the embryo, the baby may be treated for mitochondrial disease.

Cell Culture

The present disclosure provides methods of maintaining or culturing an animal cell in vitro. The animal cell can be cultured or simply maintained in the presence of mitochondrial or combined mitochondrial agents.

The skilled practitioner will appreciate that, culture conditions, e.g., temperature, can be selected and/or varied depending upon the type of cell to be cultured (see, for example, *Cells: A Laboratory Manual*, Spector and Leinwand, Eds., Cold Spring Harbor Laboratory Press, Cold Spring Harbor, N.Y., 1997). For example, the murine insulinoma cell line βTC3 (DSMZ, Braunschweig, Germany) can be incubated in humidified 5% $CO_2$/95% air at 37° C.

The animal cell may be disposed, e.g., suspended or bathed in, a liquid medium. The medium can be any medium known to those of skill in the art to be suitable for culturing, preserving, or washing the cells of interest (see, for example, *Cells: A Laboratory Manual*, Spector and Leinwand, Eds., Cold Spring Harbor Laboratory Press, Cold Spring Harbor, N.Y., 1997). Such types of media include, but are not limited to, various buffers, Eagle's minimal essential medium (MEM), Dulbecco/Vogt modified Eagle's minimal essential medium (DMEM), or Roswell Park Memorial Institute (RPMI) Medium. Such media may also comprise appropriate supplements, e.g., fetal bovine serum (FBS), individual amino acids, antibiotics, and/or vitamins. For example, the medium can be RPMI medium 1640 (Life Technologies, Grand Island, N.Y.) supplemented with 2 mM L-glutamine, 100 U/ml penicillin G, 100 U/ml streptomycin and 10% Fetal Calf Serum (FCS) (Life Technologies). In those embodiments, wherein the cells are in a liquid medium, the cells can be exposed to a composition comprising mitochondria and/or combined mitochondrial agents.

The present disclosure also contemplates a composition comprising cells, wherein the cells comprises combined mitochondrial agents, allogeneic mitochondria, xenogeneic mitochondria, or autogenous mitochondria with appropriate genetic modification. These cells can be any cells known in the art, e.g., stem cells, or replacement cells for various clinic use.

EXAMPLES

The invention is further described in the following examples, which do not limit the scope of the invention described in the claims.

Example 1: Isolating Mitochondria from Tissue Samples or Cultured Cells

Experiments were performed to isolate mitochondria from tissue samples or cultured cells.

Preparation

The following solutions were prepared to isolate intact, viable, respiration-competent mitochondria. To successfully isolate mitochondria using the present methods, solutions and tissue samples should be kept on ice to preserve mitochondrial viability. Even when maintained on ice, isolated mitochondria will exhibit a decrease in functional activity over time (Olson et al., *J Biol Chem* 242:325-332, 1967). These solutions should be pre-prepared if possible.

1 M K-HEPES Stock Solution (adjust pH to 7.2 with KOH).
0.5 M K-EGTA Stock Solution (adjust pH to 8.0 with KOH).
1 M $KH_2PO_4$ Stock Solution.
1 M $MgCl_2$ Stock Solution.
Homogenizing Buffer (pH 7.2): 300 mM sucrose, 10 mM K-HEPES, and 1 mM K-EGTA. Stored at 4° C.
Respiration Buffer: 250 mM sucrose, 2 mM $KH_2PO_4$, 10 mM $MgCl_2$, 20 mM K-HEPES Buffer (pH 7.2), and 0.5 mM K-EGTA (pH 8.0). Stored at 4° C.
10×PBS Stock Solution: 80 g of NaCl, 2 g of KCl, 14.4 g of $Na_2HPO_4$, and 2.4 g of $KH_2PO_4$ were dissolved in 1 L double distilled $H_2O$ (pH 7.4).
1×PBS was prepared by pipetting 100 mL 10×PBS into 1 L double distilled $H_2O$.
Subtilisin A Stock was prepared by weighing out 4 mg of Subtilisin A into a 1.5 mL microfuge tube. Stored at −20° C. until use.
BSA Stock was prepared by weighing out 20 mg of BSA into a 1.5 mL microfuge tube. Stored at −20° C. until use.

Isolate Mitochondria from Tissue

A figure outlining the procedural steps in the isolation of mitochondria using tissue dissociation and differential filtration is shown in FIG. 1. Two, 6 mm biopsy sample punches were transferred to 5 mL of Homogenizing Buffer in a dissociation C tube and the samples were homogenized using the tissue dissociator's 1-minute homogenization program (A). Subtilisin A stock solution (250 µL) was added to the homogenate in the dissociation C tube and incubated on ice for 10 minutes (B). The homogenated was centrifuged at 750×G for 4 minutes (as an optional step). The homogenate was filtered through a pre-wetted 40 µm mesh filter in a 50 mL conical centrifuge tube on ice and then 250 µL of BSA stock solution was added to the filtrate (C). The filtrate was re-filtered through a new pre-wetted 40 µm mesh filter in a 50 mL conical centrifuge on ice (D). The filtrate was re-filtered through a new pre wetted 10 µm mesh filter in a 50 mL conical centrifuge tube on ice (E). The filtrate was re-filtered through a new pre wetted 6 µm mesh filter in a 50 mL conical centrifuge tube on ice. The resulting filtrate can be used immediately or can be concentrated by centrifugation. In the case of concentration, the filtrate was transferred to 1.5 mL microfuge tubes and centrifuged at 9000×g for 10 minutes at 4° C. (F). The supernatant was removed, and pellets containing mitochondria were re-suspended, and combined in 1 mL of Respiration Buffer (G).

Immediately prior to isolation, Subtilisin A was dissolved in 1 mL of Homogenizing Buffer. Immediately prior to isolation, BSA was dissolved in 1 mL of Homogenizing Buffer. Two fresh tissue samples were collected using a 6 mm biopsy sample punch and stored in 1×PBS in a 50 mL conical centrifuge tube on ice. The two 6 mm punches of tissue were transferred to a dissociation C tube containing 5 mL of ice cold Homogenizing Buffer. The tissue was homogenized by fitting the dissociation C tube on the tissue dissociator and selecting the pre-set mitochondrial isolation cycle (60 second homogenization).

The dissociation C tube was removed to an ice-bucket. Subtilisin A Stock Solution (250 µL) was added to the homogenate, mixed by inversion, and the homogenate was incubated on ice for ten minutes. A 40 µm mesh filter was placed onto a 50 mL conical centrifuge tube on ice and the filter was pre-wet with Homogenizing Buffer, and the homogenate was filtered into the 50 mL conical centrifuge tube on ice.

Freshly prepared BSA Stock Solution (250 µL) was added to the filtrate and mixed by inversion. (This step was omitted if mitochondrial protein determination was required.) A 40 µm mesh filter was placed onto a 50 mL conical centrifuge tube on ice and the filter was pre-wet with Homogenizing Buffer, and the homogenate was filtered into the 50 mL conical centrifuge tube on ice. A 10 µm filter was placed onto the 50 mL conical centrifuge tube on ice, and the filter was pre-wetted with Homogenizing Buffer, and the homogenate was filtered into the 50 mL conical centrifuge tube on ice. The filtrate was transferred to two pre-chilled 1.5 mL microfuge tubes and centrifuge at 9000×g for 10 minutes at 4° C. The supernatant was removed, and the pellets were re-suspended and combined in 1 mL of ice-cold Respiration Buffer.

Mitochondria that were isolated from tissues should be immediately used for injection or to prepare combined mitochondrial agents.

Isolate Mitochondria from Cultured Cells

Mitochondria were also isolated from cultured cells. The procedure was essentially the same as the procedure for isolating mitochondria from tissue samples, except that human fibroblasts were used rather than biopsy samples.

Mitochondrial Number

Viable mitochondrial number was determined by labeling an aliquot (10 µl) of isolated mitochondria with MitoTracker Orange CMTMRos (5 µmol/l; Invitrogen, Carlsbad, CA, now Thermo-Fisher Scientific, Cambridge, MA). Aliquots of labeled mitochondria were spotted onto slides and counted using a spinning disk confocal microscope with a 63×C-apochromat objective (1.2 W Korr/0.17 NA, Zeiss). Mitochondria were counterstained with the mitochondria-specific dye MitoFluor Green (Invitrogen, Carlsbad, CA, now Thermo-Fisher Scientific, Cambridge, MA). Appropriate wavelengths were chosen for measurement of autofluorescence and background fluorescence with use of unstained cells and tissue. Briefly, 1 µl of labeled mitochondria was placed on a microscope slide and covered. Mitochondrial number was determined at low (×10) magnification covering the full specimen area using MetaMorph Imaging Analysis software.

Example 2: Preparing Combined Mitochondrial Agents

Experiments were performed to combine mitochondria with $^{18}F$-Rhodamine 6G, iron oxide nanoparticles, MitoTracker Orange CMTMRos (Invitrogen, Carlsbad, CA, now Thermo-Fisher Scientific, Cambridge, MA).

Combine Mitochondria with $^{18}F$-Rhodamine 6G by Electric Potential $^{18}F$-Rhodamine 6G (40-100 µCi in a volume of 20 µl) was diluted with mitochondrial isolation solution A (Homogenizing Buffer: 300 mM sucrose, 10 mM K-HEPES, and 1 mM K-EGTA, pH 7.2) at 4° C. to a volume of 1.0 mL and then fully mixed with isolated mitochondria (0.5 ml. containing $1×10^7$-$1×10^8$) in mitochondrial isolation solution A. In the mixture, $^{18}F$-Rhodamine 6G distributed electrophoretically into the mitochondrial matrix in response to the electric potential across the inner mitochondrial membrane, and therefore was sequestered by functioning mitochondria. The mixture was incubated on ice for 10-30 minutes. The mixture was washed 3 times by centrifugation at 9,000 rpm (10,000 g) for 10 minutes and the pellet resuspended each time in mitochondrial isolation solution A. Following the final wash, the pellet was resuspended in Respiration Buffer.
Combine Mitochondria with Iron Oxide Nanoparticles by Mitochondrial Outer Membrane Iron oxide nanoparticles containing a succinimidyl ester (10 mg) were suspended in respiration buffer at 4° C. and then fully mixed with isolated mitochondria (1.0 ml containing $1\times10^7$-$1\times10^8$). Iron oxide was bound to the mitochondrial amine groups on the mitochondrial outer membrane by a succinimidyl ester amine reaction. The mixture was incubated on ice for 10-30 minutes. The mixture was washed 3 times by centrifugation at 9,000 rpm (10,000 g) for 10 minutes and the pellet resuspended each time in mitochondrial isolation solution A. Following the final wash, the pellet was resuspended in Respiration Buffer.
Combine Mitochondria with Two Pharmaceutical Agents $^{18}$F-Rhodamine 6G (40-100 µCi in a volume of 20 µl) and iron oxide nanoparticles containing a succinimidyl ester (10 mg) were combined and diluted with mitochondrial isolation solution A at 4° C. to a volume of 1.0 mL and then fully mixed with isolated mitochondria (0.5 ml. containing $1\times10^7$-$1\times10^8$) in mitochondrial isolation solution The mixture was incubated on ice for 10-30 minutes. The mixture was washed 3 times by centrifugation at 9,000 rpm (10,000 g) for 10 minutes and the pellet resuspended each time in mitochondrial isolation solution A. Following the final wash, the pellet was resuspended in Respiration Buffer.
Combine Mitochondria Through Thiols MitoTracker® fluorophore (5 µmol/l; Invitrogen, Carlsbad, CA, now Thermo-Fisher Scientific, Cambridge, MA) was mixed with isolated mitochondria (1.0 mL) in respiration buffer. When the probes are mixed with functional mitochondria, they are oxidized and then react with thiols on proteins and peptides on mitochondria to form conjugates. The mixture was incubated on ice for 10 minutes at 4° C. in the dark. The mixture was washed 3 times by centrifugation at 9,000 rpm (10,000 g) for 10 minutes and the pellet resuspended each time in mitochondrial isolation solution A. Following the final wash, the pellet was resuspended in Respiration Buffer.

Example 3: Imaging

Experiments were performed to show the imaging use of combined mitochondrial agents.
Animal Model New Zealand White rabbits (Millbrook Farm, Amherst, MA) were used for the experiments. Experiments were approved by the Institutional Animal Care and Use Committee at Harvard Medical School and conformed to the National Institutes of Health (NIH) guidelines regulating the care and use of laboratory animals (NIH Publication No. 5377-3, 1996). All research was performed in accordance with the American Physiological Society's Guiding Principles in the Care and Use of Animals.

The rabbits were sedated with intramuscular administration of acepromazine (0.5 mg/kg im). A 22-gauge intravenous (iv) catheter was inserted into the marginal ear vein and secured with tape, and the rabbits were given an injection of 35 mg/kg ketamine and 2.5 mg/kg iv xylazine. This intravenous line was also used intraoperatively to administer heparin and Lactated Ringer's solution at a rate of 10 ml·kg$^{-1}$·h$^{-1}$. Heparin was injected (3 mg/kg iv via the intravenous line).

The thoracic cavity was then opened by median sternotomy. The pericardial sac was exposed and opened to form a pericardial cradle, and the animals were euthanized under deep anesthesia by exsanguination following removal of the heart.

The extracted heart was placed in a 4° C. bath of Krebs-Ringer solution (100 mmol/l NaCl, 4.7 mmol/l KCl, 1.1 mmol/l KH2PO4, 1.2 mmol/l MgSO4, 25 mmol/l NaHCO3, 1.7 mmol/l CaCl2, 11.5 mmol/l glucose, 4.9 mmol/l pyruvic acid, and 5.4 mmol/l fumaric acid). The hearts were then subjected to Langendorff retrograde perfusion for 10 min to wash out blood.
Ischemia and Reperfusion The left anterior descending artery (LAD) was located, and a Prolene thread (3-0) (Ethicon, Somerville, NJ) was passed around the artery with a taper needle, and both ends of the Prolene tie were threaded through a small vinyl tube to form a snare. The coronary artery was occluded by pulling the snare, which was then fixed by clamping the tube with a mosquito clamp. Regional ischemia was confirmed visually by regional cyanosis of the myocardial surface. Reperfusion was achieved by releasing the snare.

In contrast, global ischemia was achieved by cross-clamping the perfusion line on the Langendorff retrograde perfusion apparatus. Reperfusion was achieved by release of the cross-clamp.

For imaging, ischemia was induced for 20 min. For research on function and infarct size, regional ischemia was induced for 30 min.
Administration Langendorff rabbit hearts were either injected at the area of risk or perfused into the coronary artery with $1\times10^8$ dual-labeled mitochondria.

At the onset of reperfusion, Langendorff rabbit hearts received either several injections of sterile respiration buffer (Control Group) into the area at risk, or several injections of sterile respiration buffer containing $1\times10^7$/ml mitochondria (Injected Group). A total of $1\times10^8$ mitochondrial were injected into the area at risk. Injections were made using a sterile 1-ml insulin syringe with a 28-gauge needle. For control groups, respiration buffer without mitochondria was injected into the area at risk.

In the third group, a total of $1\times10^8$ mitochondria were perfused into the coronary artery (Perfused Group) at the onset of reperfusion.
PET Imaging was performed using a Siemens Focus 120 MicroPET scanner. Data were acquired for 60 min and reconstructed into a single image. Reconstruction was performed using unweighted OSEM2D generating an image. Image analysis was performed using the ASIPro software package (Siemens Medical Solutions).
MRI To acquire images and T2* relaxation times, the hearts were placed in a BioSpec 70/30 USR 7T MRI System (Bruker) running ParaVision Version 5.1 software or a BioSpec 4.7T MRI system (Bruker) running ParaVision Version 4.0. After an initial positioning scan, multiple-slice, FLASH cine images were acquired. Images were reconstructed and intensity data was analyzed using ImageJ software.
Micro-CT Micro-CT was performed using an Albira Preclinical Imaging System (Bruker) running Albira Software Suite version 1.530. Excised hearts were scanned at an X-ray tube voltage and current of 45 kV and 400 µA, respectively, using 600 projections per scan. The reconstructed images were 512×512×512 voxels with an isotropic voxel size of 125 µm. SPIO gradient images were analyzed using the Amide software package (http://amide.sourceforge.net). Cross sectional and volume rendered images were created using VolView, version 3.4 (Kitware).

Fluorescent Staining of Heart Tissue

Tissue samples for histochemical and microscopy studies were collected about 30 minutes after the onset of ischemia.

Transmyocardial samples were dissected from the area at risk in the left ventricular free wall and after embedding, and tissue samples were sectioned completely (5- to 7-µm thickness) and then mounted on glass slides. The slides were baked overnight at 65° C., deparaffinized in xylenes, rehydrated through a graded ethanol series, and subjected to antigen retrieval by heating three times for 5 min in 1 mmol/l ethylenediaminetetraacetic acid (pH 8.0) using a 700-W microwave oven set to high. Slides were stained immunohistochemically with the following antibodies.

Injected heart sections were fluorescently immuno-stained for desmin (green) and the human-specific mitochondrial marker MTC02 (red) (Anti-Mitochondria mouse monoclonal antibody [MTC02] (human specific), Abcam, Cambridge, MA), wheat germ agglutinin (red), the 113-1 human mitochondrial marker (green). Nuclei are identified using the DNA-binding dye 4',6-diamidino-2-phenylindole (DAPI) (blue) (Invitrogen, Carlsbad, CA, now Thermo-Fisher Scientific, Cambridge, MA). Perfused hearts were immuno-stained with α-actinin (red) and MTC02 (green) (Anti-Mitochondria mouse monoclonal antibody [MTC02] (human specific), Abcam, Cambridge, MA), or lectin (green) and 113-1 (red) staining or Prussian blue staining for iron (blue) and a pararosaniline counter-stain (pink). Some hearts were perfused with lectin prior to fixation to reveal luminal vascular surfaces. MTC02 and nuclear staining were shown with phase contrast illumination.

Other antibodies used were human specific anti-MTC02 rabbit polyclonal antibody (ab91317, Abcam, Cambridge, MA), human specific anti-mitochondria mouse monoclonal antibody [113-1] (ab92824, Abcam, Cambridge, MA), and human specific anti-MTC02 antibody rabbit monoclonal [EPR3314] (ab79393, Abcam, Cambridge, MA).

Results

Figure 2B:
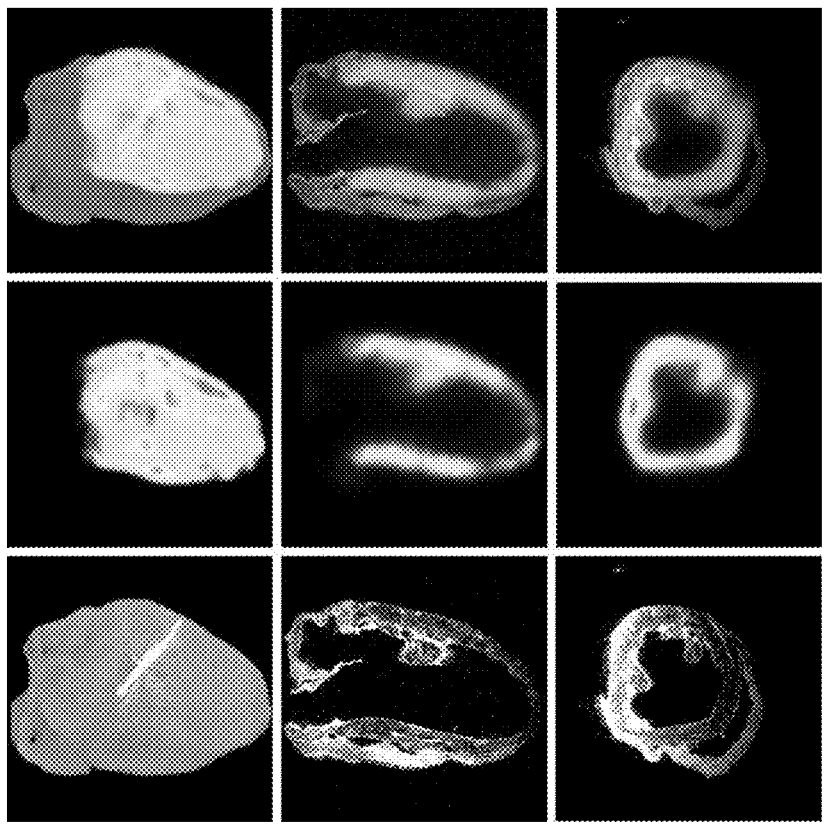
FIG. 2B is a set of images of regionally ischemic rabbit hearts perfused with $1 \times 10^8$ dual-labeled mitochondria at the onset of reperfusion. The top row displays volumetric renderings of the heart, and μCT, PET, and merged renderings are shown from left to right. The middle row shows single coronary slices of the hearts and MRI, PET, and merged images are depicted from left to right. The bottom row shows single transverse slices of perfused hearts. MRI, PET, and merged images are shown from left to right.
Figure 2A:
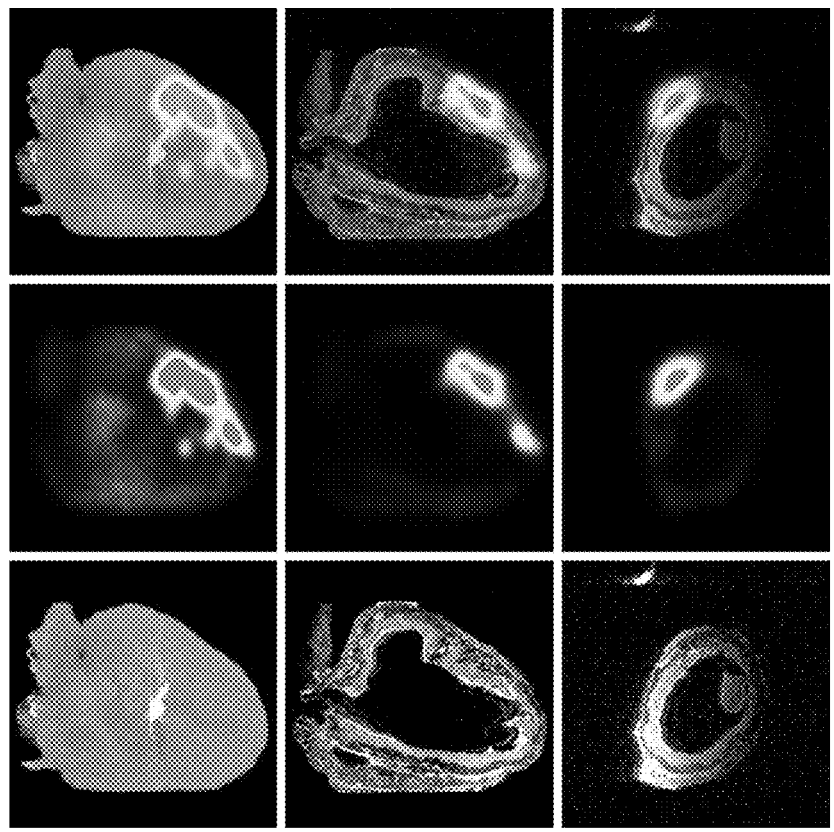
FIG. 2A is a set of images of regionally ischemic rabbit hearts injected with $1 \times 10^8$ dual-labeled mitochondria at the onset of reperfusion. The top row displays volumetric renderings of the heart. The micro-computed tomography (μCT), positron emission tomography (PET), and merged renderings are shown from left to right. The middle row shows single coronary slices of the hearts. Magnetic resonance imaging (MRI), PET, and merged images are depicted from left to right. The images in the bottom row are single transverse slices of injected hearts. MRI, PET, and merged images are shown from left to right.

Regionally ischemic rabbit hearts were injected (FIG. 2A) or perfused (FIG. 2B) with 1×10⁸ dual-labeled mitochondria at the onset of reperfusion, respectively. The top row in FIG. 2A and FIG. 2B display volumetric renderings of each heart and the micro-computed tomography (µCT), positron emission tomography (PET), and merged renderings are shown from left to right. A metal suture (bright signal on µCT) indicates the site of left anterior descending (LAD) coronary artery ligation. The middle rows in FIG. 2A and FIG. 2B are single coronary slices of the hearts and magnetic resonance imaging (MRI), PET, and merged images are depicted from left to right. The bottom rows of images in FIG. 2A and FIG. 2B are single transverse slices of injected or perfused hearts and MRI, PET, and merged images are shown from left to right. The regions of hypointense T2* MRI signals from iron correlate with PET signals from $^{18}$F-Rhodamine 6G. These figures also show that coronary artery perfusion of exogenous mitochondria resulted in wide-spread distribution of these organelles throughout the heart.

Rabbit hearts subjected to global ischemia exhibited a similar distribution of $^{18}$F-Rhodamine 6G-labeled mitochondria.

Figure 3B:
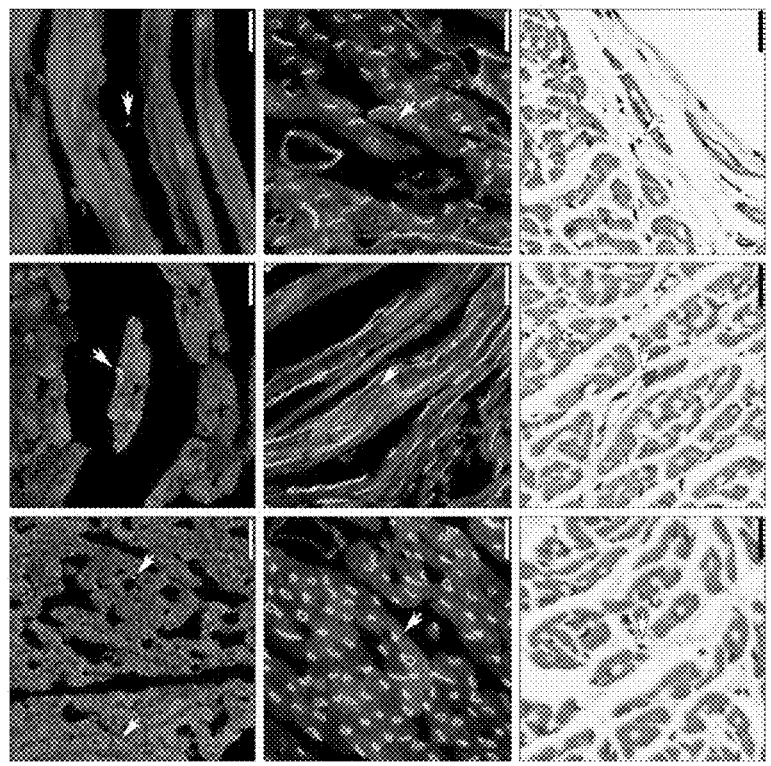
FIG. 3B is a set of images showing histological stains of ischemic hearts perfused with human mitochondria. Perfused hearts were immuno-stained with α-actinin (red) and MTC02 (green, human specific anti-mitochondria mouse monoclonal antibody [MTC02] (ab80649, Abcam, Cambridge, MA)) (top row). Transplanted mitochondria are indicated by arrows. Some hearts were perfused with lectin prior to fixation to reveal luminal vascular surfaces. The right middle row shows lectin (green) and 113-1 (red) staining; whereas, the bottom row shows Prussian blue staining for iron (blue) and a pararosaniline counter-stain (pink).
Figure 3A:
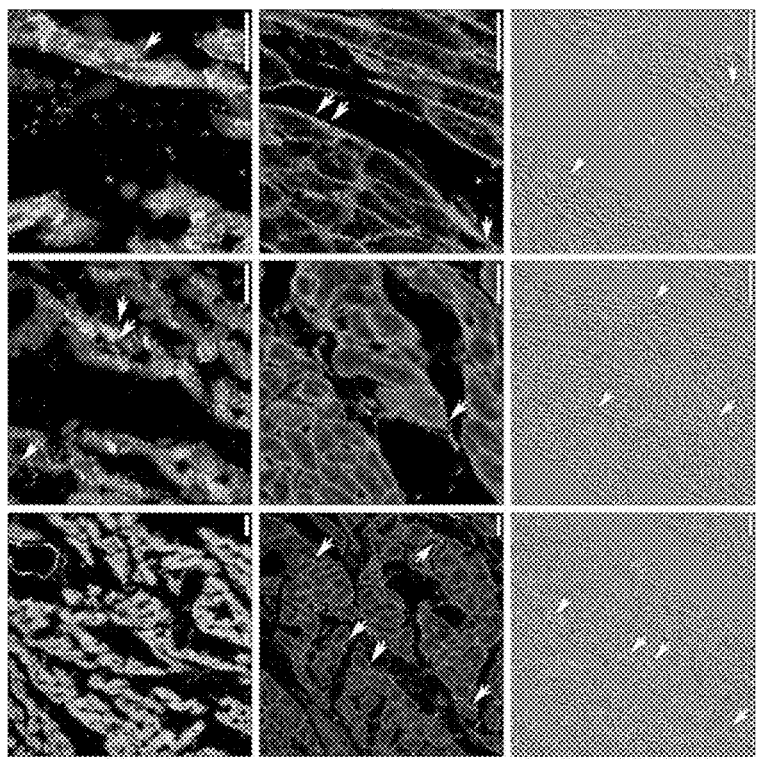
FIG. 3A is a set of images showing histological stains of ischemic hearts injected with human mitochondria. Injected heart sections were fluorescently immuno-stained for desmin (green) and the human-specific mitochondrial marker MTC02 (red, human specific anti-mitochondria mouse monoclonal antibody [MTC02] (ab80649, Abcam, Cambridge, MA)) (top row). The middle row shows staining with wheat germ agglutinin (red) and the 113-1 human specific mitochondrial marker (green) (Anti-Mitochondria antibody [113-1] (ab92824)). Nuclei are identified using the DNA-binding dye 4,6-diamidino-2-phenylindole (DAPI) (blue). MTC02 and nuclear staining is shown with phase contrast illumination (bottom row). Transplanted mitochondria associated with cardiac myocyte membranes are indicated with arrows.

FIG. 3A and FIG. 3B show histological staining of ischemic hearts injected and perfused with human mitochondria, respectively. Injected heart sections (FIG. 3A) were fluorescently immuno-stained for desmin (green) and the human-specific mitochondrial marker MTC02 (red) (top row). The left middle row shows staining with wheat germ agglutinin (red) and the 113-1 human mitochondrial marker (green). Nuclei are identified using the DNA-binding dye 4,6-diamidino-2-phenylindole (DAPI) (blue). MTC02 and nuclear staining is shown with phase contrast illumination (bottom row). Transplanted mitochondria associated with cardiac myocyte membranes are indicated with arrows (left); though, the majority of injected organelles remained in the interstitial spaces. Perfused hearts (FIG. 3B) were immuno-stained with α-actinin (red) and MTC02 (green) (top row). Transplanted mitochondria are indicated by arrows. Some hearts were perfused with lectin prior to fixation to reveal luminal vascular surfaces. The right middle row shows lectin (green) and 113-1 (red) staining; whereas, the bottom row shows Prussian blue staining for iron (blue) and a pararosaniline counter-stain (pink). These figures show that mitochondria were typically found in interstitial spaces; however, some perfused mitochondria were associated with the vasculature or internalized in cardiomyocytes.

Example 4: Therapeutic Use of Combined Mitochondrial Agents

Further experiments were performed on the animal models described in Example 3 using unlabeled, autologously-derived liver mitochondria to determine the cardio protection effect of delivering combined mitochondrial agents to ischemic hearts.

Tetrazolium Test (TTC) and Measurement of Infarct Size

Triphenyl tetrazolium chloride was used to differentiate between metabolically active and inactive tissues. In a typical tetrazolium test, the white compound is enzymatically reduced to red TPF (1,3,5-triphenylformazan) in living tissues due to the activity of various dehydrogenases (enzymes important in oxidation of organic compounds and thus cellular metabolism), while it remains as white TTC in areas of necrosis since these enzymes have been either denatured or degraded. For this reason, TTC has been employed in autopsy pathology to assist post-mortem identification of myocardial infarctions. Healthy viable heart muscle will stain deep red from the cardiac lactate dehydrogenase; while areas of potential infarctions will be more pale.

Tissue samples for histochemical and microscopy studies were collected about 150 minutes after the onset of ischemia. Area at risk (AAR) was delineated by injection of monastryl blue pigment into the aorta. The heart was rapidly removed and sliced across the long axis of the LV, from apex to base, into 1 cm thick transverse sections and traced onto a clear acetate sheet over a glass plate, under room light. The sliced hearts were incubated in 1% triphenyl tetrazolium chloride (Sigma Chemical Co., St. Louis, MO) in phosphate buffer (pH 7.4) at 38° C. for 20 min. A copy of the stained heart slices was traced onto a clear acetate sheet over a glass plate under room light. AAR in the LV and the area of infarct size (IS) were measured by planimetry. The volumes of the infarcted zone and the AAR were calculated by multiplying the planimetered areas by the slice thickness. The ratio of ARR to LV weight was calculated. Infarct size was expressed as a percentage of AAR for each heart (IS/AAR). A detailed method is described in Wakiyama H, Cowan D B, Toyoda Y, Federman M, Levitsky S, McCully J D. Selective opening of mitochondrial ATP-sensitive potassium channels during surgically induced myocardial ischemia decreases necrosis and apoptosis, Eur J Cardiothorac Surg. 21:424-

433. doi: 10.1016/S1010-7940(01)01156-3 (2002). It is herein incorporated by reference.

Result

Figure 4:
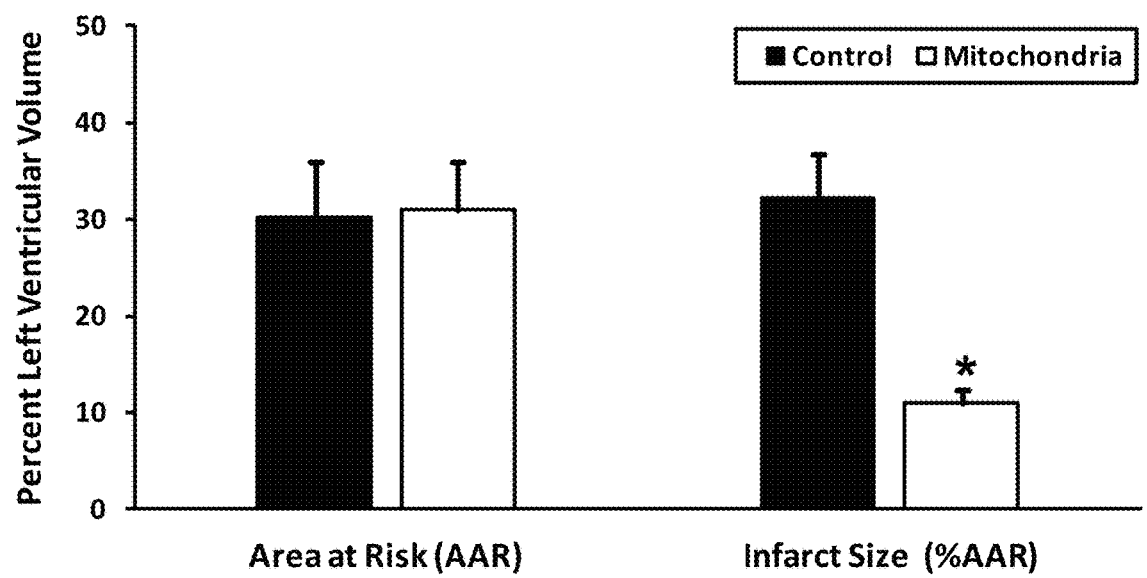
FIG. 4 is a schematic diagram showing quantitation of the area-at-risk (using Monastryl blue pigment) and infarct size (using triphenyltetrazolium chloride (TTC) staining) in control regionally ischemic hearts (n=3) and in those perfused with $1\times10^8$ autologously-derived liver mitochondria (n=3).
Figure 5:
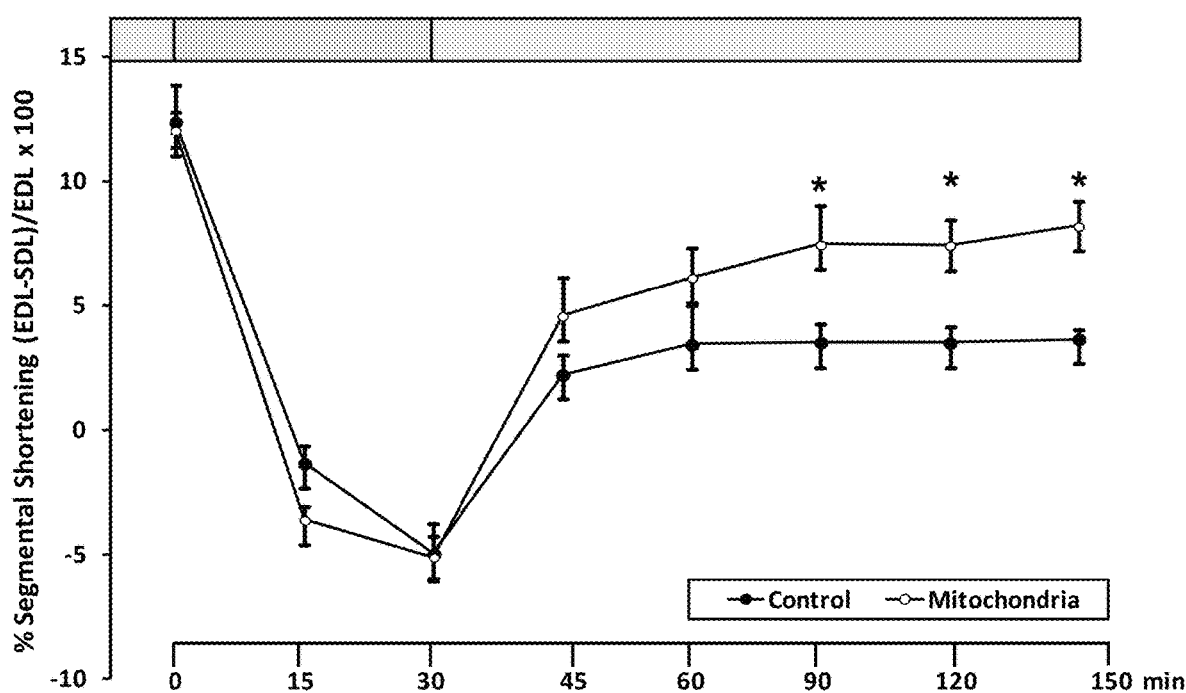
FIG. 5 is a schematic diagram showing regional myocardial function in the ischemic area assessed by segmental systolic shortening using three piezoelectric ultrasonic transducers.

Mitochondrial transplantation through blood vessel infusion prior to reperfusion significantly decreased myocyte necrosis and significantly enhanced postischemic function (FIG. 4). To quantify the extent of myocardial injury, infarct size was measured biochemically with TTC staining. Absolute measurement of infarct size by TTC staining revealed that, there was no significant difference in the size of the area at risk (i.e., the region subjected to ischemia by LAD occlusion) between the control group and the perfused group (FIG. 4), myocardial infarct size expressed as a percentage of the area at risk was significantly decreased (P<0.05) in hearts treated with mitochondria compared to controls (FIG. 4). FIG. 5 shows regional myocardial function in the ischemic area as assessed by segmental systolic shortening using three piezoelectric ultrasonic transducers. It confirms that mitochondria can provide cardio protection against ischemia and reperfusion injury.

Example 5: Rescue of Mitochondrial Function and Replacement of mtDNA

Experiments were performed to determine whether administering mitochondria to cells can rescue mitochondrial function and replace damaged mitochondrial DNA.

Method

HeLa $p^0$ cells are capable of energy generation through fermentation but lack oxygen consumption capacity due to depletion of electron transport chain proteins encoded by mtDNA. The experiment is designed to restore mitochondrial function in HeLa $p^0$ cells.

Mitochondria were isolated from HeLa cells containing intact mtDNA, and then labeled with $^{18}$F-Rhodamine 6G and 30 nm iron oxide nanoparticles. HeLa $p^0$ cells were then co-incubated with these mitochondria.

The detailed method is described in Pacak C A, Preble J M, Kondo H, Seibel P, Levitsky S, del Nido P J, Cowan D B and McCully J D, Actin-dependent mitochondrial internalization in cardiomyocytes: evidence for rescue of mitochondrial function. Biol Open 4, 622-626. PMC4434813 (2015). Herein, it is incorporated by reference in its entirety.

Result

ATP content was significantly increased in HeLa $p^0$ cells following co-incubation with mitochondria at 24, 48, 72 hours and 1 and 2 weeks. The enhanced intracellular ATP content corresponded to significant increases in oxygen consumption rates of HeLa $p^0$ cells after mitochondrial internalization.

PCR analysis demonstrated replacement of mtDNA in HeLa p0 cells following mitochondrial transplantation. While the results show that the absolute quantity of mtDNA in HeLa $p^0$ cells co-incubated with Hela cell mitochondria (containing intact mtDNA) is significantly less than that observed in HeLa cells, the mtDNA present is sufficient to significantly enhance intracellular ATP content and oxygen consumption rate as compared to untreated HeLa $p^0$ cells.

In summary, the result suggests that mitochondrial transplantation has potential to rescue cell function and replace damaged mitochondrial DNA.

Example 6: Human Patient Treatments

An effective amount of isolated mitochondria was administered to two patients in critical conditions on extracorporeal membrane oxygenation (ECMO) or extracorporeal life support (ECLS) to assess the therapeutic effects of such treatment. In each case, about 8-10 separate injections of approximately 100 microliters (containing $1 \times 10^7$ mitochondria in respiration buffer) were delivered to the area at risk (anterior and posterior) of the left ventricle. All of these procedures have been reviewed and approved by the Institutional Review Board. In each case, it has been determined that the risk associated with these procedures can be justified by the anticipated benefit.

Case Report 1

A 9-day old male patient with significant co-morbidities was placed on Extracorporeal Membrane Oxygenation (ECMO) due to surgical complications of coronary insufficiency. On ECMO day 9, the patient received surgical treatment for coronary artery repair. Following surgical repair, the patient returned to the Cardiac Intensive Care Unit (CICU) on ECMO support.

The patient continued on ECMO support but was unable to be weaned from ECMO On Day of Life (DOL) 19, rectus muscle was harvested for autologous mitochondrial isolation. The mitochondria were injected into the myocardium along the anterior and lateral aspects of the left ventricle (LV) and into the area of hypokinesis. The patient tolerated both the procedure and pacing wires being placed. The chest was left open and dressings were applied. The patient remained stable overnight on ECMO. The patient was unable to be decannulated and a second mitochondria transplantation was completed on DOL 21. Rectus muscle was again biopsied, and processed for mitochondria. The mitochondria were then injected in 10 separate injections of approximately 100 microliters. Each injection (0.1 mL containing $1 \times 10^7$ mitochondria in respiration buffer) was delivered to the area at risk of the left ventricle.

On the following day, the patient was able to be tolerate an ECMO wean trial with an epicardial echocardiogram displaying vigorous RV function and good LV function with low flows of 50 mL/kg/min. However, the patient was unable to tolerate a full clamping of the circuit, and there continued to be ongoing concern for lung, renal, hepatic organ failure. On DOL 23, after discussion with the family the decision was made to redirect care.

Case Report 2

A second patient was a two-year-old female with history of VACTERL syndrome (vertebral defects, anal atresia, cardiac defects, tracheo-esophageal fistula, renal anomalies, and limb abnormalities), tricuspid atresia 1B with pulmonary stenosis (PS) and ventricular septal defect (VSD) with complex cardiac surgical history presented for staged palliation of her single ventricle circulation. The intra-operative course was complicated by numerous runs of cardiopulmonary bypass (CPB) for poor oxygenation and ventilation and diminished right pulmonary artery (RPA) blood flow Post-operative transesophageal echocardiogram (TEE) revealed ventricular function varying between normal and moderately depressed. She was stabilized and transferred to the cardiac intensive care unit (CICU) with an open chest and mechanical ventilation.

On post-operative day (POD) 1 myocardial function deteriorated and she was cannulated to extracorporeal membrane oxygenator (ECMO). Angiography revealed that the left anterior descending coronary artery (LAD) was nearly completely occluded with significant narrowing Surgical intervention restored coronary flow. The patient returned to CICU on full flow ECMO support and remained critical yet stable. On POD 3, the patient returned to catheterization lab for repeat assessment of LCA. There again was no significant flow noted through the left main coronary (LMA). The LMA was stented and expanded and repeat angiography revealed restoration of flow to the LMA and LAD. On POD 4, an echocardiogram revealed mild MR, mild aortic regurgitation (AR), and severe global LV dysfunction. Patient remained critical but stable on ECMO support.

On POD 5, the patient still exhibited severe LV dysfunction on echocardiogram. The decision was made to move forward with autologous mitochondria transplantation concurrent with chest washout, hematoma evacuation, and new atrial lead placement. Following all clinical procedures, a TEE was completed to confirm LV dysfunction, mostly along the posterior free wall. A rectus muscle biopsy was performed and mitochondria were harvested from tissue. The mitochondria were aliquoted into 10 separate injections of 100 microliters each with $1 \times 10^7$ mitochondria per injection. Injections into the dysfunctional myocardium were made in several positions: five injections anteriorly and five injections along the posterior left ventricle. The patient tolerated the injections well with no evidence of electrical disturbances as determined by electrocardiogram (ECG) or of intramural hematoma or evidence of arrhythmia as determined by echocardiogram.

On POD 7, a repeat catheterization was done and showed at least moderate LV dysfunction; of note, the LCA stent was stable and there were good flows through both coronaries. The patient was decannulated from ECMO the following day with stable moderate dysfunction. On POD 14, improvement of function to mild dysfunction was noted with no mitral regurgitation (MR) or AR, with continued good flows through stent. Cardiac function remained stable at mild dysfunction until the patient's discharge on POD 38.

Example 7: High Resolution Microscopy

Experiments were performed to image mitochondrial fusion in cardiac cells and to demonstrate fusion mechanisms. 3-D super-resolution microscopy was used to study internalization of mitochondria in human iPS-derived cardiomyocytes and primary human cardiac fibroblasts.

Mitochondria in human fibroblasts were labeled using a mitochondrial specific baculovirus vector for green fluorescent protein (GFP). Mitochondria in human iPS cardiac cells were labeled using a mitochondrial specific baculovirus vector for red fluorescent protein (RFP).

GFP-labeled mitochondria were then isolated from BacMam 2.0 infected human fibroblasts and these organelles were incubated with cardiac fibroblasts containing RFP-labeled mitochondria. Isolated mitochondria retained their membrane potential as determined by incubation with MitoTracker Red CMXRos and were reactive with an anti-human mitochondrial antibody. Experiments confirmed that isolated mitochondria produce ATP and are respiration-competent, which is a requirement for their internalization and function. After 2 or 4 hours, the cells were fixed and mounted to assess if super-resolution structured illumination microscopy (SR-SIM) could resolve the intracellular position of internalized mitochondria. Experiments showed that exogenous mitochondria were rapidly internalized in human cardiac fibroblasts (HCF) and co-localized with the mitochondrial network of recipient fibroblasts. To establish if endocytosed mitochondria fused with the mitochondrial network in recipient cardiac fibroblasts, comparable experiments were performed on human cardiac fibroblasts using 3 of the 4 available laser lines.

Figure 6B:
FIG. 6B is a SR-SIM green channel image showing mitochondrial internalization and fusion in human cardiomyocytes.
Figure 6D:
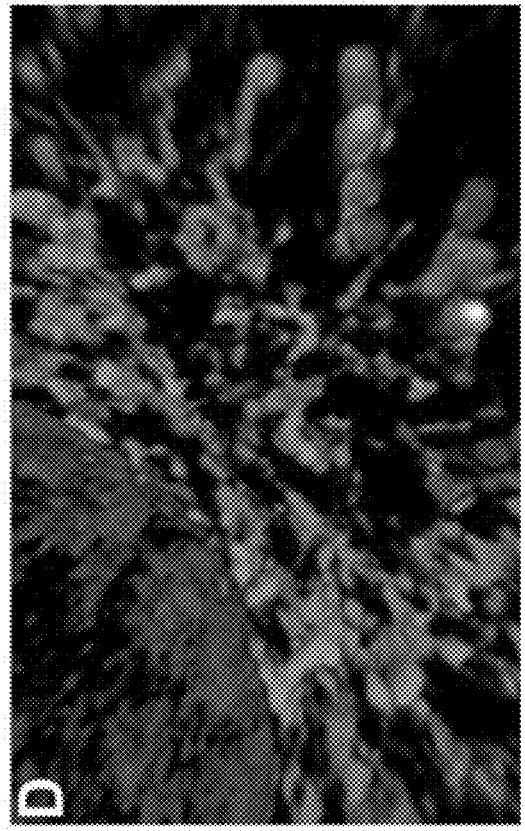
FIG. 6D is a SR-SIM merged image showing mitochondrial internalization and fusion in human cardiomyocytes.
Figure 6A:
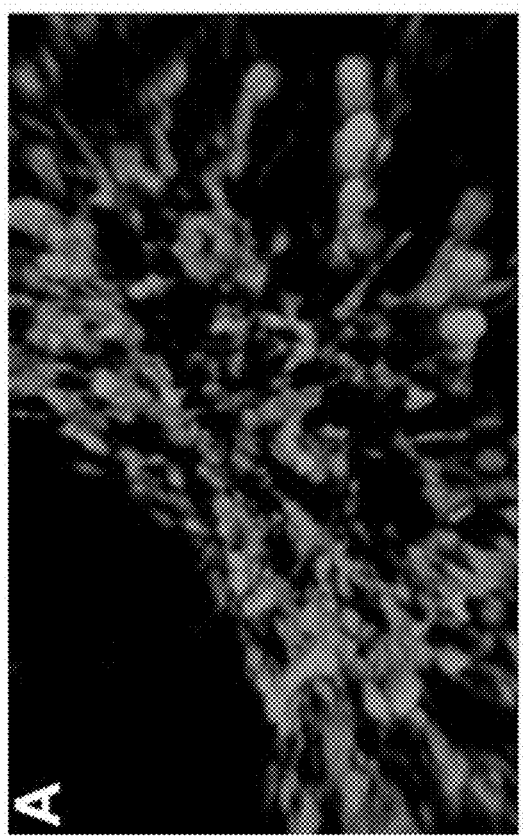
FIG. 6A is a super-resolution structured illumination microscopy (SR-SIM) red channel image showing mitochondrial internalization and fusion in human cardiomyocytes.
Figure 6C:
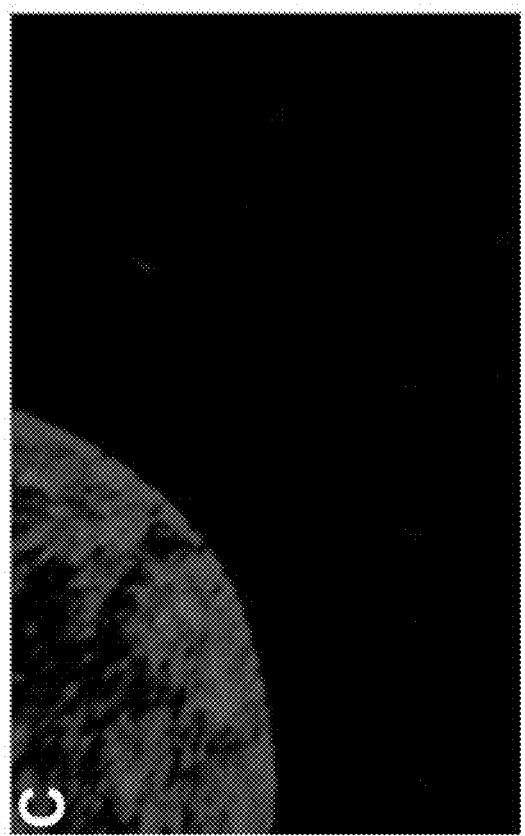
FIG. 6C is a SR-SIM blue channel image showing mitochondrial internalization and fusion in human cardiomyocytes.
Figure 7A:
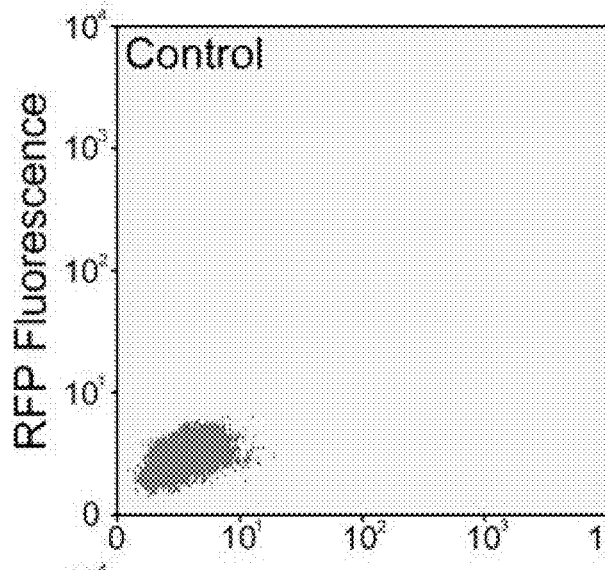
FIG. 7A is a graph showing the results of flow cytometry for mitochondria in the control group.
Figure 7B:
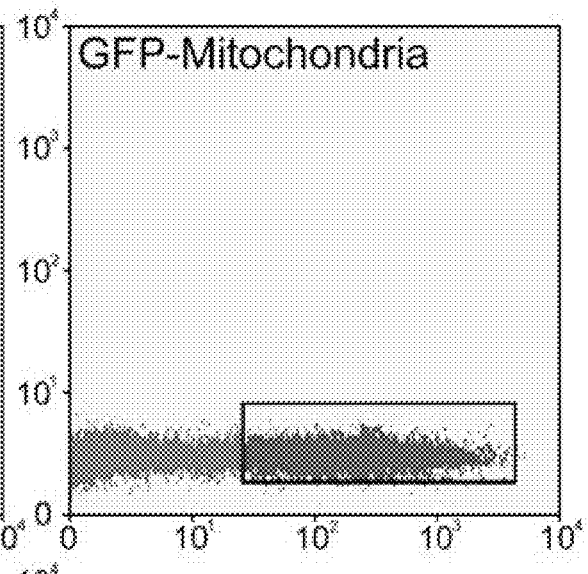
FIG. 7B is a graph showing the results of flow cytometry for green fluorescent protein (GFP)-labeled mitochondria.
Figure 7C:
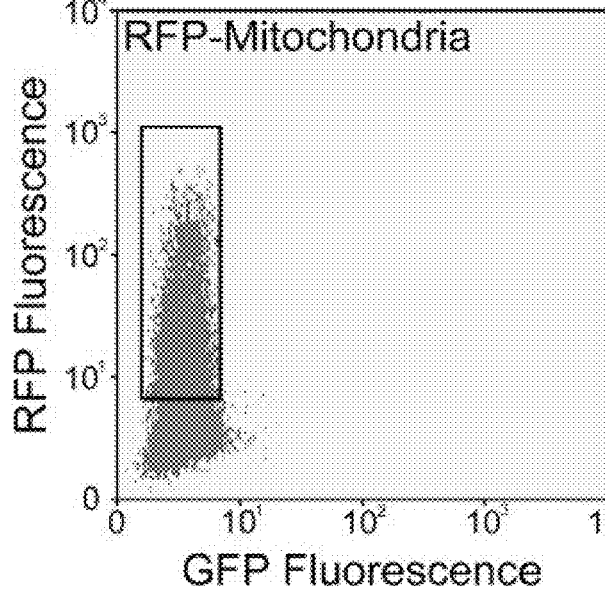
FIG. 7C is a graph showing the results of flow cytometry for red fluorescent protein (RFP)-labeled mitochondria.
Figure 7D:
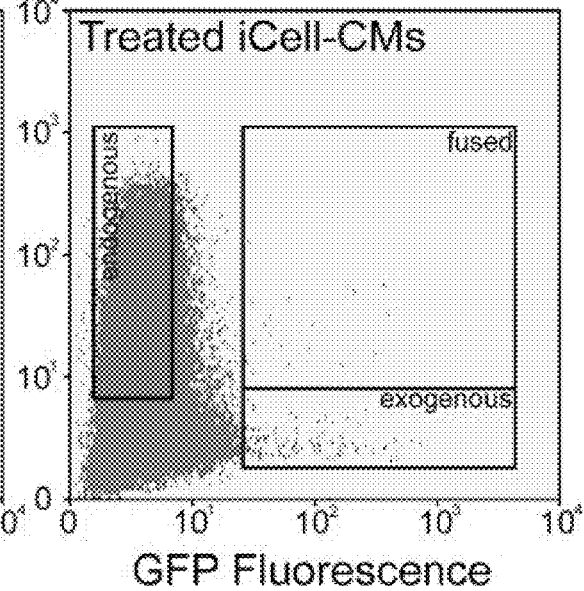
FIG. 7D is a graph showing the results of flow cytometry for mitochondria isolated from iCell® cardiomyocytes treated with GFP-labeled mitochondria.

Rotation of the volumetric rendering of the SR-SIM images revealed what appeared to be exogenous mitochondria fusing with the endogenous mitochondrial network of recipient fibroblast cells. More extensive analyses of similar experiments using iCell® cardiomyocytes (iCell-CM) (FIGS. 6A-6D) confirmed fusion of exogenous, fibroblast-derived mitochondria containing a targeted GFP with the endogenous organelle network by 4 hours. FIGS. 6A-6D show the 3-D volumetric renderings of a cardiomyocyte expressing mitochondrial-targeted RFP that was treated with isolated GFP-mitochondria for 0.5, 1, 2, and 4 hours. Fusion of the exogenous mitochondria with the endogenous mitochondrial network is readily apparent (FIG. 6A shows red channel, FIG. 6B shows green channel, FIG. 6C shows blue channels, and FIG. 6D shows the merged image).

These results provided compelling evidence for the potential of using SR-SIM to clearly determine the location of mitochondria internalized in cells and confirmed the fusion of exogenous mitochondria with endogenous mitochondria.

To confirm and quantitate the observations, fluorescence-activated cell sorting (FACS) was used. After verifying that isolated mitochondria using flow cytometry could be analyzed, GFP-labeled mitochondria from infected HCFs were added to iCell-CMs containing RFP-labeled mitochondria for 4 hours. By washing these cells and then isolating the entire population of mitochondria, mitochondria that fluoresced both red and green was observed (FIGS. 7A-7D). In FIGS. 7A-7D, green fluorescence is shown in the X axis and red fluorescence is shown in the Y axe (logarithmic), respectively. The control group represents unlabeled mitochondria and the GFP and RFP-Mitochondria groups were isolated from infected HCFs. Total mitochondria were isolated from iCell-CMs expressing RFP-Mitochondria (endogenous) treated for 4 hours with isolated HCF GFP-labeled mitochondria (exogenous). Mitochondrial fusion was evident in organelles that were fluorescent in both the green and red channels. These experiments showed that 18.1% of exogenous mitochondria were fusing with endogenous mitochondria by 4 hours. Obviously, the endogenous mitochondria (both labeled and unlabeled) greatly outnumber the exogenous mitochondria; however, the experiments have proven that few organelles are required to elicit an improvement in cardiac function.

Because the results indicated that a significant number of the exogenous mitochondria fused with the endogenous mitochondrial network, other cell compartments were examined to understand the point at which these organelles escape from the endosomal-lysosomal system. To maximize the information obtained through SR-SIM, all 4 available laser lines were used. To test the ability to interpret red, green, blue, and far red channels in a single acquisition, iCell-CMs were infected with BacMam 2.0 CellLight™ RFP-Mitochondria and treated these cells with $1 \times 10^7$ GFP-labeled HCF mitochondria for 4 hours. Following treatment, the cardiomyocytes were washed and stained with 4',6-diamidino-2-phenylindole (DAPI) and an antibody to α-actinin (ACTN), which was detected with an Alexa 633-conjugated secondary antibody. This study showed that using a combination of fluorescent protein expression and antibody detection, a lot of information can be extracted from each acquisition and the identity of various cell compartments and structures can be determined.

This strategy was used to investigate endosomal escape by treating cardiomyocytes with isolated mitochondria for 1 hour. iCell-CMs were first infected with RFP-Early Endosome or RFP-Late Endosome CellLight™ reagents and then treated with GFP-labeled mitochondria isolated from HCFs.

Internalized exogenous mitochondria were endocytosed through an actin-dependent mechanism into an acidic cellular compartment. In addition to employing the CellLight™ reagents, an anti-human mitochondrial antibody (MTC02) was used to ensure the green fluorescent spheres are internalized mitochondria.

The results showed that by 1 hour, internalized mitochondria had passed through early endosomes and were contained within late endosomes. Four channel super-resolution microscopy revealed the escape of GFP-labeled mitochondria from the late endosomes and all of these mitochondria reacted well with the MTC02 antibody.

Figure 8:
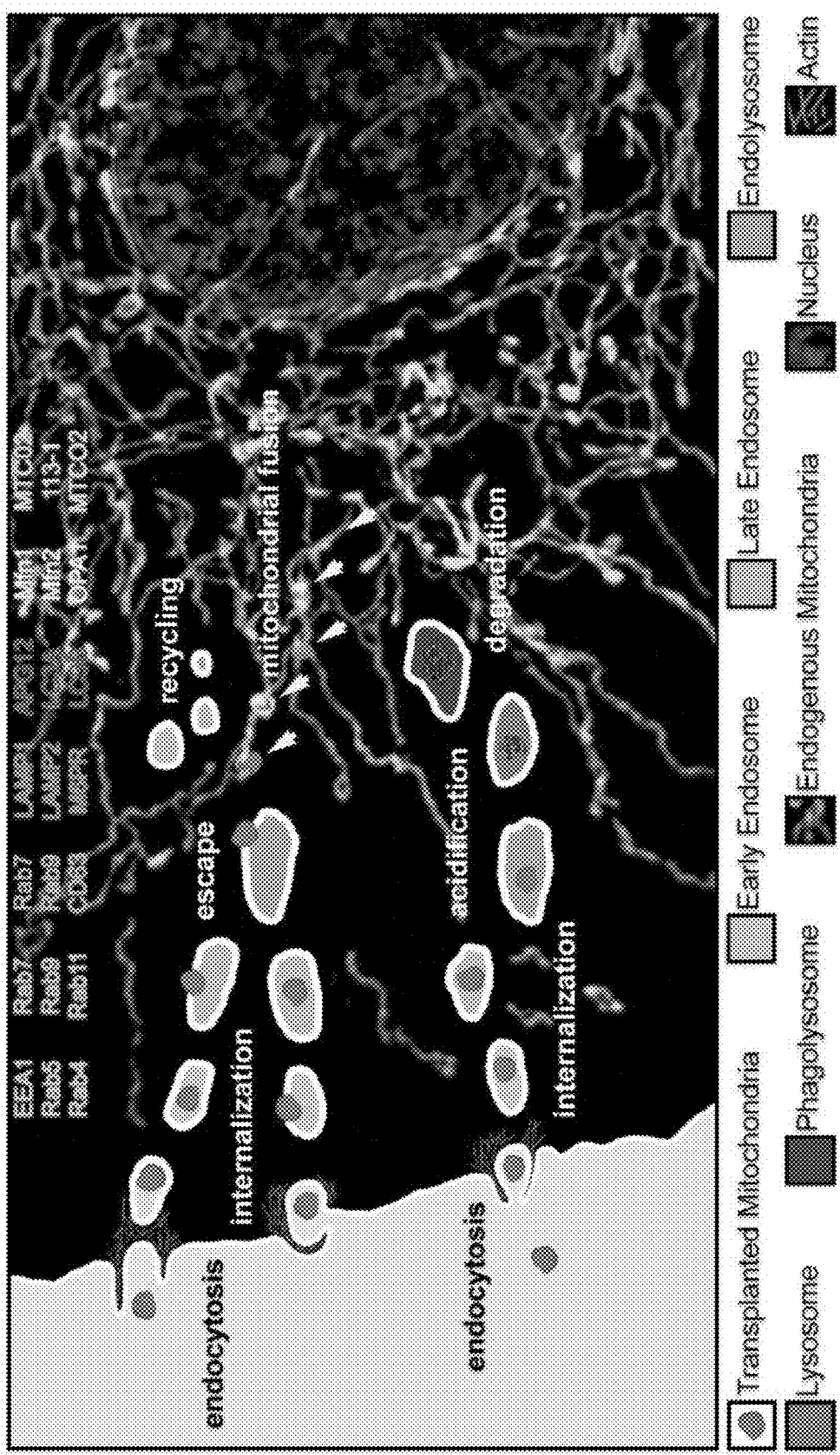
FIG. 8 is a schematic diagram showing a proposed model of the endosomal pathways for mitochondria internalization.

By using SR-SIM and flow cytometry, a proposed model of the endosomal pathways involved in mitochondrial internalization has been created. FIG. 8 is a schematic representation of the intracellular fates of exogenous mitochondria. Isolated mitochondria enter cardiac cells (HCFs and iCell-CMs) through actin-dependent endocytosis. Internalized organelles rapidly proceed from early endosomes (<0.5 hours) into late endosomes, endolysosomes, and lysosomes (0.5 to 4 hours). Each of these compartments can be identified using established protein expression profiles (top of figure). Mitochondrial escape appears to occur principally from the late endosomal compartment. Escaped exogenous mitochondria then fuse with endogenous mitochondria (indicated by arrowheads). Other internalized exogenous mitochondria are directed toward degradation through the phagolysosomal pathway.

In summary, the results demonstrated that mitochondria enter the cell by endocytosis. These organelles either escape from early endosomes, late endosomes, and endolysosomes or are degraded through the lysosomal and phagolysosomal pathway. Exogenous mitochondria that escape from the endosomal compartments go on to fuse with the endogenous cardiomyocyte mitochondrial network. The time frame for uptake occurs at >30 minutes. The results further demonstrated that 3-D super-resolution structured illumination microscopy can be used in connection with labeled mitochondrial for various imaging purposes.

Example 8: Coronary Vascular Infusion and Blood Flow

Examples in this disclosure have demonstrated that mitochondria can be delivered through the vasculature to the heart. The vascular delivery of mitochondria through the coronary arteries results in the delivery and uptake of mitochondria throughout the entire heart in 10-30 minutes after injection. This is in contrast to the direct injection of mitochondria into the heart itself where the mitochondria remain in the area in which they were injected. Thus, vascular delivery of mitochondria provides a rapid method to allow for distribution of mitochondria in the entire heart and to provide energy and recovery to the entire heart, but there are some concerns. When the heart is injured, the vasculature will change. These changes may affect the delivery or uptake of the injected mitochondria. It is possible that the mitochondria rather than being passed through to the heart cells, may get stuck in the vasculature due to its altered state and clog the vasculature. This would damage the heart by stopping blood flow to the heart and could cause death. To address these concerns, experiments were performed to demonstrate that the mitochondria do not alter blood flow in the heart.

Figure 9:
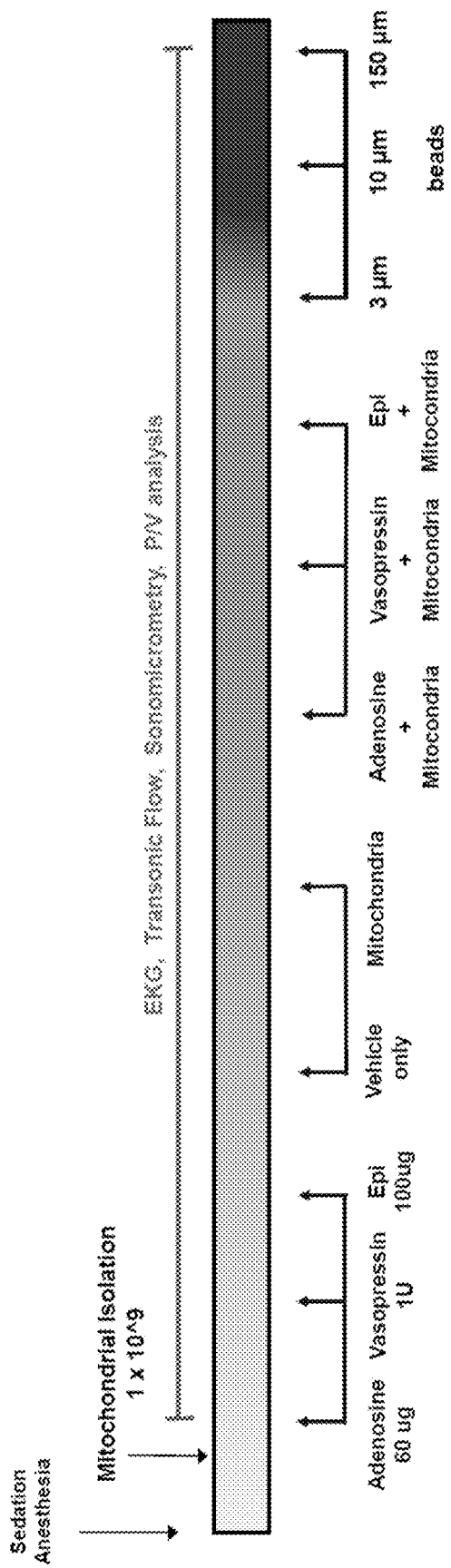
FIG. 9 is a diagram showing an experimental protocol for demonstrating that injected mitochondria do not obstruct coronary blood flow.

In this example, all experiments were performed in the clinically relevant swine model. Blood flow in the heart was measured, and then mitochondria or other agents were delivered by coronary vascular infusion. Blood flow was then measured again to determine if there are any changes in blood flow. As shown in FIG. 9, the coronary arteries were constricted with vasopressin and then with epinephrine (Epi) to induce increased heart rate. Adenosine was used to demonstrate reactivity of the blood vessels. These experiments were performed both in the normal heart and the damaged heart. Polystyrene beads were also used for positive control. 3 um, 10 um and 150 um polystyrene beads were used to block blood flow. No immune or auto-immune reactions were observed in the entire experiments.

The results show that mitochondrial delivery by coronary vascular infusion does not alter vascular flow or myocardial perfusion in the normal or vasoconstricted heart. FIGS. 10A-10C and FIGS. 11A-11D show that there is no change in heart rate or conductance with vascular delivery of mitochondria. These results demonstrated that there are no coronary blocks following coronary infusion of mitochondria. These results confirm that coronary infusion of mitochondria can be readily used in cardiac surgery.

Figures 12A, 12B:
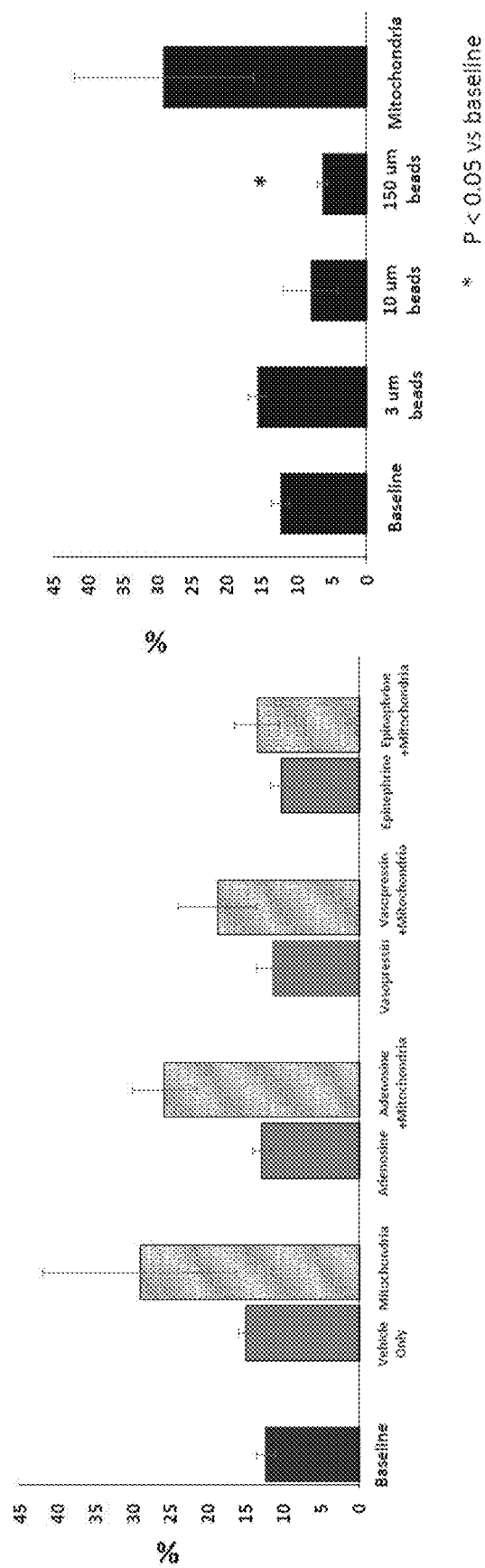
FIG. 12A is a bar graph showing percentage of systolic shortening after coronary infusion of vehicles, adenosine, epinephrine, vasopressin, and mitochondria.
FIG. 12B is a bar graph showing percentage of systolic shortening after coronary infusion of 3 um, 10 um and 150 um polystyrene beads and mitochondria.

In addition, mitochondrial delivery by vascular infusion significantly increased coronary blood flow without altering mean blood pressure or heart rate. FIGS. 12A-12B are a set of graphs showing percentage of systolic shortening after coronary infusion of various agents. FIGS. 13A-13B are a set of graphs showing coronary blood flow after coronary infusion of various agents. FIGS. 12A-12B and FIGS. 13A-13B show that coronary infusion of mitochondria increases coronary blood flow. This response was greater than the response to the drug that can increase blood flow, such as adenosine, and overcame the vasoconstriction induced by vasopressin. The ability to increase blood flow with no increase in heart rate allows for clinical usage in angina type injury and in ischemia/reperfusion related injury and in tissue damage areas, wherein increased blood flow and oxygen delivery would be needed.

Figure 14:
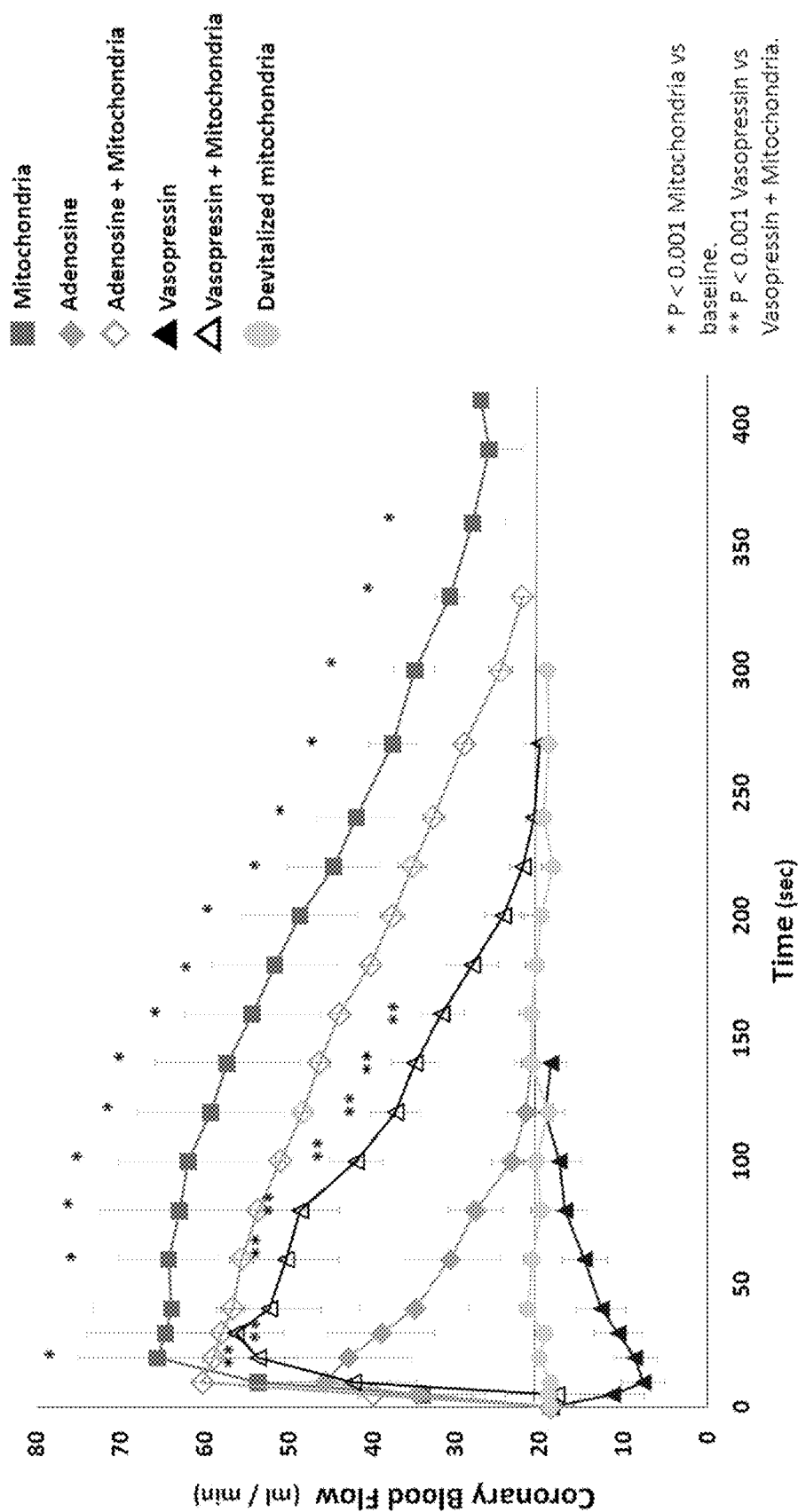
FIG. 14 is a graph showing coronary blood flow at different time points after coronary infusion of adenosine, vasopressin, mitochondria, and devitalized mitochondria (mitochondria $1\times10^9$ organelle/ml; adenosine 60 ug; vasopressin 1U; devitalized mitochondria $1\times10^9$ organelle/ml; baseline=20 ml/min; values are mean±SE).

The increase in coronary flow was also concentration dependent and lasted for approximately 5 min. FIG. 14 shows that mitochondria extended the vasodilation beyond that of adenosine, and the vasodilatory effects of mitochondria infusion were immediate. The effects were also dependent on the length of the time period between the time of mitochondria isolation and the time of use. The vasodilatory effects decreased as time from isolation was extended (e.g., being stored for 30-60 minutes). Thus, mitochondria must be freshly isolated and viable. Dead and devitalized mitochondria are not effective in increasing coronary blood flow (FIGS. 13A-13B and FIG. 14).

Figures 15A, 15B:
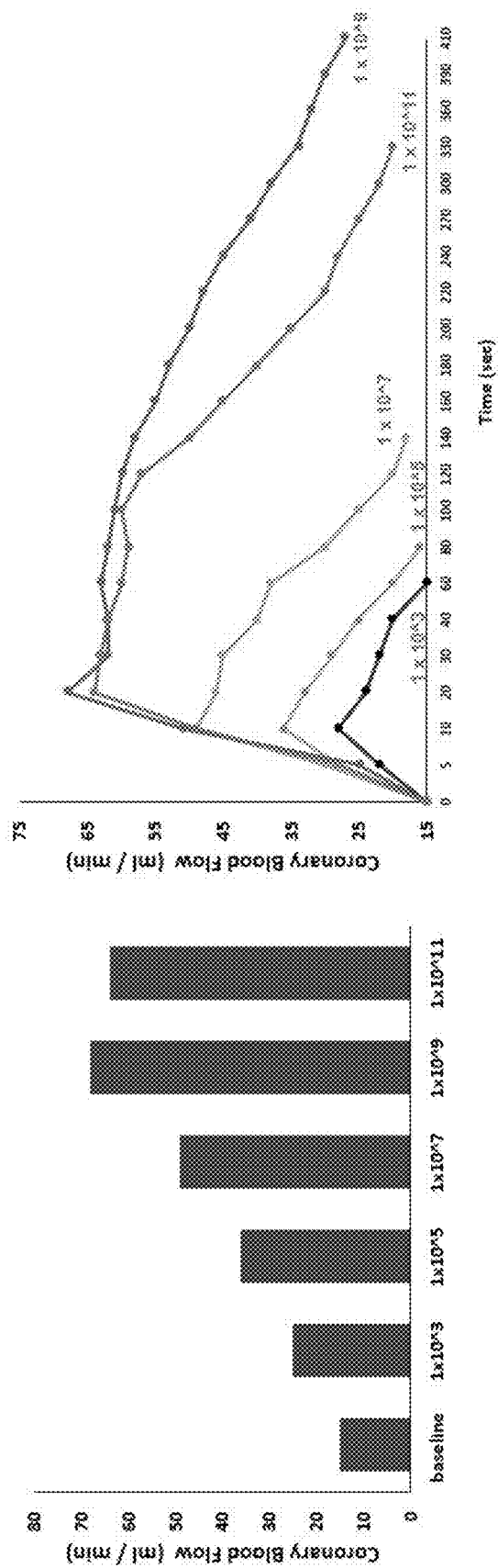
FIG. 15A is a bar graph showing the coronary blood flow in response to different doses of mitochondria.
FIG. 15B is a graph showing the coronary blood flow at different time points in response to different doses of mitochondria.

FIGS. 15A-15B further show the coronary blood flow in response to different doses of mitochondria. Optimal coronary flow was achieved using $1 \times 10^9$ mitochondria.

Example 9: Coronary Vascular Infusion for Treating Myocardial Damages

Experiments were also performed to demonstrate the efficacy of mitochondrial delivery by vascular infusion to limit myocardial damage and to enhance myocardial function following experimentally induced reversible myocardial ischemia in the clinically relevant swine model.

Figure 16:
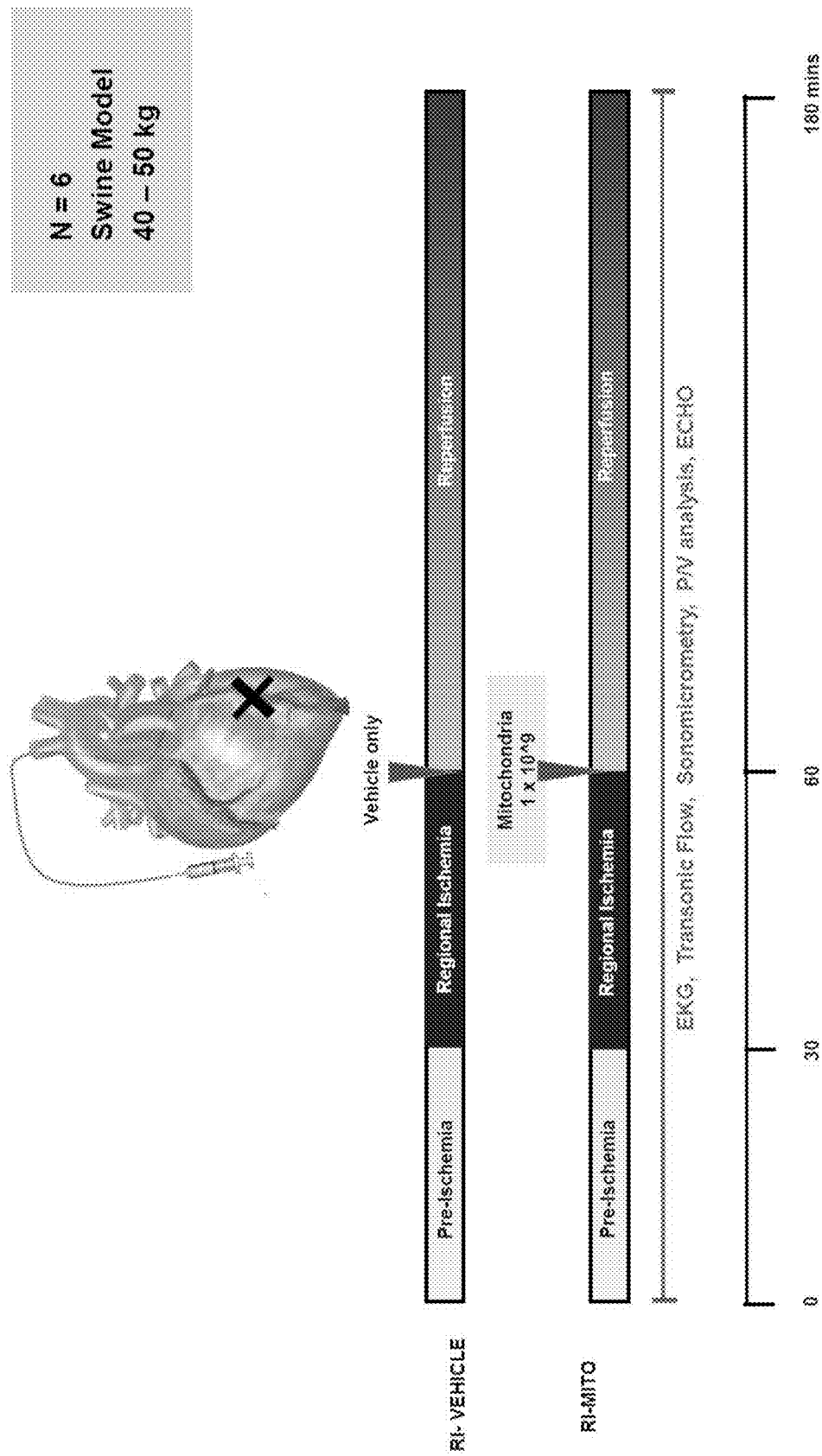
FIG. 16 is a diagram showing the methods to demonstrate cardioprotection afforded by vascular infusion of mitochondria in a large animal model (swine).
Figures 17A, 17B:
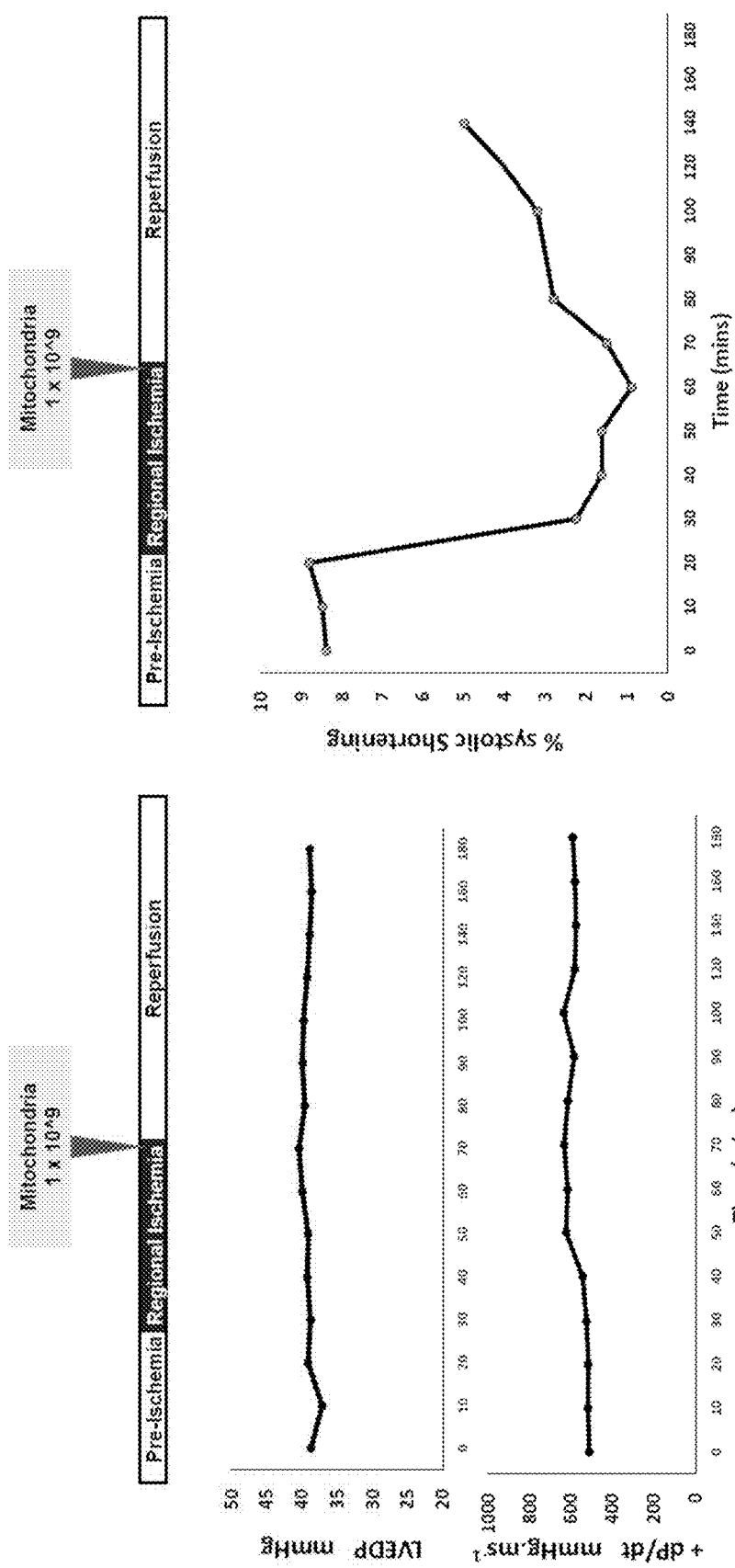
FIG. 17A is a set of graphs showing left ventricular end-diastolic pressure (LVEDP) and dP/dt of the left ventricle pressure with vascular infusion of mitochondria.
FIG. 17B is a graph showing percentage of systolic shortening with vascular infusion of mitochondria.
Figure 18A:
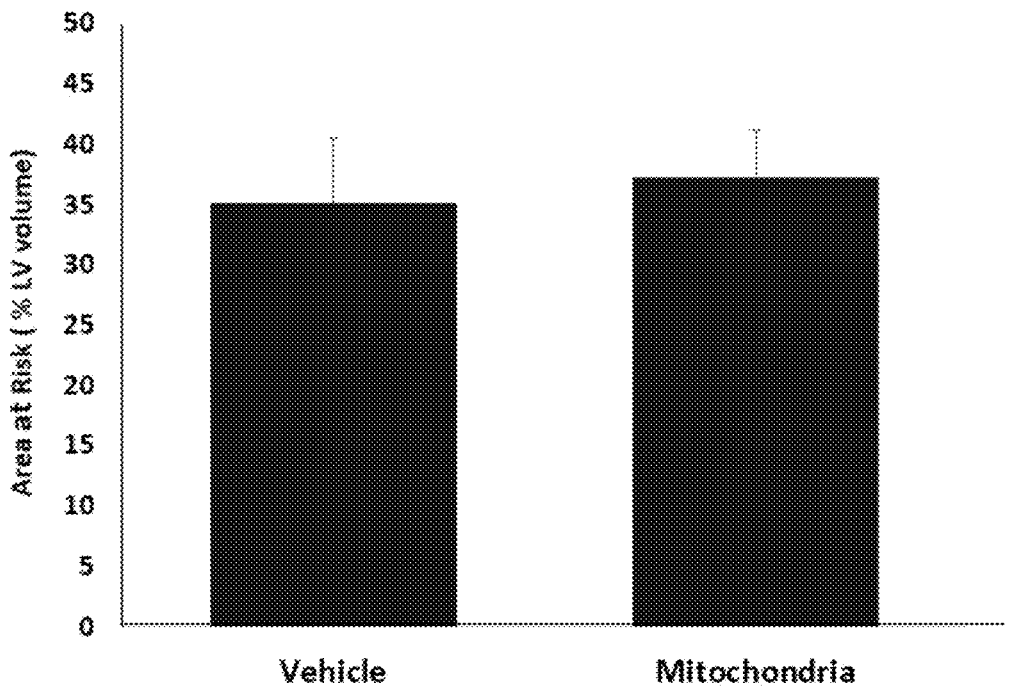
FIG. 18A is a graph showing percentage of area at risk in left ventricle with vascular infusion of vehicles and with vascular infusion of mitochondria.
Figure 18B:
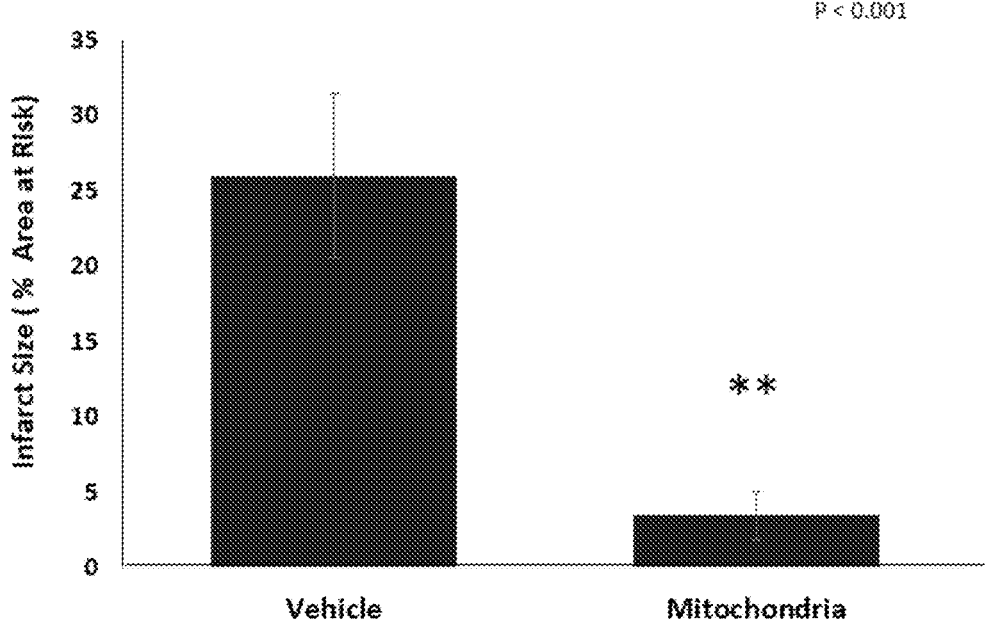
FIG. 18B is a graph showing percentage of infarct size in area at risk with vascular infusion of vehicles and with vascular infusion of mitochondria.

Pigs received either 15 minutes (stunning) or 30 minutes (ischemia/reperfusion injury) of regional ischemia, and 120 minutes reperfusion (FIG. 16). Comparison between these groups provided a means to determine the effects of mitochondria infusion in models of live tissue (stunning) as compared to a heterogeneous mixed cell (live and dead) population (ischemia/reperfusion injury).

Three groups each in stunning and ischemia/reperfusion were investigated: two regional ischemia groups with LAD regional ischemia, and a sham-control group where the snare in the animals was not tightened or fixed and no regional ischemia was present. Following 15 or 30 minutes regional ischemia, the snare was released and hearts would receive either a single 10 mL injection of sterile respiration buffer (RI-vehicle and Sham Control) or a single injection of sterile respiration buffer (10 mL) containing mitochondria ($1.7 \times 10^7$, RI-Mitochondria) administered antegrade through the angiography catheter into the left coronary ostium. The catheter was flushed with 10 mL saline. The animals remained under anesthesia for two hours to allow for reperfusion of the area at risk. These experiments confirmed that vascular infusion of mitochondria reduced infarct size and enhanced post-ischemic functional recovery in the clinically relevant swine model (FIGS. 17A-17B, FIGS. 18A-18B).

Example 10: Immune Response

Experiments were performed to demonstrate that no B-cell or T-cell immune response to single or multiple auto- or allogeneic mitochondria injections at any concentration.

To demonstrate the immunogenicity of auto- and allogeneic mitochondria, 5-8 weeks old female mice, BALB/cJ (recipient and donor) and C57BL/6J (donor) were used.

The first experiment was designed to determine the immune response to single and multiple injections of mitochondria. Three groups were investigated. The mice received a single intraperitoneal (ip) injection (0.5-1.0 mL) containing either $1 \times 10^5$ (n=10); $1 \times 10^6$ (n=10) or $1 \times 10^7$ (n=10) of mitochondria. Autogeneic mitochondria were isolated form BALB/cJ mice. Allogeneic mitochondria were isolated form C57BL/6J mice. To provide a positive control, mice received a single injection of allogeneic splenocytes isolated from C57BL/6J mice. A separate group of mice (BALB/cJ, n=10) that received a single intraperitoneal injection (0.5-1.0 mL) of sterile respiration media was used as a control.

Figure 19A:
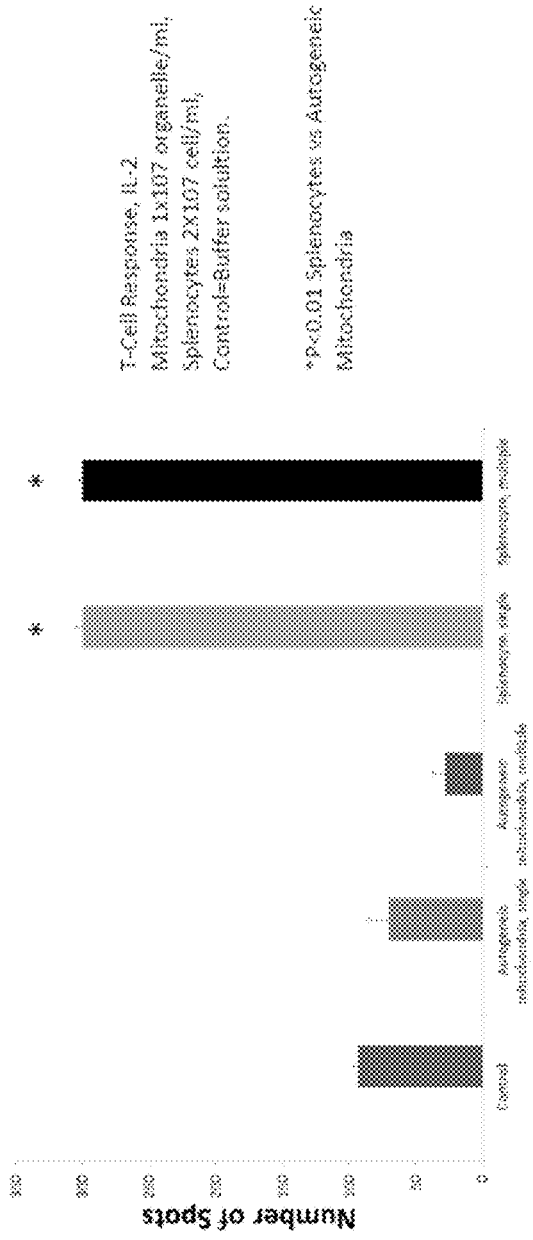
FIG. 19A is a bar graph showing number of spots in mice receiving single or multiple injections of autogeneic mitochondria, and single and multiple injections of splenocytes.
Figure 19B:
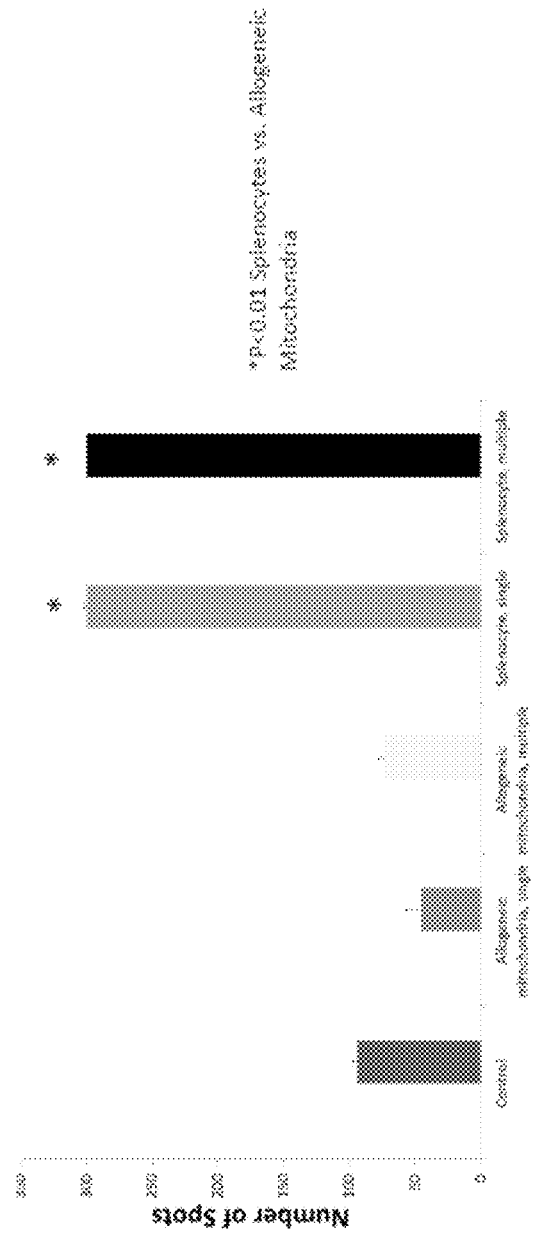
FIG. 19B is a bar graph showing number of spots in mice receiving single or multiple injections of allogenic mitochondria, and single and multiple injections of splenocytes.
Figure 20:
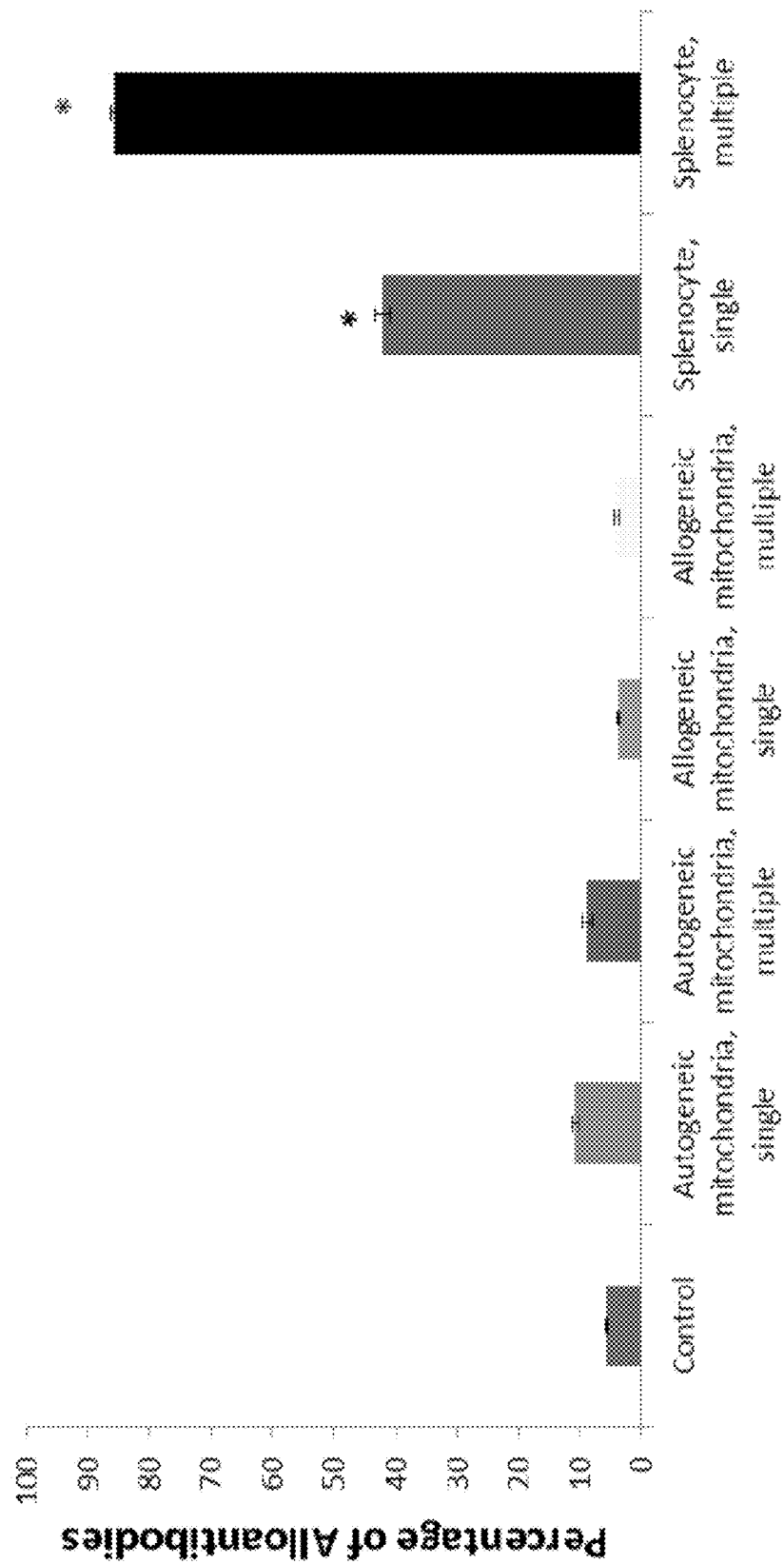
FIG. 20 is a graph showing percentage of alloantibodies in response to single and multiple injections of autogenic and allogeneic mitochondria, and single and multiple injections of splenocytes.

For single injection, the mice received injections on Day 0 and then were allowed to recover for 10 days. On Day 10, immune response was evaluated. For multiple injections, BALB/cJ mice received injections on Day-6, Day-3, and Day 0 and then were allowed to recover for 10 days. On Day 10, immune response was evaluated. FIGS. 19A-19B show T-cell response to single and multiple doses of mitochondria. The results show that there was no T-cell response to single or multiple doses of mitochondria at any concentration. FIG. 20 shows B-cell response to single and multiple doses of mitochondria (*P<0.01 splenocytes vs. autogeneic mitochondria). The concentration for mitochondria was $1 \times 10^7$ organelle/ml, and the concentration for splenocytes was $2 \times 10^7$ cell/ml. The control was a buffer solution. These results demonstrated there is no B-cell response to single or multiple doses of mitochondria.

The second experiment was performed to determine rejection and allo-response. 5-8 weeks old female mice, BALB/cJ (recipient and donor) and C57BL/6J (donor), received single and multiple inter peritoneal injections of mitochondria as described in the first experiment. On Day 10, the mice received a skin graft from C57BL/6J mice. Following skin grafting, the mice were followed for 20 days to determine skin graft rejection and immune response. If the mitochondria could cause immune response, the recipient mouse would reject the grafted skin sooner than the mouse receiving vehicles (control). The results showed that the mouse receiving single or multiple doses of mitochondria did not reject the grafted skin sooner than the mice in the control group. Thus, single or multiple doses of mitochondria do not cause rejection response.

Example 11: Intracellular Delivery Of Drugs

Experiments were performed to determine the optimal concentration of Rhodamine 6G, incubation time, and temperatures for isolated mitochondria to uptake Rhodamine 6G.

Figure 21:
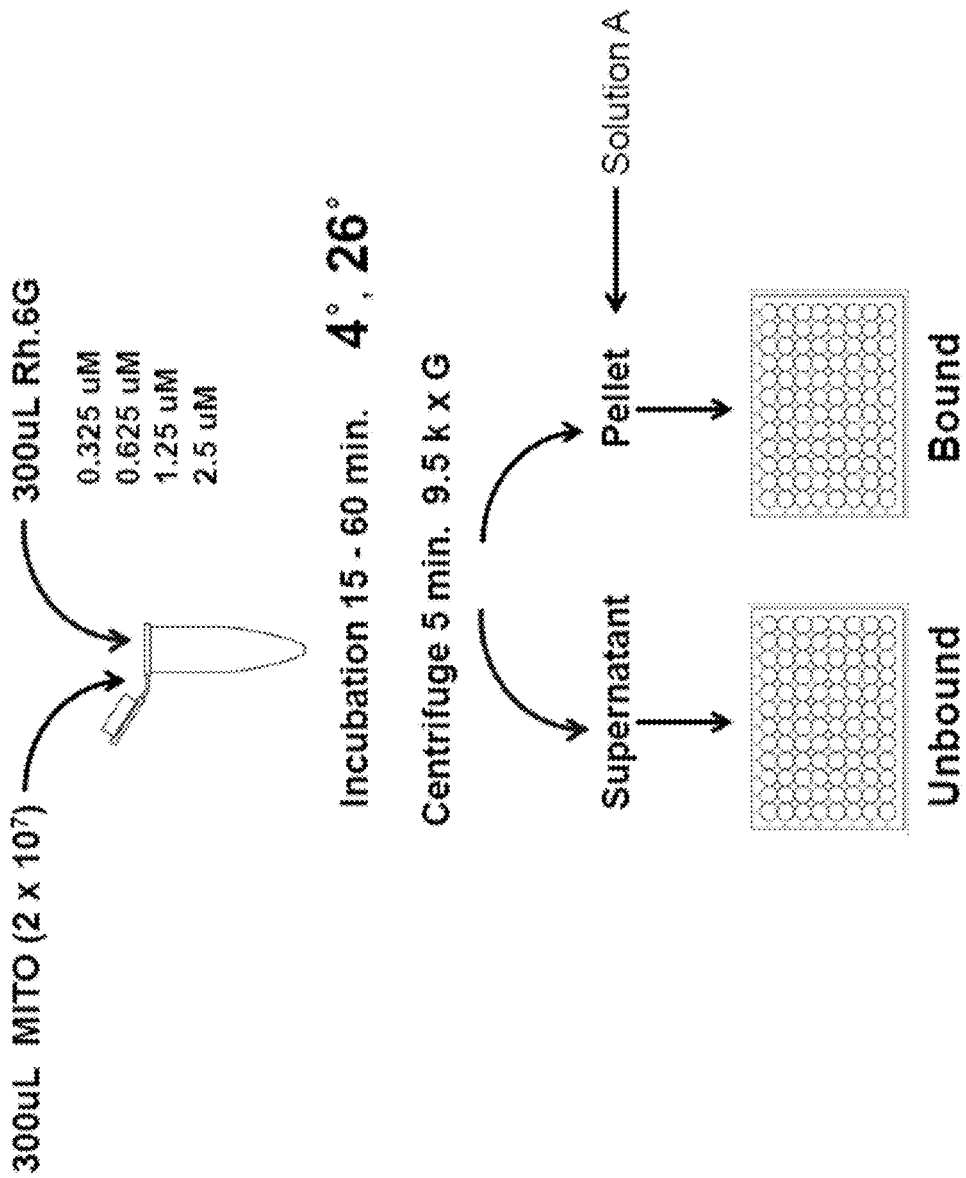
FIG. 21 is a diagram showing protocols of determining the optimal concentration of Rhodamine 6G, incubation time, and temperatures for mitochondria to uptake Rhodamine 6G.
Figure 23A:
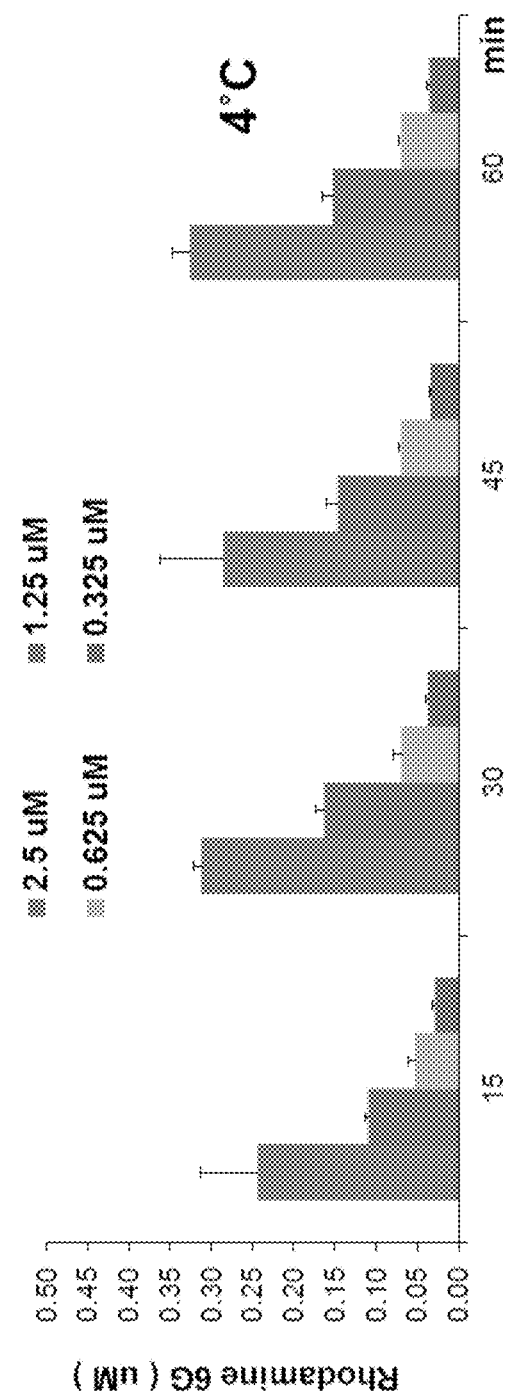
FIG. 23A is a bar graph showing Rhodamine 6G concentration in the bound fraction under different incubating conditions (4° C.).
Figure 23B:
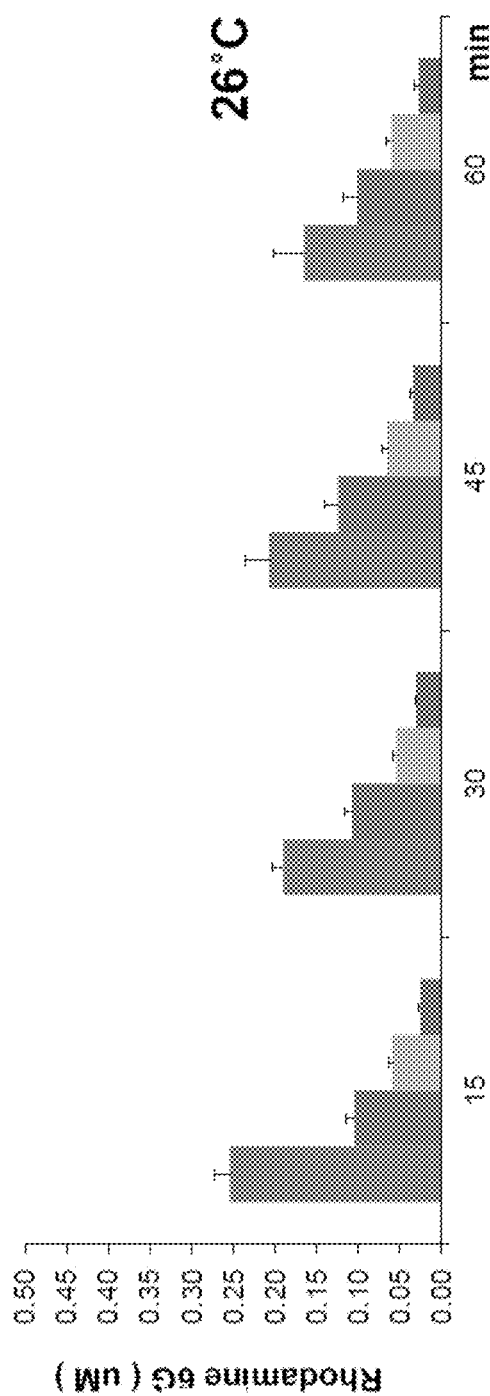
FIG. 23B is a bar graph showing Rhodamine 6G concentration in the bound fraction under different incubating conditions (26° C.).
Figure 24A:
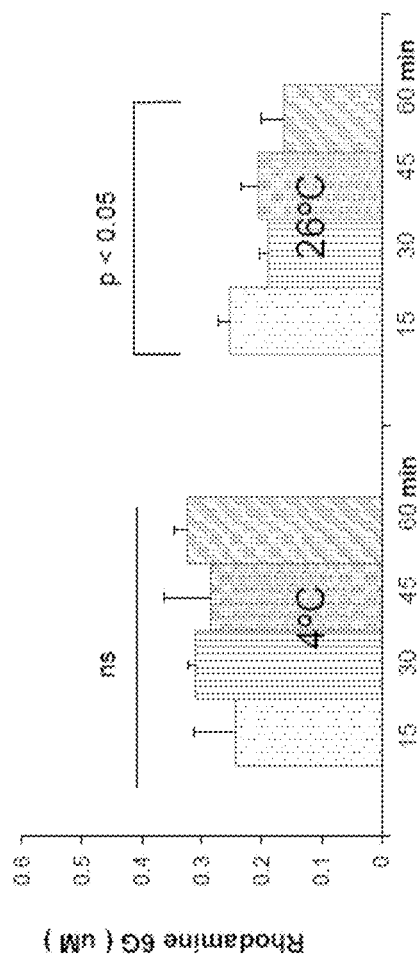
FIG. 24A is a bar graph showing Rhodamine 6G concentration in the bound fraction after incubating mitochondria with 2.5 uM Rhodamine 6G under different incubating conditions.
Figure 24B:
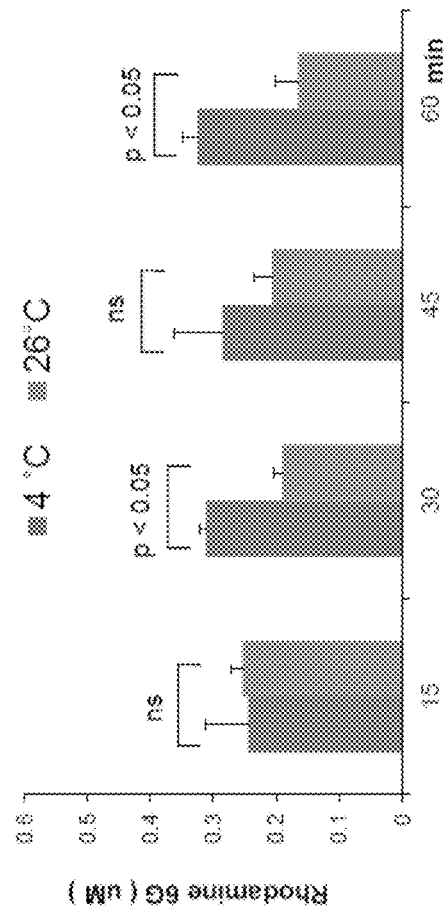
FIG. 24B is a bar graph showing Rhodamine 6G concentration in the bound fraction after incubating mitochondria with 2.5 uM Rhodamine 6G under different incubating conditions.
Figure 25A:
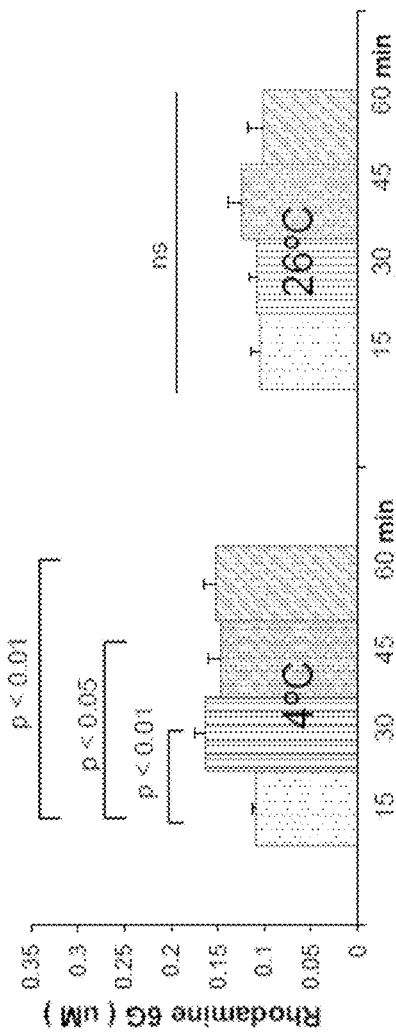
FIG. 25A is a bar graph showing Rhodamine 6G concentration in the bound fraction after incubating mitochondria with 1.25 uM Rhodamine 6G under different incubating conditions.
Figure 25B:
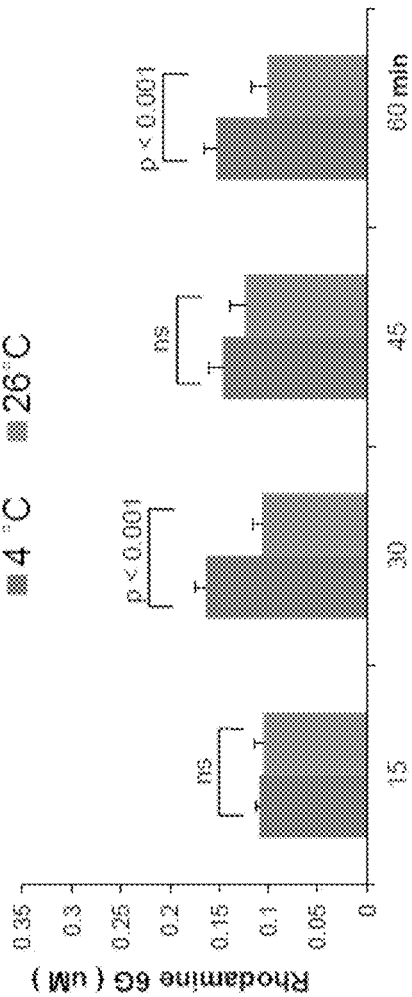
FIG. 25B is a bar graph showing Rhodamine 6G concentration in the bound fraction after incubating mitochondria with 1.25 uM Rhodamine 6G under different incubating conditions.

In this example, $2 \times 10^7$ mitochondria were incubated with 0.325 uM, 0.65 uM, 1.25 um and 2.5 uM Rhodamine 6G. Bound and unbound fractions of Rhodamine 6G were determined following 15, 30, 45 and 60 min incubation at either 4° C. or 26° C. (FIG. 21).

FIGS. 22A-22B, 23A-23B, 24A-24B, and 25A-25B show that when incubating mitochondria with 2.5 uM Rhodamine 6G at 26° C., 60 minutes is significantly worse than 15 minutes. When incubating mitochondria with 1.25 uM Rhodamine 6G at 5° C., 30 minutes, 45 minutes, and 60 minutes are all significantly better than 15 minutes. Furthermore, for incubating mitochondria with either 2.5 uM or 1.25 uM Rhodamine 6G for 30 or 60 minutes, the difference between incubation temperature 4° C. and 26° C. is significant. The bound fraction of Rhodamine 6G at 4° C. is 9-13%, and the bound fraction of Rhodamine 6G at 26° C. is 3-8%. In summary, at optimal conditions, for 1.25 uM Rhodamine 6G, about 0.15 uM Rhodamine 6G are bound in $2 \times 10^7$ mitochondria, and for 2.5 uM Rhodamine 6G, about 0.3 uM Rhodamine 6G are bound in $2 \times 10^7$ mitochondria.

Furthermore, for $2 \times 10^7$ mitochondria, the optimal condition is 2.5 uM Rhodamine 6G, incubated at 4° C. for 30 min.

This example demonstrated the ability of mitochondria to be used as a carrier for intracellular delivery of drugs.

Example 12: Adoptive Mitochondria Transfer Enhances Endothelial Cell Engraftment Stem cell integration and vascularization is a major hurdle for potential therapeutic of stem cells. Experiments were performed to show adoptive mitochondria transfer enhances endothelial cell engraftment.

Human Endothelial Colony Forming Cells (ECFCs) Isolation and Culture

Human ECFCs were isolated from umbilical cord blood samples in accordance with an Institutional Review Board-approved protocol as described in Melero-Martin, J. M., Melero-Martin, J. M., Khan, Z. A., Khan, Z. A., Picard, A., Picard, A., et al. (2007). In vivo vasculogenic potential of human blood-derived endothelial progenitor cells. Blood, 109(11), 4761-4768. ECFCs were cultured on 1% gelatin-coated plates using ECFC-medium: EGM-2 (except for hydrocortisone; Lonza) supplemented with 20% FBS, 1×GPS. All experiments were carried out with ECFCs between passages 5-8.

Isolation and Culture of Human Mesenchymal Stem Cells (MSCs)

Human MSCs were isolated from normal discarded subcutaneous white adipose tissue obtained during clinically indicated procedures in accordance with an Institutional Review Board-approved protocol, as described in Lin, R.-Z., Moreno-Luna, R., Moreno-Luna, R., Muñoz-Hernandez, R., Muñoz-Hernandez, R., Li, D., et al. (2013). Human white adipose tissue vasculature contains endothelial colony-forming cells with robust in vivo vasculogenic potential. Angiogenesis, 16(4), 735-744. Human MSCs were cultured on uncoated plates using MSC-medium: MSCGM (Lonza)

supplemented with 10% MSC-qualified FBS (Hyclone), 1× glutamine-penicillin-streptomycin (GPS; Invitrogen). All experiments were carried out with MSCs between passages 4-6.

Isolation of Mitochondria from ECFCs

ECFCs ($9\times10^6$ cells) were harvested from culture and resuspended in 800 μL of Reagent A from Mitochondria Isolation Kit for Cultured Cells (Thermo Scientific). Cells were lysed on ice using Dounce Homogenization (VWR) for 30 sec. Cell lysates were mixed with 800 μL of Reagent C and then centrifuged at 700 g for 10 minutes at 4° C. The supernatant was transferred to a new tube and centrifuged at 12,000 g for 15 minutes at 4° C. After the centrifugation, the pellet was resuspended in 500 μL of Reagent C and centrifuged again at 12,000 g for 15 minutes at 4° C. The final pellet contains isolated mitochondria ready for transfer.

Mitochondria Transfer into ECFCs

Isolated mitochondria were resuspended in 1 mL of ECFC-medium and added directly to ECFCs in culture. Mitochondria isolated from $9\times10^6$ ECFCs were used to transfer to $3\times10^6$ cells (3:1 donor-to-recipient ratio). Five hours after mitochondria transfer, media were refreshed with new ECFC-medium and recipient ECFCs were then immediately used for in vivo transplantation experiments. Recipient ECFCs are referred to as ECFC-Mito and control ECFCs that did not receive exogenous mitochondria are referred to as ECFC-Control.

In Vivo Transplantation of ECFCs into Immunodeficient Nude Mice

Animal experiments were conducted under a protocol approved by the Institutional Animal Care and Use Committee at Children's Hospital Boston in an AAALAC-approved facility. Human ECFCs ($2\times10^5$ cells; with or without mitochondria transfer) and MSCs ($3\times10^5$ cells), resuspended in 200 μL of collagen-fibrin-laminin gel, were subcutaneously injected on the back of 6-week-old male athymic nu/nu mice (Massachusetts General Hospital, Boston, MA). Mice were euthanized and implants were harvested after 7 days.

Histology, Immunohistochemistry, and Immunofluorescence

Implants were harvested after 7 days. Explanted grafts were fixed overnight in 10% buffered formalin, embedded in paraffin and sectioned (7 μm-thick). Hematoxylin and eosin (H&E)-stained sections were examined for the presence of vascular structures using ImageJ 1.47 v software (National Institutes of Health). Hematoxylin and eosin (H&E) stained sections were examined for the presence of blood vessels containing red blood cells. For immunostaining, sections were deparaffinized and antigen retrieval was carried out with tris-EDTA buffer (10 mM Tris-Base, 2 mM EDTA, 0.05% Tween-20, pH 9.0). Sections were then blocked for 30 min in 5-10% blocking serum and incubated with a mouse anti-human CD31 primary antibody (1:50; abcam) for 1 h at room temperature. Horseradish peroxidase-conjugated mouse secondary antibody (1:200; Vector Laboratories) and 3,3'-diaminobenzidine (DAB) were used for detection of hCD31, followed by hematoxylin counterstaining and Permount mounting. Fluorescent staining was performed using rhodamine-conjugated UEA-1 (1:200) followed by DAPI counterstaining (Vector Laboratories).

Microvessel Density

Microvessel density was reported as the average number of erythrocyte-filled vessels (vessels/mm$^2$) in H&E stained sections from the middle of the implants. The entire area of each section was analyzed. Values reported for each experimental condition correspond to the mean±standard error of the mean (SEM), obtained from four individual implants.

Microscopy

Images were taken using an Axio Observer Z1 inverted microscope (Carl Zeiss) and AxioVision Rel. 4.8 software. Fluorescent images were taken with an ApoTome.2 Optical sectioning system (Carl Zeiss) and 40×/1.4 oil objective lens. Non-fluorescent images were taken with an AxioCam MRc5 camera using a 40×/1.4 objective oil lens.

Statistical Analyses

Data were expressed as mean±standard error of the mean (SEM). Means were compared using unpaired Student's t tests. All statistical analyses were performed using GraphPad Prism v.5 software (GraphPad Software Inc). $P<0.05$ was considered statistically significant.

Results

Figure 26:
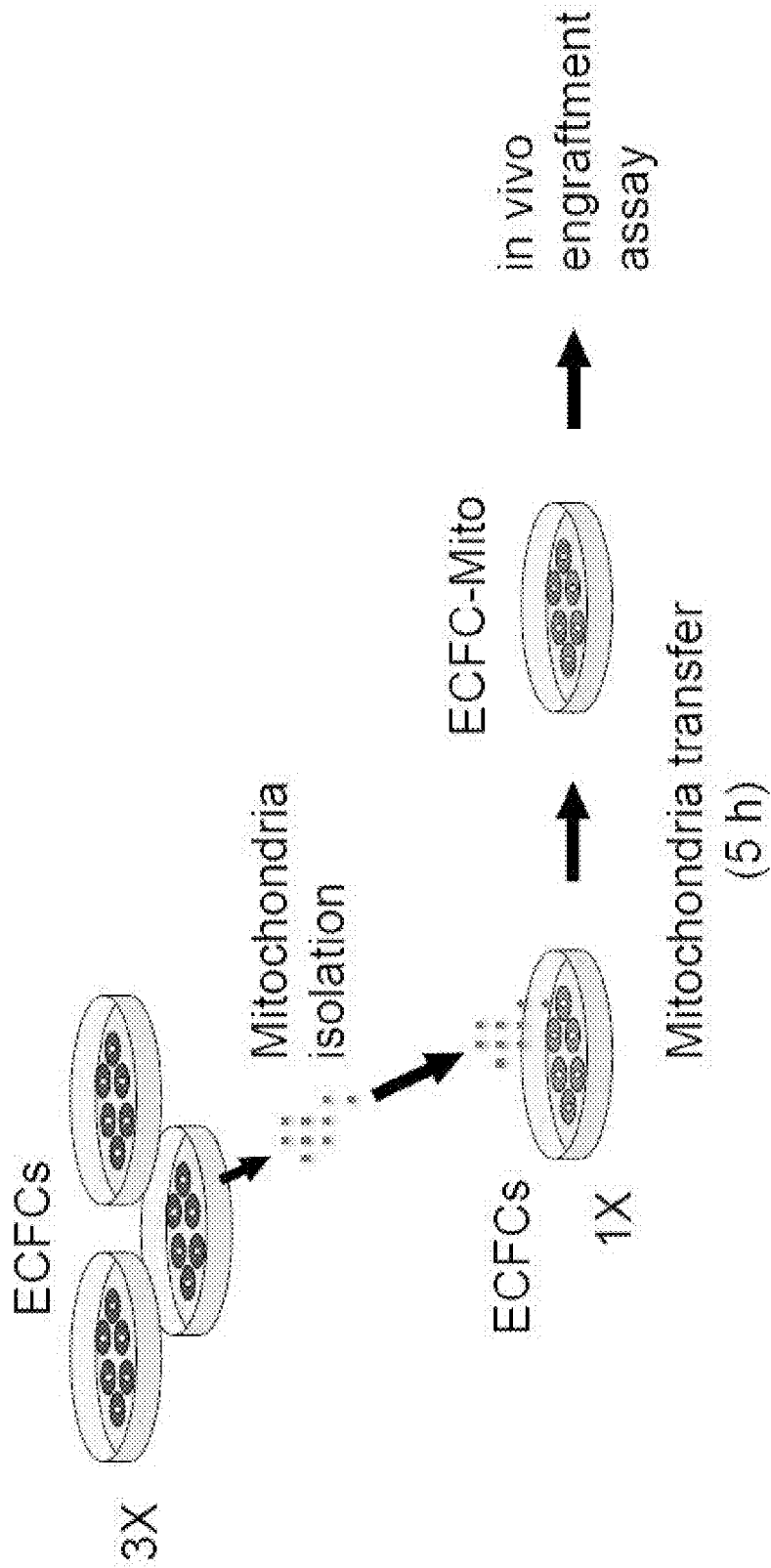
FIG. 26 is a schematic diagram showing transferring adoptive mitochondria into human endothelial colony-forming cells (ECFCs).

Mitochondria were isolated from donor ECFCs and transferred to recipient ECFCs with 3:1 donor-to-recipient ratio. Isolated mitochondria were allowed to be absorbed by recipient ECFCs for 5 hours. Recipient ECFCs receiving exogenous mitochondria (ECFC-Mito) were then transplanted into mice to evaluate their vasculogenic capability (FIG. 26).

ECFCs and MSCs were resuspended in a collagen hydrogel and then subcutaneously injected on the back of immunodeficient nude mice (FIG. 27A). FIG. 27A shows the in vivo vasculogenesis assay. FIG. 27B shows explants harvested 7 days after transplantation. Top images correspond to implants that contained ECFC-Mito ($2\times10^5$ cells) and MSC ($3\times10^5$ cells). Implants containing ECFC-Control ($2\times10^5$ cells) and MSC ($3\times10^5$ cells) served as control.

Figure 28A:
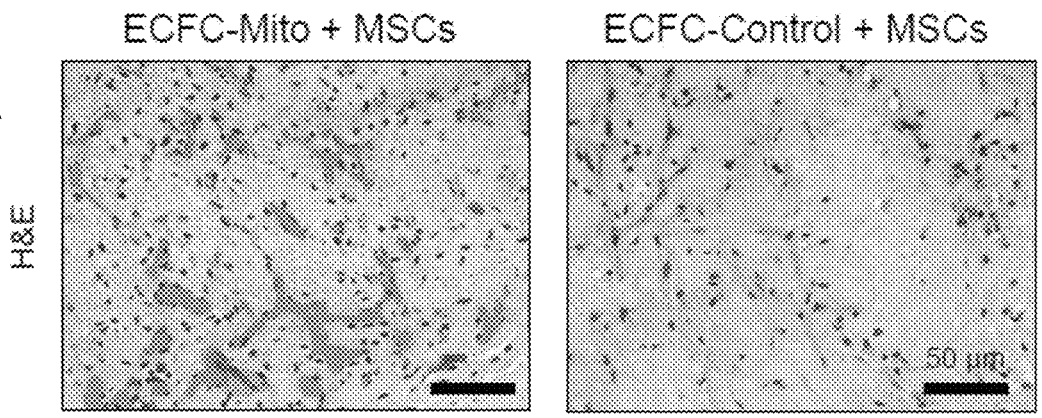
FIG. 28A is two Hematoxylin and Eosin (H&E) stain images showing erythrocyte-filled blood vessels were abundant in implants that contained ECFC-Mitochondria (ECFC-Mito), but not in implants that contained ECFC-Control.
Figure 28B:
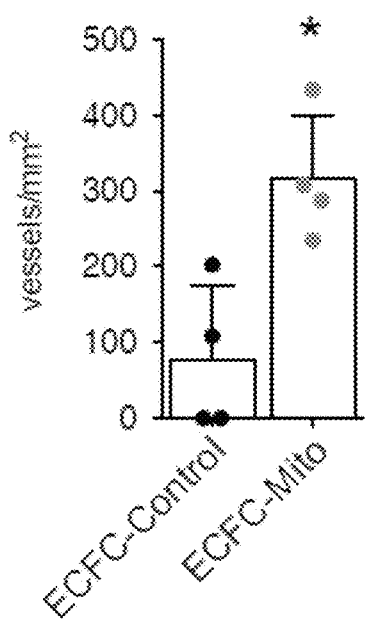
FIG. 28B is a graph showing quantification of microvessel density revealing a higher vascular density in implants that contained ECFC-Mito than in implants that contained ECFC-Control.

H&E images show erythrocyte-filled blood vessels were abundant in implants that contained ECFC-Mito, but not in implants that contained ECFC-Control (FIG. 28A). Microvessel density revealed that a higher vascular density in implants that contained ECFC-Mito than in implants that contained ECFC-Control (FIG. 28B). In FIG. 28B, bars represent mean±SEM (n=4), and the difference was statistically significant (*$P<0.05$).

Figure 29A:
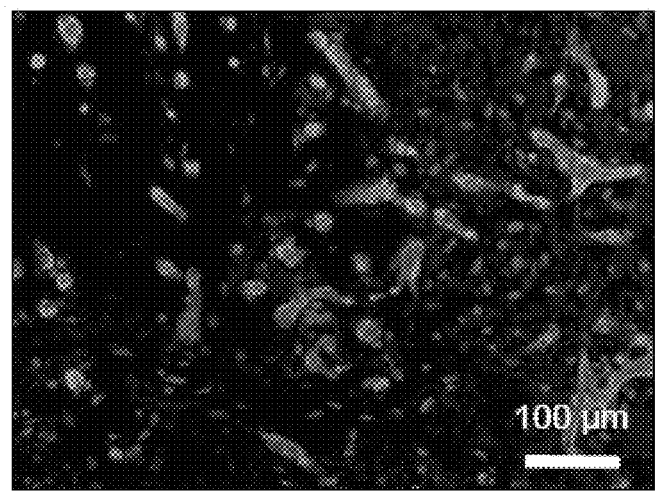
FIG. 29A is an image showing binding of Rhodamine-conjugated UEA-1 lectin in the lumens of the newly-formed perfused vessels.
Figure 29B:
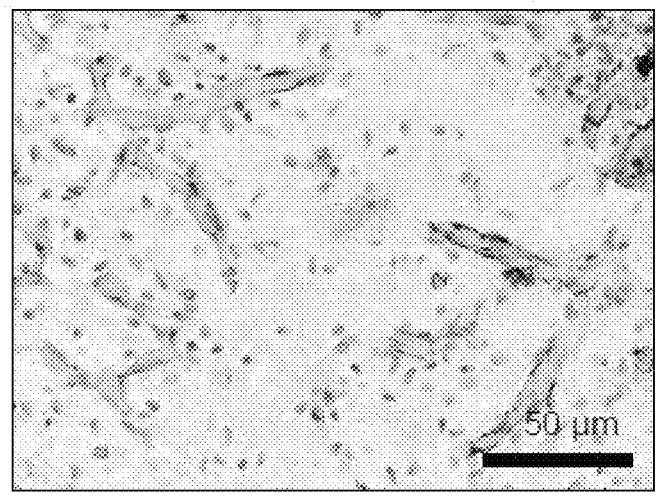
FIG. 29B is a human specific CD31 (h-CD31) immunostaining image of the lumens of the newly-formed perfused vessels.

Recipient ECFCs receiving the exogenous mitochondria (ECFC-Mito) lined the lumens of the newly-formed perfused human vessels. Binding of rhodamine-conjugated UEA-1 lectin demonstrated the formation of human specific vascular lumens in implants that contained ECFC-Mito (FIG. 29A). Of note, UEA-1 lectin binds human endothelium with high affinity, but does not bind murine endothelium. Human specific CD31 (h-CD31) immunostaining confirmed that the lumens of blood vessels were assembled by the transplanted human ECFC-Mito (FIG. 29B).

These experiments show that treating cells with mitochondria enhances cell engraftment. It enhances blood vessel formation in stem cells and enhances cell survival in vivo.

Example 13: Lung Ischemia/Reperfusion Injury

Experiments were preformed to show that mitochondria delivered by vascular infusion through the pulmonary artery are localized within the lung.

Figure 30B:
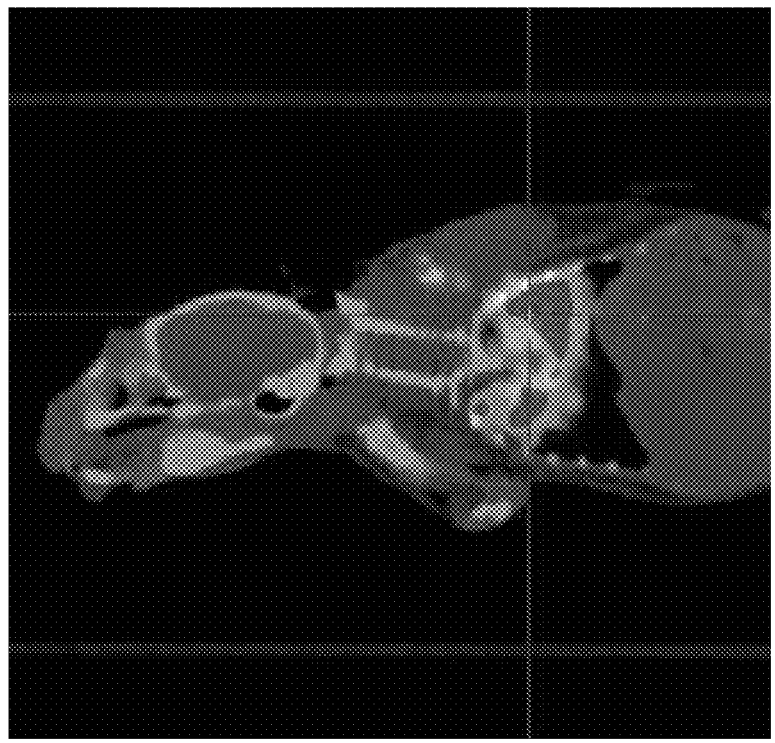
FIG. 30B is a PET/CT image showing mitochondria distribution in both the left and right lungs after $^{18}$F-rhodamine 6G labeled mitochondria were injected into the main pulmonary artery.
Figure 30A:
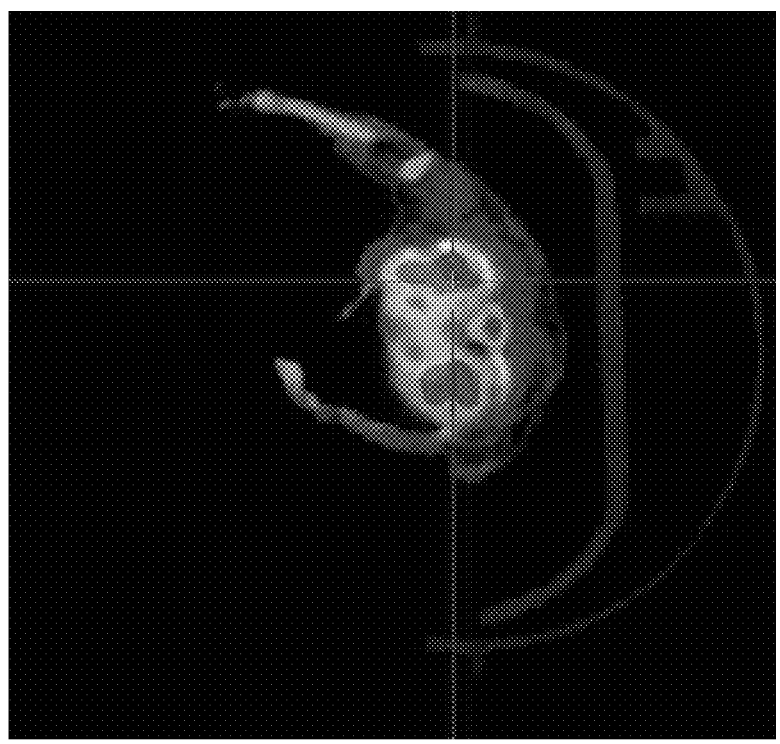
FIG. 30A is a PET/CT image showing mitochondria distribution in both the left and right lungs after $^{18}$F-rhodamine 6G labeled mitochondria were injected into the main pulmonary artery.

A mouse was anesthetized, and ventilated. $^{18}$F-rhodamine 6G labeled mouse mitochondria were injected into the main pulmonary artery (visualized through a sternotomy). Images were obtained 20 minutes later by PPET and μCT using an Alvira PET/SPECT/CT Imaging System (Bruker, Billerica, MA). The images show that delivery of mitochondria into the pulmonary artery of a mouse results in distribution throughout the lungs (FIGS. 30A-30B).

In a separate experiment, the middle and inferior lobes of the right lung in mice were clamped for 1 h (middle) and 2 h (inferior) of ischemia. After unclamping (reperfusion), mice were treated with buffer or with isolated mitochondria. The mice were evaluated 48 h after reperfusion. The result shows that the delivery of intact viable mitochondria reduced lung ischemia reperfusion injury in the mouse model, and the mitochondria preserved lung structure and function following ischemia/reperfusion.

In another experiment, mice were also anesthetized and ventilated. The left hilar structure was clamped for 2 h. Buffer or 3cc (cubic centimeter) of mitochondria solution were injected to the left pulmonary artery, and the mice were sacrificed the next day. The result shows that the delivery of intact viable mitochondria reduces ischemia reperfusion injury in the left lung (FIGS. 31A-31B).

These results demonstrate that mitochondria can be used to aid in the rescue of lungs damaged by ischemia, reperfusion, smoke or toxins, can also be used in lung preservation for use in lung transplantation.

Example 14: Mitochondrial Myopathies

Figure 32:
FIG. 32 is a PET/CT image showing mitochondria located at the optic nerve after $^{18}$F-rhodamine 6G labeled mitochondria were injected into the common carotid artery of the mouse.

Experiments were performed to show that mitochondria can be delivered to optical nerve by injecting mitochondria into common carotid artery of the mouse. The PET scan image shows that the injected mitochondria are located in the optic nerve (FIG. 32).

These results demonstrate that mitochondrial infusion can be used for the treatment of Leber hereditary optic neuropathy (LHON) and other mitochondrial myopathies.

Example 15: Autologous Mitochondrial Transplantation for Dysfunction Following Ischemia Reperfusion Injury Current treatment for pediatric patients who have suffered myocardial ischemia-reperfusion injury include inotropic and mechanical circulatory support. Recovery of myocardial function following extracorporeal membrane oxygenation (ECMO) support is inconsistent, as reflected by 40% failure to separate from ECMO. Mitochondrial damage and dysfunction contribute significantly to the myocardial dysfunction in such patients with ischemia-reperfusion injury. A novel strategy to repair and replenish damaged mitochondria, termed "mitochondrial auto transplantation", has been developed in which healthy autologous mitochondria harvested from non-ischemic skeletal muscle are transplanted into injured myocardium. Examples in this disclosure have demonstrated that transplanted mitochondria restore mitochondrial function and viability, and improve post-ischemic myocardial function by internal and extracellular mechanisms that include high-energy synthesis, transcriptomic and proteomic alteration, and DNA repair.

Patients and Methods

Pediatric patients who required central ECMO support due to ischemia-reperfusion associated myocardial dysfunction following cardiac surgical procedure were eligible for mitochondrial auto-transplantation. Patients were included if they experienced a myocardial ischemic event following cardiac surgery that was not ameliorated by surgical intervention and ECMO support. Patients were excluded if they underwent ECMO cannulation through peripheral vessels (cervical or femoral) as access for myocardial injections is not possible to this approach.

Mitochondrial harvest and isolation can be performed within 20-30 minutes during the same procedure and involves minimal manipulation of muscle tissue. Review of the proposed therapy was provided by two independent physicians who were not involved with the patient's care, and families were extensively counseled regarding the potential risks of the procedure. The treatment was provided under an Innovative Therapies protocol developed by the Boston Children's Hospital Institutional Review Board.

In all patients, the mediastinum was accessed and epicardial echocardiogram was performed to identify regions of myocardial akinesis or hypokinesis. A 6 mm×6 mm piece of healthy rectus abdominis muscle was harvested from the inferior aspect of the field using sharp dissection. Autologous mitochondria ($1\times10^8 \pm 1\times10^5$) were isolated under sterile conditions and suspended in 1 mL Respiration Buffer. Ten 100 uL injections containing $1\times10^7 \pm 1\times10^4$ mitochondria each were delivered by direct injection with a 1 mL tuberculin syringe (28-gauge needle) to the myocardium affected by ischemia-reperfusion, as identified by epicardial echocardiogram. Epicardial echocardiogram was performed at the conclusion of the procedure to assess presence of myocardial hematoma related to injections.

Echocardiograms were read by a blinded reviewer for both global and regional dysfunction segments over the time reported.

Results

Figure 33:
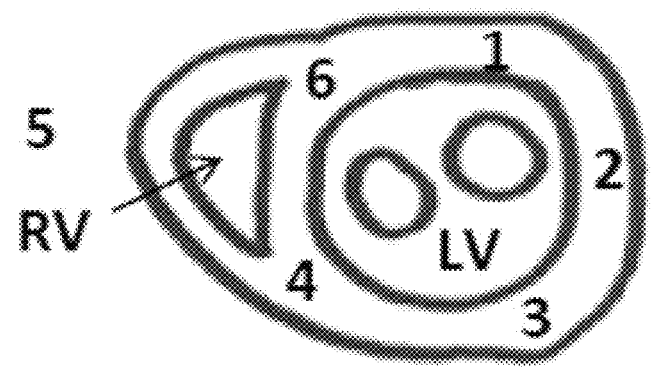
FIG. 33 is a schematic diagram showing cardiac segmentations.

The characteristics and outcomes (mortality and global cardiac function and regional hypokinesis segments) of the patients who underwent mitochondrial auto-transplantation are described in Table 1. The cardiac segmentation schema for Table 1 is shown in FIG. 33. None of the patients experienced arrhythmias or bleeding related to epicardial injections. Four out of five subjects demonstrated improvement in ventricular function and were successfully separated from ECMO support.

This example describes the use of mitochondrial auto-transplantation for myocardial recovery in pediatric patients who require ECMO support due to ischemia-reperfusion injury. Patients did not experience adverse short-term complications related to mitochondrial injection (arrhythmia, intramyocardial hematoma, or scarring), and all demonstrated improvement in ventricular function within several days after treatment. Mitochondrial therapy is most advantageous if delivered as soon after ischemic injury as possible, as evidenced by studies in animal models. The patients in this series were selected because they showed no recovery of myocardial function despite 1-2 days of ECMO support and spontaneous recovery of ventricular function did not seem likely.

The dose of mitochondria and method of delivery were based on animal experiments and extrapolated to human patient cardiac mass. Although epicardial injection was utilized in this study, alternative delivery methods including transcoronary delivery is also possible.

Further, there was no detectable difference in pre- and post-injection markers of systemic inflammatory response syndrome (as evidenced by stable respiratory and renal status), in agreement with animal study data. Autopsy on Patient 1 revealed no signs of inflammation or rejection at sites of injection and white blood cell counts had no clinically relevant change.

This example demonstrates the first clinical application of a novel technique of mitochondrial auto-transplantation that may be useful for patients with ischemia-reperfusion injury.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

| | Case 1 | Case 2 | Case 3 | Case 4 | Case 5 |
|---|---|---|---|---|---|
| Sex | Male | Female | Female | Female | Male |
| Age | 4 days | 2 years | 6 days | 6 months | 25 days |
| Diagnosis | D-TGA | Tricuspid atresia 1B | HLHS | LVOTO | D-TGA |
| Surgical repair | ASO | Fontan | Stage 1 Norwood and RmBTS | Ross Procedure | ASO |
| Cause of Ischemic Injury | Occlusion of the reimplanted ICA | Occlusion of LCA s/t suture at LA appendage | External compression of DKS and RCA by hemostatic agent | Small and tortuous LCA | LV distention/ subendocardial ischemia |
| Ischemic Injury Intervention | Revision of aortocoronary anastomosis | Suture removal with successful restoration of flow | Removal of hemostatic agent and mediastinal compressing thrombus | Removal of hemostatic agent and LCA mobilization | LA vent |
| Duration between ECMO cannulation and treatment | 15 days | 4 days | 2 days | 3 days | 4 days |
| Time from treatment to decannulation | n/a | 3 days | 6 days | 3 days | 4 days |
| Injection Site | Segments 1, 2 | Segment 3 | Segments 4, 5, 6 | Segments 2, 3 | Segments 1, 2, 3 |
| Ventricular function prior to treatment, echocardiogram | Global: Moderate LV systolic dysfunction Regional Hypokinesia: Segments 1, 2, 3 | Global: Severe LV systolic dysfunction Regional Hypokinesia: Segments 3, 4 | Global: Severe RV systolic dysfunction Regional Hypokinexia; Segments 4, 5, 6 | Global: Moderate - severe LV systolic dysfunction Regional Hypokinesin: Segments 2, 3, 4 | Global; Severe LV systolic dysfunction Regional Hypokinesia; Segments 1, 2, 3 |
| Ventricular function 24 hours following treatment, via echocardiogram | Global: Mild LV systolic dysfunction Regional Hypokinesia: Segments 1, 2, 3 | Global: Moderate LV systolic dysfunction Regional Hypokinesia: Segments 3, 4 | n/a | Global: Severe LV systolic dysfunction Regional Hypokinesia: Segments 2, 3, 4 | Global: Mild LV systolic dysfunction Regional Hypokinesia: Segment 2 |
| Ventricular function 48 hours following treatment, via echocardiogram | Global: Mild LV systolic dysfunction Regional Hypokinesio: Segment 2 | n/a | n/a | Global: Mild-moderate LV systolic dysfunction Regional Hypokinesia: Segments 2, 3 | Global: Mild LV systolic dysfunction Regional Hypokinesio: Segments 2, 3 |
| Ventricular function 4-6 days following treatment, via echocardiogram | Global: Mild LV systolic dysfunction Regional Hypokinesia: Segment 2 | Global: Mild LV systolic dysfunction Regional Hypokinesia. none | Global: Normal RV systolic function Regional Hypokinesio: none | Global: Mild to moderate LV systolic dysfunction Regional Hypokinesio: Segments 2.3 | Global: Borderline - mild LV systolic dysfunction Regional Hypokinesia: none |
| Ventricular function 10 days following treatment, via echocardiogram | n/a | Global: Mild LV systolic dysfunction Regional Hypokinesis: none | n/a | Global: Normal LV systolic function Regional Hypokinesia: none | Global: Normal LV systolic function Regional Hypokinesia: none |

TABLE 1-continued

|  | Case 1 | Case 2 | Case 3 | Case 4 | Case 5 |
| --- | --- | --- | --- | --- | --- |
| Mortality Current Status | Deceased Despite recovery of myocardial function, the patient did not tolerate decannulation due to persistent pulmonary, renal, and hepatic insufficiency | Alive Patient discharged on POD 38. Echocardiogram 403 days following therapy showed global moderate dysfunction. | Deceased On POD 30 patient had mild LV dysfunction. The patient ultimately expired from respiratory insufficiency following BDG at 4 months of age | Alive Patient discharged on POD 52. Echocardiogram 119 days following therapy showed global borderline dysfunction. | Alive Patient discharged on POD 30. Echocardiogram 34 days following therapy showed global mild dysfunction. |

Abbreviations:
D-TGA: dextro-transposition of the great arteries
HLHS: hypoplastic left heart syndrome
LVOTO: left ventricular outflow tract obstruction
ASO: arterial switch operation
RmBTS: right modified Blalock-Taussig Shunt
LCA: left coronary artery
POD: post-operative day
DKS: Damus-Kaye-Stansel procedure
ECMO: extracorporeal membrane oxygenation
LV: left ventricle
RV: right ventricle
BDG: bidirectional Glenn

What is claimed is:

1. A method of transplanting an organ into a human subject, the method comprising:
contacting the organ with an effective amount of a composition comprising exogenous mitochondria such that the mitochondria are incorporated within the organ to generate a modified organ comprising the exogenous mitochondria;
and transplanting the organ to the human subject.

2. The method of claim 1, wherein the transplanted organ demonstrates enhanced engraftment after transplantation compared to an organ not comprising exogenous mitochondria.

3. The method of claim 1, wherein the organ is contacted ex vivo or in situ with the composition comprising exogeneous mitochondria prior to transplantation.

4. The method of claim 1, wherein the composition comprising exogeneous mitochondria is perfused through the organ.

5. The method of claim 1, wherein the exogenous mitochondria are xenogeneic, allogeneic, or autogeneic.

6. The method of claim 1, wherein the organ is submerged within the composition comprising exogenous mitochondria.

7. A method of transplanting a heart into a human subject, the method comprising:
contacting the heart with an effective amount of a composition comprising exogenous mitochondria such that the mitochondria are incorporated within the heart to generate a modified heart comprising the exogenous mitochondria;
and transplanting the heart to the human subject.

8. The method of claim 7, wherein the transplanted heart demonstrates enhanced engraftment after transplantation compared to a heart not comprising exogenous mitochondria.

9. The method of claim 7, wherein the heart is contacted ex vivo or in situ with the composition comprising exogeneous mitochondria prior to transplantation.

10. The method of claim 7, wherein the composition comprising exogeneous mitochondria is perfused through the heart.

11. The method of claim 7, wherein the exogeneous mitochondria are xenogeneic, allogeneic, or autogeneic.

12. The method of claim 7, wherein the heart is submerged within the composition comprising exogenous mitochondria.

13. A method of transplanting a kidney into a human subject, the method comprising:
contacting the kidney with an effective amount of a composition comprising exogenous mitochondria such that the mitochondria are incorporated within the kidney to generate a modified kidney comprising the exogenous mitochondria;
and transplanting the kidney to the human subject.

14. The method of claim 13, wherein the transplanted kidney demonstrates enhanced engraftment after transplantation compared to an kidney not comprising exogenous mitochondria.

15. The method of claim 13, wherein the kidney is contacted ex vivo or in situ with the composition comprising exogeneous mitochondria prior to transplantation.

16. The method of claim 13, wherein the composition comprising exogeneous mitochondria is perfused through the kidney.

17. The method of claim 13, wherein the exogeneous mitochondria are xenogeneic, allogeneic, or autogeneic.

18. The method of claim 13, wherein the kidney is submerged within the composition comprising exogenous mitochondria.

19. A method of transplanting a liver into a human subject, the method comprising:
contacting the liver with an effective amount of a composition comprising exogenous mitochondria such that the mitochondria are incorporated within the liver to generate a modified liver comprising the exogenous mitochondria;
and transplanting the liver to the human subject.

20. The method of claim 19, wherein the transplanted liver demonstrates enhanced engraftment after transplantation compared to an liver not comprising exogenous mitochondria.

21. The method of claim 19, wherein the liver is contacted ex vivo or in situ with the composition comprising exogeneous mitochondria prior to transplantation.

22. The method of claim 19, wherein the composition comprising exogeneous mitochondria is perfused through the liver.

23. The method of claim 19, wherein the exogeneous mitochondria are xenogeneic, allogeneic, or autogeneic.

24. The method of claim 19, wherein the liver is submerged within the composition comprising exogenous mitochondria.

* * * * *